United States Patent
Kaneko et al.

(10) Patent No.: US 10,544,227 B2
(45) Date of Patent: Jan. 28, 2020

(54) PHARMACEUTICAL COMPOSITION FOR PREVENTION AND/OR TREATMENT OF ATOPIC DERMATITIS COMPRISING IL-31 ANTAGONIST AS ACTIVE INGREDIENT

(71) Applicant: CHUGAI SEIYAKU KABUSHIKI KAISHA, Tokyo (JP)

(72) Inventors: Akihisa Kaneko, Shizuoka (JP); Yuki Iwayanagi, Shizuoka (JP); Hidetomo Kitamura, Shizuoka (JP); Yoshinobu Higuchi, Shizuoka (JP); Hiroaki Matsushita, Shizuoka (JP); Ryosuke Mihara, Tokyo (JP); Yumi Yamamoto, Tokyo (JP); Tomohisa Saito, Tokyo (JP); Keiko Hirokawa, Tokyo (JP)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 0 days.

(21) Appl. No.: 15/563,743

(22) PCT Filed: Apr. 13, 2016

(86) PCT No.: PCT/JP2016/061859
§ 371 (c)(1),
(2) Date: Oct. 2, 2017

(87) PCT Pub. No.: WO2016/167263
PCT Pub. Date: Oct. 20, 2016

(65) Prior Publication Data
US 2018/0079817 A1    Mar. 22, 2018

(30) Foreign Application Priority Data

Apr. 14, 2015  (JP) ................................ 2015-082699
Mar. 4, 2016  (JP) ................................ 2016-041641

(51) Int. Cl.
| | | |
|---|---|---|
| *A61K 39/395* | (2006.01) | |
| *A61K 45/06* | (2006.01) | |
| *A61K 39/00* | (2006.01) | |
| *C07K 16/28* | (2006.01) | |

(52) U.S. Cl.
CPC .... *C07K 16/2866* (2013.01); *A61K 39/39541* (2013.01); *A61K 45/06* (2013.01); *A61K 2039/505* (2013.01); *C07K 2317/33* (2013.01); *C07K 2317/52* (2013.01); *C07K 2317/76* (2013.01); *C07K 2317/94* (2013.01)

(58) Field of Classification Search
None
See application file for complete search history.

(56) References Cited

U.S. PATENT DOCUMENTS

| | | | |
|---|---|---|---|
| 5,455,030 A | 10/1995 | Ladner et al. | |
| 6,018,032 A | 1/2000 | Koike et al. | |
| 6,019,967 A | 2/2000 | Breton et al. | |
| 7,001,980 B1 | 2/2006 | Parker et al. | |
| 7,064,186 B2 | 6/2006 | Sprecher et al. | |
| 7,250,168 B2 | 7/2007 | Light et al. | |
| 7,482,440 B2 | 1/2009 | Maeda et al. | |
| 7,494,804 B2 | 2/2009 | Maeda et al. | |
| 7,517,965 B2 | 4/2009 | Koga et al. | |
| 7,575,938 B2 | 8/2009 | Chung et al. | |
| 7,579,000 B2 | 8/2009 | Light et al. | |
| 7,622,122 B2 | 11/2009 | Light et al. | |
| 7,622,457 B2 | 11/2009 | Light et al. | |
| 7,638,126 B2 | 12/2009 | Yao et al. | |
| 7,858,756 B2 | 12/2010 | Owens et al. | |
| 7,919,594 B2 | 4/2011 | Smith et al. | |
| 8,075,884 B2 | 12/2011 | Bowdish et al. | |
| 8,076,458 B2 | 12/2011 | Ohta et al. | |
| 8,431,127 B2 * | 4/2013 | Higuchi ............. | C07K 16/2869 424/139.1 |
| 8,575,317 B2 * | 11/2013 | Kuramochi ........ | C07K 16/2866 530/388.22 |
| 9,028,821 B2 | 5/2015 | Hasegawa et al. | |
| 9,198,898 B2 | 12/2015 | Zhang et al. | |
| 9,399,680 B2 | 7/2016 | Kuramochi et al. | |
| 9,745,378 B2 | 8/2017 | Hasegawa et al. | |
| 2003/0096339 A1 | 5/2003 | Sprecher et al. | |
| 2003/0215838 A1 | 11/2003 | Sprecher et al. | |
| 2004/0142422 A1 | 7/2004 | Sprecher et al. | |
| 2004/0223970 A1 | 11/2004 | Afar et al. | |

(Continued)

FOREIGN PATENT DOCUMENTS

| | | |
|---|---|---|
| AU | 2006/214404 | 8/2006 |
| AU | 2007/249713 | 11/2007 |

(Continued)

OTHER PUBLICATIONS

Gershoni et al., "Epitope Mapping," BioDrugs, May 2007;21(3):145-56.
International Preliminary Report on Patentability in International Application No. PCT/JP2016/061859, dated Oct. 26, 2017, 10 pages.
U.S. Appl. No. 12/745,781, Kuramochi et al., filed Sep. 13, 2010 (abandoned).

(Continued)

*Primary Examiner* — Elizabeth C. Kemmerer
(74) *Attorney, Agent, or Firm* — Fish & Richardson P.C.

(57) ABSTRACT

In a non-limiting embodiment, there is provided a pharmaceutical composition for prevention and/or treatment of atopic dermatitis comprising an IL-31 antagonist as an active ingredient, wherein the IL-31 antagonist is repeatedly administered in equal amounts at the same dosing interval to a subject with or potentially with atopic dermatitis, at 0.1 to 1000 mg/body/1 day to 12 weeks, preferably at 0.1 to 1000 mg/body/2 weeks, 0.1 to 1000 mg/body/4 weeks, or 0.1 to 1000 mg/body/8 weeks.

12 Claims, 11 Drawing Sheets
Specification includes a Sequence Listing.

(56) References Cited

U.S. PATENT DOCUMENTS

| | | | |
|---|---|---|---|
| 2006/0182743 | A1 | 8/2006 | Bilsborough |
| 2010/0310556 | A1 | 12/2010 | Higuchi et al. |
| 2011/0129459 | A1 | 6/2011 | Kuramochi et al. |
| 2015/0057255 | A1* | 2/2015 | Zhang ............... A61K 31/4035 |
| | | | 514/171 |
| 2015/0175704 | A1 | 6/2015 | Kuramochi et al. |

FOREIGN PATENT DOCUMENTS

| | | |
|---|---|---|
| AU | 2007/255753 | 12/2007 |
| AU | 2008/332271 | 6/2009 |
| BR | PI0821145-0 | 6/2015 |
| BR | PI0821110-8 | 7/2015 |
| CA | 2 594 490 | 8/2006 |
| CA | 2 633 439 | 11/2007 |
| CA | 2 636 288 | 12/2007 |
| CA | 2 708 065 | 6/2009 |
| CA | 2 708 532 | 6/2009 |
| CN | 1213070 | 8/2005 |
| CN | 1241944 | 2/2006 |
| CN | 1326880 | 7/2007 |
| CN | 100384876 | 4/2008 |
| CN | 100469793 | 3/2009 |
| CN | 101939424 | 1/2011 |
| EA | 009026 | 10/2007 |
| EP | 1 088 831 | 4/2001 |
| EP | 1 188 830 | 3/2002 |
| EP | 1 375 518 | 12/2008 |
| EP | 2 047 863 | 4/2009 |
| EP | 2 236 604 | 10/2010 |
| EP | 2 241 332 | 10/2010 |
| EP | 2 354 161 | 8/2011 |
| EP | 2734549 | 5/2014 |
| JP | 2005-532045 | 10/2005 |
| JP | 5043008 | 10/2012 |
| KR | 2010/0097721 | 9/2010 |
| RU | 2180854 | 3/2002 |
| RU | 2010127292 | 1/2012 |
| RU | 2010/126078 | 1/2013 |
| TW | 2008/10778 | 3/2008 |
| TW | 2009/32266 | 8/2009 |
| WO | WO 94/10354 | 5/1994 |
| WO | WO 94/12215 | 6/1994 |
| WO | WO 96/23071 | 8/1996 |
| WO | WO 97/10354 | 3/1997 |
| WO | WO 99/55735 | 11/1999 |
| WO | WO 00/34317 | 6/2000 |
| WO | WO 00/75314 | 12/2000 |
| WO | WO 01/23556 | 4/2001 |
| WO | WO 02/00721 | 1/2002 |
| WO | WO 02/077230 | 10/2002 |
| WO | WO 2003/060090 | 7/2003 |
| WO | WO 2003/072740 | 9/2003 |
| WO | WO 2003/092602 | 11/2003 |
| WO | WO 2004/003140 | 1/2004 |
| WO | WO 2004/085476 | 10/2004 |
| WO | WO 2004/091543 | 10/2004 |
| WO | WO 2005/079566 | 9/2005 |
| WO | WO 2006/004663 | 1/2006 |
| WO | WO 2006/063864 | 6/2006 |
| WO | WO 2006/063865 | 6/2006 |
| WO | WO 2006/070286 | 7/2006 |
| WO | WO 2006/081573 | 8/2006 |
| WO | WO 2006/088855 | 8/2006 |
| WO | WO 2006/088955 | 8/2006 |
| WO | WO 2006/088956 | 8/2006 |
| WO | WO 2006/118959 | 11/2006 |
| WO | WO 2006/119062 | 11/2006 |
| WO | WO 2006/122079 | 11/2006 |
| WO | WO 2007/108756 | 9/2007 |
| WO | WO 2007/133816 | 11/2007 |
| WO | WO 2007/142325 | 12/2007 |
| WO | WO 2007/143231 | 12/2007 |
| WO | WO 2008/028192 | 3/2008 |
| WO | WO 2008/103432 | 8/2008 |
| WO | WO 2008/132453 | 11/2008 |
| WO | WO 2009/041613 | 4/2009 |
| WO | WO 2009/041621 | 4/2009 |
| WO | WO 2009/041643 | 4/2009 |
| WO | WO 2009/071696 | 6/2009 |
| WO | WO 2009/072598 | 6/2009 |
| WO | WO 2009/072604 | 6/2009 |
| WO | WO 2010/064456 | 6/2010 |
| WO | WO 2010/064697 | 6/2010 |
| WO | WO 2014/208645 | 12/2014 |
| WO | WO 2016/167263 | 10/2016 |

OTHER PUBLICATIONS

U.S. Appl. No. 14/340,883, Kuramochi et al., filed Jul. 25, 2014.
U.S. Appl. No. 15/563,743, Kaneko et al.
Bilsborough, "IL-31 is associated with cutaneous lymphocyte antigen-positive skin homing T cells in patients with atopic dermatitis," J. Allergy Clin. Immunol., Feb. 2006;117(2):418-25.
Dillon et al., "Interleukin 31, a cytokine produced by activated T cells, induces dermatitis in mice," Nat. Immunol., Jul. 2004;5(7):752-60 Epub Jun. 6, 2004.
Kim et al., "IL-31 Serum Protein and Tissue rnRNA Levels in Patients with Atopic Dermatitis," Ann Dermatol. Nov. 2011;23(4):468-73. doi: 10.5021/ad.2011.23.4.468. Epub Nov. 3, 2011.
Nemoto et al., "Phase I Trial of IL-31 Receptor Antibody CIM331 in Healthy Adult Males and Atopic Dermatitis Patients," Nihon Hihuka Gakkai Zasshi. 2014;124(4):779(P7-5) (with English translation).
Nemoto et al., "Phase I Trial of IL-31 Receptor Antibody CIM331 in Healthy Adult Males and Atopic Dermatitis Patients," Poster session of the 113th Annual Meeting of the Japanese Dermatological Association, May 30, 2014, 9 pages (with English translation).
Raap et al., "Correlation of IL-31 serum levels with severity of atopic dermatitis," J. Allergy Clin. Immunol., Aug. 2008;122(2):421-423 doi: 10.1016/j.jaci. 2008.05.047.
Takaoka et al., "Expression of IL-31 gene transcripts in NC/Nga mice with atopic dermatitis," Eur J Pharmacol. Jun. 1, 2005;516(2):180-1.
Yamaguchi et al., "Characterization of itch-associated responses of NC mice with mite-induced chronic dermatitis," J Dermatol Sci. Jan. 2001;25(1):20-8.
International Search Report for App. Ser. No. PCT/JP2016/061859, dated May 31, 2016, 2 pages.
Beiboer et al., "Guided Selection of a Pan Carcinoma Specific Antibody Reveals Similar Binding Characteristics yet Structural Divergence Between the Original Murine Antibody and its Human Equivalent," J Mol Biol, Feb. 25, 2000, 296(3):833-49.
Bendig, "Humanization of rodent monoclonal antibodies by CDR grafting," METHODS: A Comparison to Methods in Enzymology, 1995, 8:83-93.
Benjamini et al., Immunology: A Short Course, 2nd Edition, 1991, p. 40.
Berglund et al., "The epitope space of the human proteome," Protein Sci., Apr. 2008, 17(4):606-13. doi: 10.1110/ps.073347208.
Burgess et al., "Possible dissociation of the heparin-binding and mitogenic activities of heparin-binding (acidic fibroblast) growth factor-1 from its receptor-binding activities by site-directed mutagenesis of a single lysine residue," J. Cell. Biol., Nov. 1990, 111:2129-2138.
Casset et al., "A peptide mimetic of an anti-CD4 monoclonal antibody by rational design," Biochem Biophys Res Commun., Jul. 18, 2003, 307:198-205.
Casiellani et al., "Interleukin-31: A New Cytokine Involved in Inflammation of the Skin," Int. J. Immunopathol. Pharmacol., Dec. 2006, 19(1):1-4.
Chen et al., "Selection and analysis of an optimized anti-VEGF antibody: crystal structure of an affinity-matured Fab in complex with antigen," J Mol Biol., Nov. 5, 1999, 293(4):865-81.
Chirino et al., "Minimizing the immunogenicity of protein therapeutics," Drug Discov. Today, Jan. 2004, 9(2):82-90.
Cork et al., "Epidermal barrier dysfunction in atopic dermatitis," J. Invest. Dermatol., Aug. 2009, 129(8):1892-908.

(56) References Cited

OTHER PUBLICATIONS

De Pascalis et al., "Grafting of 'abbreviated' complementarity-determining regions containing specificity-determining residues essential for ligand contact to engineer a less immunogenic humanized monoclonal antibody," J. Immunol., Sep. 15, 2002, 169(6):3076-84.
Dillon et al., "Transgenic Mice Overexpressing a Novel Cytokine (IL-31) Develop a Severe Pruritic Skin Phenotype Resembling Atopic Dermatitis," Eur. Cytokine Netw., Sep. 2003, 14(suppl.):81 (#223).
Diveu et al., "Predominant expression of the long isoform of the GP130-like (GPL) receptor is required for interleukin-31 signaling," Eur. Cytokine Netw., Dec. 2004, 15:291-302.
Diveu et al., "GPL, a novel cytokine receptor related to GP130 and leukemia inhibitory factor receptor," J. Biol. Chem., Dec. 12, 2003, 278(50):49850-49859.
Ewert et al., "Stability improvement of antibodies for extracellular and intracellular applications: CDR grafting to stable frameworks and structure-based framework engineering," Methods, Oct. 2004, 34:184-199.
Ghilardi et al., "A novel type I cytokine receptor is expressed on monocytes, signals proliferation, and activates STAT-3 and STAT-5," J. Biol. Chem., May 10, 2002, 27(19):16831-16836. Epub Mar. 4, 2002.
Grimstad et al., "Anti-interleukin-31-antibodies ameliorate scratching behaviour in NC/Nga mice: a model of atopic dermatitis," Exp. Dermatol., Jan. 2009, 18(1):35-43.
Hanes et al., "Picomolar affinity antibodies from a fully synthetic naive library selected and evolved by ribosome display," Nat. Biotechnol., Dec. 2000, 18(12):1287-1292.
Higa et al., "Administration of anti-interleukin 18 antibody fails to inhibit development of dermatitis in atopic dermatitis-model mice NC/Nga," Br. J. Dermatol., Jul. 2003, 149:39-45.
Holm et al., "Functional mapping and single chain construction of the anti-cytokeratin 8 monoclonal antibody TS1," Mol Immunol., Feb. 2007, 44(6):1075-84. Epub Sep. 20, 2006.
Hudson et al., "Recombinant antibody fragments," Current Opinion in Biotechnology, Aug. 31, 1998, 9(4):395-402.
Klimka et al., "Human anti-CD30 recombinant antibodies by guided phage antibody selection using cell panning," Br J Cancer, Jul. 2000, 83(2):252-60.
Krauss et al., "Impact of antibody framework residue VH-71 on the stability of a humanised anti-MUC1 scFv and derived immunoenzyme," Br. J. Cancer, May 4, 2004, 90:1863-70.
Lazar et al., "Transforming growth factor alpha: mutation of aspartic acid 47 and leucine 48 results in different biological activities," Mol. Cell. Biol., Mar. 1988, 8:1247-1252.
Levin et al., "Optimizing the affinity and specificity of proteins with molecular display," Mol. Biosyst., 2006, 2(1):49-57 (Epub Nov. 8, 2005).
MacCallum et al., "Antibody-antigen Interactions: Contact Analysis and Binding Site Topography," J. Mol. Biol., Oct. 11, 1996, 262:732-45.
MacNeal, Robert J., "Itching (Pruritus): Approach to the Dermatologic Patient," Merck Manual Professional #TB_109_01, May 2009, 6 pages [retrieved on Jun. 10, 2011]. Retrieved from the Internet: http://www.merckmanuals.com/professional/sec10/ch109/ch109d.html, 6 pages.
Marks et al., "By-passing immunization. building high affinity human antibodies by chain shuffling," Bio/Technology (N.Y.), Jul. 1992, 10(7):779-83.
Monies-Torres et al., "Biological Treatments in Atopic Dermatitis," J Clin Med., Apr. 3, 2015, 4(4):593-613. doi: 10.3390/jcm4040593.
Nagata et al., "Novel IL-31 cytokine," Rheumatology, 2006, 35:282-286 (in Japanese, with concise explanation of Japanese reference in English).
Nemoto et al., "The first trial of CIM331, a humanized antihuman interleukin-31 receptor A antibody, in healthy volunteers and patients with atopic dermatitis to evaluate safety, tolerability and pharmacokinetics of a single dose in a randomized, double-blind, placebo-controlled study," Br J Dermatol, Feb. 2016, 174(2):296-304. doi: 10.1111/bjd.14207. Epub Dec. 19, 2015.
Neis et al., "Enhanced expression levels of IL-31 correlate with IL-4 and IL-13 in atopic and allergic contact dermatitis," J. Allergy Clin. Immunol., Oct. 2006, 118(4):930-937. Epub Sep. 1, 2006.
Ohno et al., "Antigen-binding specificities of antibodies are primarily determined by seven residues of VH," Proc. Natl. Acad. Sci. USA, May 1985, 82(9):2945-9.
Onda et al., "Lowering the isoelectric point of the Fv portion of recombinant immunotoxins leads to decreased nonspecific animal toxicity without affecting antitumor activity," Cancer Res., Jul. 1, 2001, 61(13):5070-5077.
Padlan et al., "Identification of specificity-determining residues in antibodies," FASEB J., Jan. 1995, 9:133-139.
Padlan et al., "X-ray crystallography of antibodies," Adv Protein Chem., 1996, 49:57-133.
Paul, "Structure and function of immunoglobulins," Fundamental Immunology, Third Edition, 1993, pp. 292-295.
Pharmacokinetics and Pharmacodynamics of Biotech Drugs: Principles and Case-Studies in Drug Development, Ed. Bernd Meibohm, Wiley-VCH Verlag GmbH & Co. KGaA, Chapter 3, pp. 45-91 (2006).
Phillips, "The challenge of gene therapy and DNA delivery," J. Pharm. Pharmacol., Sep. 2001, 53:1169-74.
Pirollo et al., "Targeted delivery of small interfering RNA: approaching effective cancer therapies," Cancer Res., Mar. 1, 2008, 68:1247-50.
R&D Systems, Inc., "Anti-human IL-31 RA Antibody," Catalog No. AF2769, Oct. 22, 2008, 1 page.
R&D Systems, Inc., "Biotinylated Anti-human IL-31 RA Antibody," Catalog No. BAF2769, Nov. 4, 2005, 1 page.
Rader et al., "A phage display approach for rapid antibody humanization: designed combinatorial V gene libraries," Proc. Natl. Acad. Sci. USA, Jul. 1998, 95(15):8910-5.
"Randomized, double-blind, placebo-controlled, multi-center, multi-dose Phase II study of anti-interleukin-31 receptor A monoclonal antibody CIM331 (nemolizumab) in patients with moderate-to-severe atopic dermatitis," Abst F053, 74th Annu Meet Am Acad Dermatol (AAD), Mar. 4-8, 2016, Washington, DC.
Roitt et al., Immunology, M., Mir, 2000, pp. 110, 150, and 537-539 (each with English translation).
Rose-John et al., "Interleukin-6 biology is coordinated by membrane-bound and soluble receptors: role in inflammation and cancer," J. Leukoc. Biol., Aug. 2006, 80(2):227-36. Epub May 17, 2006.
Rudikoff et al., "Single amino acid substitution altering antigen-binding specificity," Proc. Natl. Acad. Sci. USA, Mar. 1982, 79(6):1979-83.
Ruzicka et al., "Anti-Interleukin-31 Receptor A Antibody for Atopic Dermatitis," N Engl J Med., Mar. 2, 2017, 376(9):826-835. doi: 10.1056/NEJMoa1606490.
"Safety and tolerability of a humanized monoclonal antibody to the Interleukin-31 receptor; results of a phase I, single ascending dose study, in healthy volunteers and patients with atopic dermatitis," Abst FC03.9, 22nd Congr Eur Acad Dermatol Venereol (EADV), Oct. 3-6, 2013, Istanbul.
Sato et al., "Reshaping a human antibody to inhibit the interleukin 6-dependent tumor cell growth," Cancer Res., Feb. 15, 1993, 53:851-856.
Singer et al., Genes & Genomes, 1998, 1:63 (with English translation).
Sonkoly et al., "IL-31: a new link between T cells and pruritus in atopic skin inflammation," J. Allergy Clin. Immunol., Feb. 2006, 117:411-417.
Tan et al., "Engineering the isoelectric point of a renal cell carcinoma targeting antibody greatly enhances scFv solubility," Oct. 1998, Immunotechnology, 4(2):107-114.
Vajdos et al., "Comprehensive functional maps of the antigen-binding site of an anti-ErbB2 antibody obtained with shotgun scanning mutagenesis," J. Mol. Biol., Jul. 5, 2002, 320(2):415-28.
Vidal et al., "Making sense of antisense," Dec. 2005, Eur. J. Cancer, 41:2812-18.

(56) References Cited

OTHER PUBLICATIONS

Yagi et al., "Interleukin-31 stimulates production of inflammatory mediators from human colonic subepithelial myofibroblasts," Int. J. Mol. Med., Jun. 2007, 19(6):941-946.

Yang et al., "CDR walking mutagenesis for the affinity maturation of a potent human anti-HIV-1 antibody into the picomolar range," J. Mol. Biol., Dec. 1, 1995, 254(3):392-403.

Zhang et al., "Structures and biological functions of IL-31 and IL-31 receptors," Cytokine Growth Factor Rev., Oct.-Dec. 2008, 19:347-356. Epub Oct. 15, 2008.

USPTO Restriction Requirement in U.S. Appl. No. 12/303,684, dated Aug. 23, 2010, 7 pages.

USPTO Non-Final Office Action in U.S. Appl. No. 12/303,684, dated Oct. 14, 2010, 18 pages.

USPTO Restriction Requirement in U.S. Appl. No. 12/303,684, dated Jun. 21, 2011, 5 pages.

USPTO Final Office Action in U.S. Appl. No. 12/303,684, dated Oct. 14, 2011, 17 pages.

USPTO Non-Final Office Action in U.S. Appl. No. 12/303,684, dated Aug. 26, 2014, 10 pages.

USPTO Non-Final Office Action in U.S. Appl. No. 12/746,229, dated Jun. 16, 2011, 16 pages.

USPTO Restriction Requirement in U.S. Appl. No. 12/746,229, dated Apr. 12, 2012, 5 pages.

USPTO Restriction Requirement in U.S. Appl. No. 12/746,229, dated Jun. 25, 2012, 4 pages.

USPTO Restriction Requirement in U.S. Appl. No. 12/809,138, dated Dec. 13, 2012, 8 pages.

Kasutani et al., "Anti-IL-31 receptor antibody is shown to be a potential therapeutic option for treating itch and dermatitis in mice," Br J Pharmacol, Nov. 2014, 171(22):5049-58.

\* cited by examiner

Symobl for reference: ●:Placebo ▲:0.1 mg/kg ◆:0.5 mg/kg ■:2.0 mg/kg, Gray area and error bar: 90% prediction interval

SEQUENCE LISTING

<160> NUMBER OF SEQ ID NOS: 15

<210> SEQ ID NO 1
<211> LENGTH: 5
<212> TYPE: PRT
<213> ORGANISM: Artificial sequence
<220> FEATURE:
<223> OTHER INFORMATION: An artificially synthesized peptide sequence

<400> SEQUENCE: 1

Gly Tyr Ile Met Asn
1               5

<210> SEQ ID NO 2
<211> LENGTH: 17
<212> TYPE: PRT
<213> ORGANISM: Artificial sequence
<220> FEATURE:
<223> OTHER INFORMATION: An artificially synthesized peptide sequence

<400> SEQUENCE: 2

Leu Ile Asn Pro Tyr Asn Gly Gly Thr Asp Tyr Asn Pro Gln Phe Gln
1               5                   10                  15

Asp

<210> SEQ ID NO 3
<211> LENGTH: 12

```
<212> TYPE: PRT
<213> ORGANISM: Artificial sequence
<220> FEATURE:
<223> OTHER INFORMATION: An artificially synthesized peptide sequence

<400> SEQUENCE: 3

Asp Gly Tyr Asp Asp Gly Pro Tyr Thr Leu Glu Thr
1               5                   10

<210> SEQ ID NO 4
<211> LENGTH: 11
<212> TYPE: PRT
<213> ORGANISM: Artificial sequence
<220> FEATURE:
<223> OTHER INFORMATION: An artificially synthesized peptide sequence

<400> SEQUENCE: 4

Gln Ala Ser Glu Asp Ile Tyr Ser Phe Val Ala
1               5                   10

<210> SEQ ID NO 5
<211> LENGTH: 7
<212> TYPE: PRT
<213> ORGANISM: Artificial sequence
<220> FEATURE:
<223> OTHER INFORMATION: An artificially synthesized peptide sequence

<400> SEQUENCE: 5

Asn Ala Gln Thr Glu Ala Gln
1               5

<210> SEQ ID NO 6
<211> LENGTH: 9
<212> TYPE: PRT
<213> ORGANISM: Artificial sequence
<220> FEATURE:
<223> OTHER INFORMATION: An artificially synthesized peptide sequence

<400> SEQUENCE: 6

Gln His His Tyr Asp Ser Pro Leu Thr
1               5

<210> SEQ ID NO 7
<211> LENGTH: 121
<212> TYPE: PRT
<213> ORGANISM: Artificial sequence
<220> FEATURE:
<223> OTHER INFORMATION: An artificially synthesized peptide sequence

<400> SEQUENCE: 7

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
                20                  25                  30

Ile Met Asn Trp Val Arg Gln Ala Pro Gly Gln Gly Leu Glu Trp Met
            35                  40                  45

Gly Leu Ile Asn Pro Tyr Asn Gly Gly Thr Asp Tyr Asn Pro Gln Phe
        50                  55                  60

Gln Asp Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Gly Tyr Asp Asp Gly Pro Tyr Thr Leu Glu Thr Trp Gly
                100                 105                 110
```

```
Gln Gly Thr Leu Val Thr Val Ser Ser
        115                 120
```

<210> SEQ ID NO 8
<211> LENGTH: 107
<212> TYPE: PRT
<213> ORGANISM: Artificial sequence
<220> FEATURE:
<223> OTHER INFORMATION: An artificially synthesized peptide sequence

<400> SEQUENCE: 8

```
Asp Ile Gln Met Thr Gln Ser Pro Ser Ser Leu Ser Ala Ser Val Gly
1               5                   10                  15

Asp Arg Val Thr Ile Thr Cys Gln Ala Ser Glu Asp Ile Tyr Ser Phe
            20                  25                  30

Val Ala Trp Tyr Gln Gln Lys Pro Gly Lys Ala Pro Lys Leu Leu Ile
        35                  40                  45

Tyr Asn Ala Gln Thr Glu Ala Gln Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln His Tyr Asp Ser Pro Leu
                85                  90                  95

Thr Phe Gly Gly Gly Thr Lys Val Glu Ile Lys
            100                 105
```

<210> SEQ ID NO 9
<211> LENGTH: 445
<212> TYPE: PRT
<213> ORGANISM: Artificial sequence
<220> FEATURE:
<223> OTHER INFORMATION: An artificially synthesized peptide sequence

<400> SEQUENCE: 9

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Ile Met Asn Trp Val Arg Gln Ala Pro Gly Gln Gly Leu Glu Trp Met
        35                  40                  45

Gly Leu Ile Asn Pro Tyr Asn Gly Gly Thr Asp Tyr Asn Pro Gln Phe
    50                  55                  60

Gln Asp Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Gly Tyr Asp Asp Gly Pro Tyr Thr Leu Glu Thr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
```

```
                    180                 185                 190
Pro Ser Ser Asn Phe Gly Thr Gln Thr Tyr Thr Cys Asn Val Asp His
                195                 200                 205

Lys Pro Ser Asn Thr Lys Val Asp Lys Thr Val Glu Arg Lys Ser Cys
    210                 215                 220

Val Glu Cys Pro Pro Cys Pro Ala Pro Val Ala Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Asp Val Ser Gln Glu Asp Pro Glu
    260                 265                 270

Val Gln Phe Asn Trp Tyr Val Asp Gly Val Glu Val His Asn Ala Lys
            275                 280                 285

Thr Lys Pro Arg Glu Glu Gln Phe Asn Ser Thr Phe Arg Val Val Ser
    290                 295                 300

Val Leu Thr Val Val His Gln Asp Trp Leu Asn Gly Lys Glu Tyr Lys
305                 310                 315                 320

Cys Lys Val Ser Asn Lys Gly Leu Pro Ala Pro Ile Glu Lys Thr Ile
                325                 330                 335

Ser Lys Thr Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Met Leu Asp Ser
385                 390                 395                 400

Asp Gly Ser Phe Phe Leu Tyr Ser Lys Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Pro
        435                 440                 445

<210> SEQ ID NO 10
<211> LENGTH: 214
<212> TYPE: PRT
<213> ORGANISM: Artificial sequence
<220> FEATURE:
<223> OTHER INFORMATION: An artificially synthesized peptide sequence

<400> SEQUENCE: 10

Asp Ile Gln Met Thr Gln Ser Pro Ser Ser Leu Ser Ala Ser Val Gly
1               5                   10                  15

Asp Arg Val Thr Ile Thr Cys Gln Ala Ser Glu Asp Ile Tyr Ser Phe
            20                  25                  30

Val Ala Trp Tyr Gln Gln Lys Pro Gly Lys Ala Pro Lys Leu Leu Ile
        35                  40                  45

Tyr Asn Ala Gln Thr Glu Ala Gln Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln His His Tyr Asp Ser Pro Leu
                85                  90                  95

Thr Phe Gly Gly Gly Thr Lys Val Glu Ile Lys Arg Thr Val Ala Ala
```

```
            100                 105                 110
Pro Ser Val Phe Ile Phe Pro Ser Asp Glu Gln Leu Lys Ser Gly
        115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
        195                 200                 205

Phe Asn Arg Gly Glu Cys
        210

<210> SEQ ID NO 11
<211> LENGTH: 764
<212> TYPE: PRT
<213> ORGANISM: Homo sapiens

<400> SEQUENCE: 11

Met Cys Ile Arg Gln Leu Lys Phe Phe Thr Thr Ala Cys Val Cys Glu
1               5                   10                  15

Cys Pro Gln Asn Ile Leu Ser Pro Gln Pro Ser Cys Val Asn Leu Gly
            20                  25                  30

Met Met Trp Thr Trp Ala Leu Trp Met Leu Pro Ser Leu Cys Lys Phe
        35                  40                  45

Ser Leu Ala Ala Leu Pro Ala Lys Pro Glu Asn Ile Ser Cys Val Tyr
    50                  55                  60

Tyr Tyr Arg Lys Asn Leu Thr Cys Thr Trp Ser Pro Gly Lys Glu Thr
65                  70                  75                  80

Ser Tyr Thr Gln Tyr Thr Val Lys Arg Thr Tyr Ala Phe Gly Glu Lys
                85                  90                  95

His Asp Asn Cys Thr Thr Asn Ser Ser Thr Ser Glu Asn Arg Ala Ser
            100                 105                 110

Cys Ser Phe Phe Leu Pro Arg Ile Thr Ile Pro Asp Asn Tyr Thr Ile
        115                 120                 125

Glu Val Glu Ala Glu Asn Gly Asp Gly Val Ile Lys Ser His Met Thr
    130                 135                 140

Tyr Trp Arg Leu Glu Asn Ile Ala Lys Thr Glu Pro Pro Lys Ile Phe
145                 150                 155                 160

Arg Val Lys Pro Val Leu Gly Ile Lys Arg Met Ile Gln Ile Glu Trp
                165                 170                 175

Ile Lys Pro Glu Leu Ala Pro Val Ser Ser Asp Leu Lys Tyr Thr Leu
            180                 185                 190

Arg Phe Arg Thr Val Asn Ser Thr Ser Trp Met Glu Val Asn Phe Ala
        195                 200                 205

Lys Asn Arg Lys Asp Lys Asn Gln Thr Tyr Asn Leu Thr Gly Leu Gln
        210                 215                 220

Pro Phe Thr Glu Tyr Val Ile Ala Leu Arg Cys Ala Val Lys Glu Ser
225                 230                 235                 240

Lys Phe Trp Ser Asp Trp Ser Gln Glu Lys Met Gly Met Thr Glu Glu
                245                 250                 255
```

-continued

Glu Ala Pro Cys Gly Leu Glu Leu Trp Arg Val Leu Lys Pro Ala Glu
                260                 265                 270

Ala Asp Gly Arg Arg Pro Val Arg Leu Leu Trp Lys Lys Ala Arg Gly
            275                 280                 285

Ala Pro Val Leu Glu Lys Thr Leu Gly Tyr Asn Ile Trp Tyr Tyr Pro
        290                 295                 300

Glu Ser Asn Thr Asn Leu Thr Glu Thr Met Asn Thr Thr Asn Gln Gln
305                 310                 315                 320

Leu Glu Leu His Leu Gly Gly Glu Ser Phe Trp Val Ser Met Ile Ser
                325                 330                 335

Tyr Asn Ser Leu Gly Lys Ser Pro Val Ala Thr Leu Arg Ile Pro Ala
            340                 345                 350

Ile Gln Glu Lys Ser Phe Gln Cys Ile Glu Val Met Gln Ala Cys Val
        355                 360                 365

Ala Glu Asp Gln Leu Val Val Lys Trp Gln Ser Ser Ala Leu Asp Val
    370                 375                 380

Asn Thr Trp Met Ile Glu Trp Phe Pro Asp Val Asp Ser Glu Pro Thr
385                 390                 395                 400

Thr Leu Ser Trp Glu Ser Val Ser Gln Ala Thr Asn Trp Thr Ile Gln
                405                 410                 415

Gln Asp Lys Leu Lys Pro Phe Trp Cys Tyr Asn Ile Ser Val Tyr Pro
            420                 425                 430

Met Leu His Asp Lys Val Gly Glu Pro Tyr Ser Ile Gln Ala Tyr Ala
        435                 440                 445

Lys Glu Gly Val Pro Ser Glu Gly Pro Glu Thr Lys Val Glu Asn Ile
    450                 455                 460

Gly Val Lys Thr Val Thr Ile Thr Trp Lys Glu Ile Pro Lys Ser Glu
465                 470                 475                 480

Arg Lys Gly Ile Ile Cys Asn Tyr Thr Ile Phe Tyr Gln Ala Glu Gly
                485                 490                 495

Gly Lys Gly Phe Ser Lys Thr Val Asn Ser Ser Ile Leu Gln Tyr Gly
            500                 505                 510

Leu Glu Ser Leu Lys Arg Lys Thr Ser Tyr Ile Val Gln Val Met Ala
        515                 520                 525

Ser Thr Ser Ala Gly Gly Thr Asn Gly Thr Ser Ile Asn Phe Lys Thr
    530                 535                 540

Leu Ser Phe Ser Val Phe Glu Ile Ile Leu Ile Thr Ser Leu Ile Gly
545                 550                 555                 560

Gly Gly Leu Leu Ile Leu Ile Ile Leu Thr Val Ala Tyr Gly Leu Lys
                565                 570                 575

Lys Pro Asn Lys Leu Thr His Leu Cys Trp Pro Thr Val Pro Asn Pro
            580                 585                 590

Ala Glu Ser Ser Ile Ala Thr Trp His Gly Asp Asp Phe Lys Asp Lys
        595                 600                 605

Leu Asn Leu Lys Glu Ser Asp Asp Ser Val Asn Thr Glu Asp Arg Ile
    610                 615                 620

Leu Lys Pro Cys Ser Thr Pro Ser Asp Lys Leu Val Ile Asp Lys Leu
625                 630                 635                 640

Val Val Asn Phe Gly Asn Val Leu Gln Glu Ile Phe Thr Asp Glu Ala
                645                 650                 655

Arg Thr Gly Gln Glu Asn Asn Leu Gly Gly Glu Lys Asn Gly Tyr Val
            660                 665                 670

Thr Cys Pro Phe Arg Pro Asp Cys Pro Leu Gly Lys Ser Phe Glu Glu

```
                675                 680                 685
Leu Pro Val Ser Pro Glu Ile Pro Pro Arg Lys Ser Gln Tyr Leu Arg
            690                 695                 700

Ser Arg Met Pro Glu Gly Thr Arg Pro Glu Ala Lys Glu Gln Leu Leu
705                 710                 715                 720

Phe Ser Gly Gln Ser Leu Val Pro Asp His Leu Cys Glu Glu Gly Ala
                725                 730                 735

Pro Asn Pro Tyr Leu Lys Asn Ser Val Thr Ala Arg Glu Phe Leu Val
            740                 745                 750

Ser Glu Lys Leu Pro Glu His Thr Lys Gly Glu Val
        755                 760

<210> SEQ ID NO 12
<211> LENGTH: 447
<212> TYPE: PRT
<213> ORGANISM: Artificial sequence
<220> FEATURE:
<223> OTHER INFORMATION: An artificially synthesized peptide sequence

<400> SEQUENCE: 12

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Leu Ser Asn His
            20                  25                  30

Asp Met Thr Trp Val Arg Gln Ala Pro Gly Lys Gly Leu Glu Tyr Val
        35                  40                  45

Ser Ile Ile Asn Thr Tyr Gly Asn His Tyr Ala Asn Trp Ala Ser
50                  55                  60

Gly Arg Phe Thr Ile Ser Arg Asp Asn Ser Lys Asn Thr Val Tyr Leu
65                  70                  75                  80

Gln Ile Asp Ser Leu Arg Ala Glu Asp Thr Ala Thr Tyr Tyr Cys Ala
                85                  90                  95

Arg Glu Thr His His Gly Ser Ser Gly Ile Asp His Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
```

```
            275                 280                 285
Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro
        435                 440                 445

<210> SEQ ID NO 13
<211> LENGTH: 217
<212> TYPE: PRT
<213> ORGANISM: Artificial sequence
<220> FEATURE:
<223> OTHER INFORMATION: An artificially synthesized peptide sequence

<400> SEQUENCE: 13

Asp Ile Gln Met Thr Gln Ser Pro Ser Ser Val Ser Ala Ser Val Gly
1               5                   10                  15

Asp Arg Val Thr Ile Thr Cys Gln Ala Ser Glu Ser Ile Tyr Ser Gly
            20                  25                  30

Leu Ala Trp Tyr Gln Gln Lys Pro Gly Gln Pro Pro Lys Leu Leu Ile
        35                  40                  45

Tyr Asp His Ser Thr Leu Ala Ser Gly Val Pro Ser Arg Phe Ser Gly
    50                  55                  60

Ser Gly Ser Gly Thr Glu Tyr Ala Leu Thr Ile Ser Ser Leu Gln Pro
65                  70                  75                  80

Glu Asp Phe Ala Thr Tyr Tyr Cys Gln His Ala Asp Tyr Ala His His
                85                  90                  95

Ser Asp Asn Val Phe Gly Gly Gly Thr Lys Val Glu Ile Lys Arg Thr
            100                 105                 110

Val Ala Ala Pro Ser Val Phe Ile Phe Pro Pro Ser Asp Glu Gln Leu
        115                 120                 125

Lys Ser Gly Thr Ala Ser Val Val Cys Leu Leu Asn Asn Phe Tyr Pro
    130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
            180                 185                 190

Lys Val Tyr Ala Cys Glu Val Thr His Gln Gly Leu Ser Ser Pro Val
```

Thr Lys Ser Phe Asn Arg Gly Glu Cys
    210                 215

<210> SEQ ID NO 14
<211> LENGTH: 324
<212> TYPE: PRT
<213> ORGANISM: Artificial sequence
<220> FEATURE:
<223> OTHER INFORMATION: An artificially synthesized peptide sequence

<400> SEQUENCE: 14

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Ser Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser Gln Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Gln Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Glu Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro

<210> SEQ ID NO 15

```
<211> LENGTH: 326
<212> TYPE: PRT
<213> ORGANISM: Homo sapiens

<400> SEQUENCE: 15

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Gly Lys
                325
```

US 10,544,227 B2

PHARMACEUTICAL COMPOSITION FOR PREVENTION AND/OR TREATMENT OF ATOPIC DERMATITIS COMPRISING IL-31 ANTAGONIST AS ACTIVE INGREDIENT

CROSS-REFERENCE TO RELATED APPLICATIONS

This application is the National Stage of International Application Serial No. PCT/JP2016/061859, filed on Apr. 13, 2016, which claims the benefit of Japanese Application Serial Nos. 2015-082699, filed on Apr. 14, 2015, and 2016-041641, filed on Mar. 4, 2016.

TECHNICAL FIELD

In a non-limiting embodiment, the disclosure of the present invention relates to, for example, a pharmaceutical composition for prevention and/or treatment of atopic dermatitis comprising an IL-31 antagonist as an active ingredient.

BACKGROUND ART

Atopic dermatitis is known to be easily exacerbated by external stimuli such as perspiration, scratching, and friction, and the suppression or alleviation of pruritus has been the most important therapeutic goal. Atopic dermatitis is a disease with skin inflammation, rash, or eczema, and is a chronic skin disease characterized by itchiness (pruritus). While not intended to be bound by theory, it is believed that atopic dermatitis occurs when an individual with an allergic predisposition (atopic predisposition) susceptible to diseases such as bronchial asthma, allergic rhinitis, and allergic dermatitis is exposed to various stimuli. Although the mechanism of the onset of atopic dermatitis is not yet fully elucidated, it is believed to be important that Th2-associated cytokines (such as IL-4, IL-13, and IL-5) and chemical mediators (such as histamine and serotonin) be produced as a result of IgE crosslinking of Fcε receptors present on activated T cells, basophils, or mast cells, and activation caused thereby.

Therapeutic methods for atopic dermatitis that are already known include drug therapy using steroids, antihistamines, and other drugs, as well as PUVA therapy utilizing UVA (ultraviolet A) irradiation. The previous therapeutic methods, however, require taking a medicine or applying a medicine to an affected area several times every day, with the potential problem of forgetting to take or apply the medicine. Moreover, ultraviolet therapy may require a visit to the hospital as many as once or twice a week, with the potential problem of placing a burden of visiting the hospital on the patient.

Furthermore, it has been reported that the development of itchiness associated with a disease such as atopic dermatitis is not due to the release of histamine and the like only (Non Patent Literature 1). Therefore, the development of a therapeutic agent for atopic dermatitis based on a novel mechanism of action has been anticipated.

IL-31 (interleukin-31) is a T-cell cytokine. It is known that dermatitis-like symptoms similar to pruritus or atopic dermatitis occur in transgenic mice overexpressing IL-31 (Non Patent Literature 2). It has also been found that the receptor to which IL-31 binds is a heterodimer of IL-31RA (interleukin-31 receptor A) and OSMR (oncostatin M receptor) (Patent Literature 1), and IL-31 transduces signals into cells through this receptor. It has been reported that the expression of human IL-31RA is elevated in the thickened epidermis of patients with atopic dermatitis (Non Patent Literature 3).

It has previously been reported that atopic dermatitis or pruritus caused by atopic dermatitis was tried to be improved or successfully improved using an IL-31 antagonist. Moreover, IL-31 neutralizing antibodies and IL-31RA neutralizing antibodies as IL-31 antagonists have been reported (Patent Literatures 2 to 16). However, while there are reports that the expression level of IL-31 protein or RNA is increased in the serum of patients with atopic dermatitis (Non Patent Literatures 4 and 5), there is also a report that no difference in the expression level of IL-31 is observed between the skin of patients with atopic dermatitis and the skin of healthy adults (Patent Literature 8).

CITATION LIST

Patent Literature

Patent Literature 1: WO 2004/003140
Patent Literature 2: WO 2005/079566
Patent Literature 3: WO 2006/063864
Patent Literature 4: WO 2006/063865
Patent Literature 5: WO 2009/071696
Patent Literature 6: WO 2006/088855
Patent Literature 7: WO 2006/088955
Patent Literature 8: WO 2006/088956
Patent Literature 9: WO 2007/133816
Patent Literature 10: WO 2007/142325
Patent Literature 11: WO 2009/072598
Patent Literature 12: WO 2006/122079
Patent Literature 13: WO 2007/143231
Patent Literature 14: WO 2008/028192
Patent Literature 15: WO 2009/072604
Patent Literature 16: WO 2010/064697

Non Patent Literature

Non Patent Literature 1: J Dermatol Sci (2001) 25, 20-28
Non Patent Literature 2: Nat Immunol (2004) 5, 752-760
Non Patent Literature 3: J Allergy Clin Immunol (2006) 117, 418-425
Non Patent Literature 4: J Allergy Clin Immunol (2008) 122, 421-423
Non Patent Literature 5: Ann Dermatol (2011) 23, 468-473

SUMMARY OF INVENTION

Technical Problem

In a non-limiting embodiment, an objective of the present disclosure is to provide, for example, a pharmaceutical composition for prevention and/or treatment of atopic dermatitis based on a more effective dosing regimen (dosing schedule).

Solution to Problem

In a non-limiting embodiment, the present inventors have previously developed pharmaceutical compositions for prevention and/or treatment of atopic dermatitis based on a novel mechanism of action; however, without being content with those results, the inventors have continued diligent research and development for long years to pursue a more effective dosing regimen that can alleviate the patient's burden of taking a medicine or visiting the hospital, for example, and can further contribute to improving the patient's QOL.

As a result, the present inventors surprisingly found a more effective dosing regimen that has been impossible to achieve with conventional therapeutic methods for atopic dermatitis.

In a non-limiting embodiment, the present disclosure relates to the following:

[1] A pharmaceutical composition for prevention and/or treatment of atopic dermatitis comprising an IL-31 antagonist as an active ingredient, wherein
the IL-31 antagonist is repeatedly administered in equal amounts at the same dosing interval to a subject with or potentially with atopic dermatitis, at 0.1 to 1000 mg/body/2 weeks, 0.1 to 1000 mg/body/4 weeks, or 0.1 to 1000 mg/body/8 weeks.

[2] The pharmaceutical composition according to [1], wherein the IL-31 antagonist is administered at 25 to 100 mg/body/4 weeks.

[3] The pharmaceutical composition according to [1] or [2], wherein the IL-31 antagonist is administered at 50 to 100 mg/body/4 weeks.

[4] A pharmaceutical composition for prevention and/or treatment of atopic dermatitis comprising an IL-31 antagonist as an active ingredient, wherein
the IL-31 antagonist is repeatedly administered in equal amounts at the same dosing interval to a subject with or potentially with atopic dermatitis, at 0.01 to 10 mg/kg/2 weeks, 0.01 to 10 mg/kg/4 weeks, or 0.01 to 10 mg/kg/8 weeks.

[5] The pharmaceutical composition according to [4], wherein the IL-31 antagonist is administered at 0.2 to 2 mg/kg/4 weeks.

[6] The pharmaceutical composition according to [4] or [5], wherein the IL-31 antagonist is administered at 0.5 mg/kg/4 weeks.

[7] The pharmaceutical composition according to any one of [1] to [6], for use in the prevention and/or treatment of pruritus due to atopic dermatitis.

[8] The pharmaceutical composition according to [7], for use in the improvement of sleep disturbance caused by the pruritus.

[9] The pharmaceutical composition according to [8], wherein the improvement of sleep disturbance is for increasing the time from falling asleep to awakening, and/or for decreasing sleep onset latency (the time from going to bed to falling asleep).

[10] The pharmaceutical composition according to any one of [1] to [9], wherein the IL-31 antagonist is an antibody that inhibits IL-31 signaling.

[11] The pharmaceutical composition according to [10], wherein the antibody comprises an amino acid variant of an H chain constant region sequence of IgG2, and the amino acid variant comprises glutamic acid at position 419 (EU numbering) in an H chain constant region sequence (SEQ ID NO: 15) of naturally occurring IgG2, wherein
the antibody exhibits an increased plasma half-life, compared to a reference antibody comprising an H chain constant region sequence of naturally occurring IgG2 having the same amino acid sequence except for the amino acid variation at position 419.

[12] The pharmaceutical composition according to [11], wherein the antibody exhibits a plasma half-life increased by a decrease in isoelectric point (pI) induced by the amino acid substitution with glutamic acid at position 419.

[13] The pharmaceutical composition according to [11] or [12], for providing an increased plasma half-life, compared to a pharmaceutical composition comprising the reference antibody comprising an H chain constant region sequence of naturally occurring IgG2 that is identical except for the amino acid variation at position 419.

[14] The pharmaceutical composition according to any one of [10] to [13], wherein the antibody does not exhibit cross-reactivity with IL-31RA of any of mouse, rat, and rabbit.

[15] The pharmaceutical composition according to any one of [10] to [14], wherein the antibody is an anti-IL-31 neutralizing antibody or an anti-IL-31RA neutralizing antibody.

[16] The pharmaceutical composition according to [15], wherein the anti-IL-31RA neutralizing antibody is any of:

(1) an anti-IL-31RA antibody comprising an H chain variable region comprising CDR1 as set forth in SEQ ID NO: 1, CDR2 as set forth in SEQ ID NO: 2, and CDR3 as set forth in SEQ ID NO: 3, and an L chain variable region comprising CDR1 as set forth in SEQ ID NO: 4, CDR2 as set forth in SEQ ID NO: 5, and CDR3 as set forth in SEQ ID NO: 6;

(2) an anti-IL-31RA antibody comprising an H chain variable region as set forth in SEQ ID NO: 7 and an L chain variable region as set forth in SEQ ID NO: 8; and (3) an anti-IL-31RA antibody comprising an H chain as set forth in SEQ ID NO: 9 and an L chain as set forth in SEQ ID NO: 10.

[17] The pharmaceutical composition according to any one of [1] to [16], for use in suppressing at least one symptom caused by atopic dermatitis selected from the group consisting of redness, induration, papules, edema, excoriations, and lichenification.

[18] The pharmaceutical composition according to any one of [1] to [17], wherein the atopic dermatitis is moderate or severe atopic dermatitis, for which topical therapy is not sufficiently effective or is intolerable.

[19] The pharmaceutical composition according to [18], wherein the topical therapy is a therapy using a topical steroid or a topical calcineurin inhibitor.

[20] The pharmaceutical composition according to any one of [1] to [19], wherein the IL-31 antagonist is subcutaneously administered.

[21] The pharmaceutical composition according to any one of [1] to [20], wherein the atopic dermatitis is atopic dermatitis caused by IL-31 signaling.

[22] The pharmaceutical composition according to any one of [1] to [21] for use in combination with a topical steroid or a topical calcineurin inhibitor, wherein the IL-31 antagonist is administered before, simultaneously with, or after administration (application) of the topical steroid or the topical calcineurin inhibitor.

[23] The pharmaceutical composition according to [22], wherein the IL-31 antagonist and the topical steroid or the topical calcineurin inhibitor are sequentially or simultaneously administered.

[24] The pharmaceutical composition according to [22] or [23], wherein the administration of the topical steroid or the topical calcineurin inhibitor in combination with the IL-31 antagonist can reduce the dosage (applied amount) of the topical steroid or the topical calcineurin inhibitor when used in combination, compared to the dosage of the topical steroid or the topical calcineurin inhibitor when continuously administered (applied) as a single agent.

[25] A combination of the pharmaceutical composition according to any one of [1] to [21] and a topical steroid or a topical calcineurin inhibitor.

[26] A method for preventing and/or treating atopic dermatitis comprising administering an IL-31 antagonist to a subject with or potentially with atopic dermatitis, wherein the IL-31 antagonist is repeatedly administered in equal amounts at the same dosing interval to the subject with or potentially with atopic dermatitis, at 0.1 to 1000 mg/body/2 weeks, 0.1 to 1000 mg/body/4 weeks, or 0.1 to 1000 mg/body/8 weeks.

[27] A method for preventing and/or treating atopic dermatitis comprising administering an IL-31 antagonist to a subject with or potentially with atopic dermatitis, wherein the IL-31 antagonist is repeatedly administered in equal amounts at the same dosing interval to a subject with or potentially with atopic dermatitis, at 0.01 to 10 mg/kg/2 weeks, 0.01 to 10 mg/kg/4 weeks, or 0.01 to 10 mg/kg/8 weeks.

[28] Use of an IL-31 antagonist for the manufacture of a medicament for prevention and/or treatment of atopic dermatitis, wherein the IL-31 antagonist is repeatedly administered in equal amounts at the same dosing interval to a subject with or potentially with atopic dermatitis, at 0.1 to 1000 mg/body/2 weeks, 0.1 to 1000 mg/body/4 weeks, or 0.1 to 1000 mg/body/8 weeks.

[29] Use of an IL-31 antagonist for the manufacture of a medicament for prevention and/or treatment of atopic dermatitis, wherein the IL-31 antagonist is repeatedly administered in equal amounts at the same dosing interval to a subject with or potentially with atopic dermatitis, at 0.01 to 10 mg/kg/2 weeks, 0.01 to 10 mg/kg/4 weeks, or 0.01 to 10 mg/kg/8 weeks.

[30] A product comprising (i) a container; (ii) a pharmaceutical composition comprising an IL-31 antagonist as an active ingredient within the container; and (iii) a document instructing that the IL-31 antagonist be repeatedly administered in equal amounts at the same dosing interval to a subject with or potentially with atopic dermatitis, at 0.1 to 1000 mg/body/2 weeks, 0.1 to 1000 mg/body/4 weeks, or 0.1 to 1000 mg/body/8 weeks.

[31] A product comprising (i) a container; (ii) a pharmaceutical composition comprising an IL-31 antagonist as an active ingredient within the container; and (iii) a document instructing that the IL-31 antagonist be repeatedly administered in equal amounts at the same dosing interval to a subject with or potentially with atopic dermatitis, at 0.01 to 10 mg/kg/2 weeks, 0.01 to 10 mg/kg/4 weeks, or 0.01 to 10 mg/kg/8 weeks.

[32] A pharmaceutical composition for use in the prevention and/or treatment of atopic dermatitis comprising an IL-31 antagonist as an active ingredient, which is further for use in the improvement of sleep disturbance caused by atopic dermatitis.

[33] The pharmaceutical composition according to [32], wherein the sleep disturbance is caused by pruritus due to atopic dermatitis.

[34] The pharmaceutical composition according to [32] or [33], wherein the improvement of sleep disturbance is for increasing the time from falling asleep to awakening, and/or for decreasing sleep onset latency (the time from going to bed to falling asleep).

[35] An IL-31 antagonist used for prevention and/or treatment of atopic dermatitis, which is repeatedly administered in equal amounts at the same dosing interval to a subject with or potentially with atopic dermatitis, at 0.1 to 1000 mg/body/1 day to 12 weeks, preferably at 0.1 to 1000 mg/body/2 weeks, 0.1 to 1000 mg/body/4 weeks, or 0.1 to 1000 mg/body/8 weeks.

[36] An IL-31 antagonist used for prevention and/or treatment of atopic dermatitis, which is repeatedly administered in equal amounts at the same dosing interval to a subject with or potentially with atopic dermatitis, at 0.01 to 10 mg/kg/1 day to 12 weeks, preferably at 0.01 to 10 mg/kg/2 weeks, 0.01 to 10 mg/kg/4 weeks, or 0.01 to 10 mg/kg/8 weeks.

Any combinations of some or all of the one or more elements recited in any of [1] to [36] above are also included in the present disclosure, unless they are technically inconsistent based on common knowledge in the art, and are contradictory in the context.

Naturally, therefore, a person skilled in the art can directly and unambiguously conceive of various embodiments such as, for example, "an IL-31 antagonist used for prevention and/or treatment of atopic dermatitis, which is repeatedly administered in equal amounts at the same dosing interval to a subject with or potentially with atopic dermatitis, at 25 to 100 mg/body/4 weeks or 0.2 to 2 mg/kg/4 weeks, wherein the atopic dermatitis is moderate or severe atopic dermatitis, for which a therapy using a topical steroid or a topical calcineurin inhibitor is not sufficiently effective or is intolerable".

DESCRIPTION OF EMBODIMENTS

Figure 1:
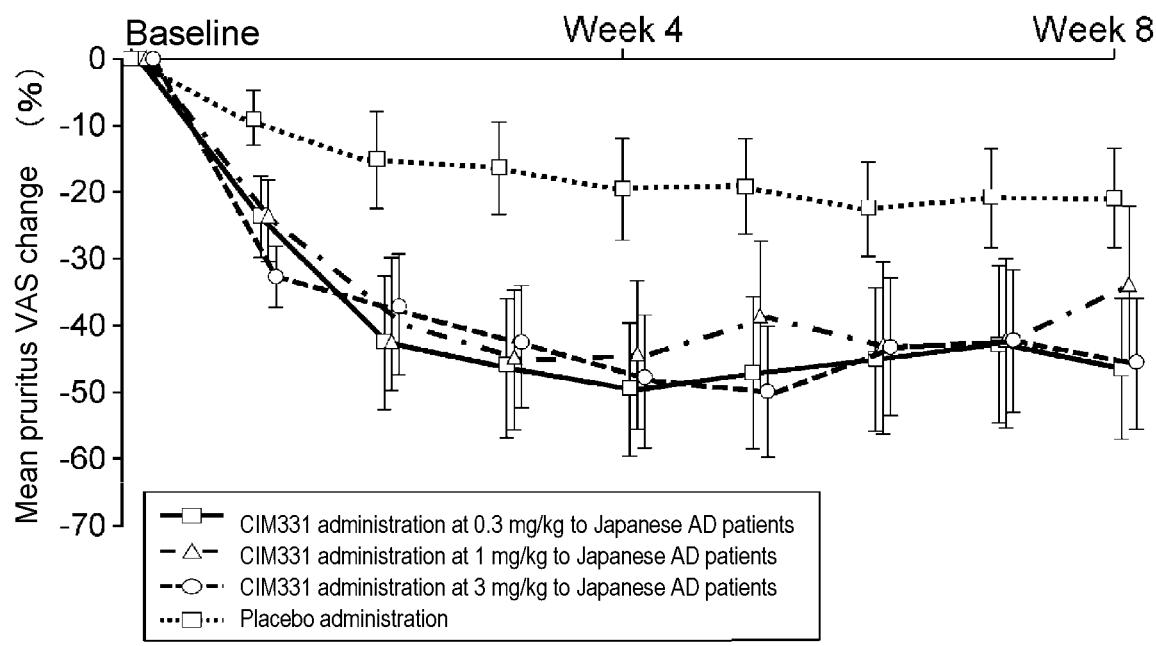
FIG. 1 is a graph showing the effects of suppressing pruritus based on the VAS, after the administration of single subcutaneous doses of CIM331 or placebo to predetermined patients with atopic dermatitis (AD).

Preferred non-limiting embodiments of the present disclosure will be hereinafter described.

All the embodiments set forth in the Examples below are described with the intention that they are naturally construed as being equivalently described in the "Description of Embodiments" of the present specification, without being restricted by any patent practice, conventions, or law that may interpret the contents of the Examples in a limiting manner, in a country where it is intended that the protection of the present patent application be sought.

IL-31 (interleukin-31) is a T-cell cytokine. It is known that IL-31 is involved in pruritus, and in transgenic mice overexpressing IL-31, dermatitis-like symptoms similar to atopic dermatitis occur, and persistent scratching behavior is observed.

The nucleic acid sequence and amino acid sequence of human IL-31 are also known as RefSeq accession number NM_001014336 and RefSeq accession number NP_001014358, respectively.

The receptor for IL-31 is formed of a heterodimer of IL-31 receptor A (IL-3 IRA) and oncostatin M receptor (OSMR) (Nat Immunol (2004) 5, 752-60). IL-31RA, also referred to as NR10, is known to have a plurality of splicing variants (WO 00/075314). Among known splicing variants are NR10.1 (652 amino acids), NR10.2 (252 amino acids), NR10.3 (662 amino acids, also referred to as IL-31RAv4), and IL-31RAv3 (764 amino acids), and examples of preferred IL-31RA include NR10.3 (IL-31RAv4) and IL-31RAv3. The nucleic acid sequence and amino acid sequence of human IL-31RA (IL-31RAv4) are also known as RefSeq accession number NM_001242638 and RefSeq accession number NP_001229567, respectively. The nucleic acid sequence and the amino acid sequence of human IL-31RA (IL-31RAv3) are also known as RefSeq accession number NM_139017 and RefSeq accession number NP_620586, respectively. The nucleic acid sequence and the amino acid sequence of human OSMR are also known as RefSeq accession number NM_003999 and RefSeq accession number NP_003990, respectively.

As used herein, the IL-31 antagonist of the present disclosure, in one embodiment, refers to a compound that suppresses or blocks IL-31-induced intracellular signaling. This compound can also be expressed as a compound that inhibits IL-31 signaling. Such a compound may be a naturally occurring compound or an artificially synthesized compound. Moreover, such a compound may be a low-molecular-weight compound or a high-molecular-weight compound such as a protein.

It is known that IL-31 that is present extracellularly triggers intracellular signaling via the IL-31 receptor (heterodimer of IL-31RA and OSMR) present on the cell surface (Nat Immunol (2004) 5, 752-760). The extracellular domain of the IL-31 receptor includes an IL-31-binding domain, and binding of IL-31 thereto causes a change in the conformation of the IL-31 receptor. As a result, intracellular signaling is initiated from the intracellular domain of the IL-31 receptor.

In one method, whether a certain compound inhibits IL-31 signaling can be verified by examining whether the compound inhibits binding of IL-31 to the IL-31 receptor. Examples of methods for making such a determination include an assay using ELISA or flow cytometry and an assay using surface plasmon resonance. With ELISA, for example, whether the compound inhibits the binding of IL-31 to the IL-31 receptor can be evaluated by immobilizing the IL-31 receptor (or IL-31RA) protein onto a plate, preparing a system for detecting the amount of IL-31 protein that binds thereto through the use of a secondary antibody such as an enzyme-labeled anti-IL-31 antibody, and determining whether or not the addition of the compound reduces the amount of detected IL-31 protein.

In an alternative method, whether a certain compound inhibits IL-31 signaling can be verified by examining whether the bioactivity induced by the action of IL-31 on cells is inhibited by the compound. The bioactivity is not particularly limited as long as it can be quantitatively or qualitatively determined using any method, and examples of such bioactivities include cell proliferative activity, protein phosphorylation activity, and gene/protein expression-inducing activity. For example, whether the compound inhibits IL-31 signaling can be evaluated by preparing cells that express the IL-31 receptor on the surface, and whose proliferative activity is induced in response to external IL-31 stimulation, and determining whether or not the addition of the compound reduces the IL-31-induced cell proliferative activity. As such cells, naturally occurring cells inherently expressing the IL-31 receptor may be used, or recombinant cells artificially synthesized to express the IL-31 receptor may be used. A suitable example of recombinant cells includes Ba/F3 cells expressing the IL-31 receptor. As a further alternative, the method described in the document of Dillon et al. (Nat Immunol (2004) 5, 752-760) may be used.

In the present disclosure, the degree of inhibition of IL-31 signaling by the IL-31 antagonist may be, but not limited to, at least 10% or more, preferably 20% or more, 30% or more, 40% or more, 50% or more, 60% or more, 70% or more, and 80% or more, and particularly preferably 90% or more, 95% or more, and 98% or more.

In the present disclosure, a preferred embodiment of the compound that inhibits IL-31 signaling includes a protein that inhibits IL-31 signaling. The protein used herein is not particularly limited as long as it has the property of specifically binding to IL-31 or the IL-31 receptor. Examples of preferred proteins include antibodies and antibody-like molecules (Curr Opin Biotechnol (2006) 17, 653-658; Curr Opin Struct Biol (1997) 7, 463-469; and Protein Sci (2006) 15, 14-27). Antibodies include any antibodies such as monoclonal antibodies (e.g., IgG, IgM, IgE, IgA, and IgD), polyclonal antibodies, engineered antibodies (e.g., chimeric antibodies, humanized antibodies, and glycoengineered antibodies (WO 99/54342 and WO 00/61739)), antibody fragments (e.g., Fab, F(ab')2, Fv, and CDR), multi-specific antibodies (e.g., bispecific antibodies), and conjugated antibodies (e.g., antibodies conjugated with polyethylene glycol (PEG), radioactive isotopes, or drugs). On the other hand, examples of antibody-like molecules include DARPin (WO 2002/020565), Affibody (WO 1995/001937), Avimer (WO 2004/044011), and Adnectin (WO 2002/032925). More preferred is an antibody that inhibits IL-31 signaling. Examples of other preferred proteins that inhibit IL-31 signaling include a protein containing the extracellular domain of IL-31RA and a protein containing each extracellular domain of the IL-31 receptor (heterodimer of IL-31RA and OSMR).

In the present disclosure, preferred embodiments of the antibody that inhibits IL-31 signaling include an antibody that inhibits IL-31 signaling by binding to IL-31 (anti-IL-31 neutralizing antibody) and an antibody that inhibits IL-31 signaling by binding to the IL-31 receptor (anti-IL-31 receptor neutralizing antibody). Anti-IL-31 receptor neutralizing antibodies include an antibody that inhibits IL-31 signaling by binding to IL-31RA (anti-IL-31RA neutralizing antibody), an antibody that inhibits IL-31 signaling by binding to OSMR (anti-OSMR neutralizing antibody), and an antibody that inhibits IL-31 signaling by binding to the heterodimer of IL-31RA and OSMR (anti-IL-31RA/OSMR heterodimer neutralizing antibody). Of these anti-IL-31 receptor neutralizing antibodies, preferred is an anti-IL-31RA neutralizing antibody or anti-IL-31RA/OSMR heterodimer neutralizing antibody, and more preferred is an anti-IL-31RA neutralizing antibody.

The antibody that inhibits IL-31 signaling of the present disclosure in a further embodiment or another embodiment preferably comprises an amino acid variant of an H chain constant region sequence of IgG2, where the amino acid variant comprises glutamic acid at position 419 (EU numbering) in the H chain constant region sequence (SEQ ID NO: 15) of naturally occurring IgG2. This engineered antibody is advantageous in that it exhibits an increased plasma half-life, compared to a reference antibody comprising an H chain constant region sequence of naturally occurring IgG2 having the same amino acid sequence except for the amino acid variation at position 419. It is thought that such an increased plasma half-life was caused by a decrease in isoelectric point (pI) induced by the amino acid substitution with glutamic acid at position 419 (Example 2).

Thus, the pharmaceutical composition of the present disclosure in one embodiment is advantageous in that it relates to a pharmaceutical composition for providing an increased plasma half-life, compared to a (reference) pharmaceutical composition comprising a reference antibody comprising an H chain constant region sequence of naturally occurring IgG2 having the same amino acid sequence except for the amino acid variation at position 419.

In this case, the antibody that inhibits IL-31 signaling of the present disclosure in a preferred embodiment is any of the following anti-IL-31RA neutralizing antibodies:

(1) an anti-IL-31RA antibody comprising an H chain variable region comprising CDR1 as set forth in SEQ ID NO: 1, CDR2 as set forth in SEQ ID NO: 2, and CDR3 as set forth in SEQ ID NO: 3, and an L chain variable region comprising CDR1 as set forth in SEQ ID NO: 4, CDR2 as set forth in SEQ ID NO: 5, and CDR3 as set forth in SEQ ID NO: 6;

(2) an anti-IL-31RA antibody comprising an H chain variable region as set forth in SEQ ID NO: 7 and an L chain variable region as set forth in SEQ ID NO: 8; and (3) an anti-IL-31RA antibody comprising an H chain as set forth in SEQ ID NO: 9 and an L chain as set forth in SEQ ID NO: 10.

It is understood that isoelectric point (pI), also simply referred to as "pI", may be either a theoretical isoelectric point or an experimentally measured isoelectric point, where it is not expressly described in the present specification, and unless it is contradictory in the context.

For example, the value of isoelectric point can be measured by isoelectric focusing known to those skilled in the art. The value of theoretical isoelectric point can be calculated using gene and amino acid sequence analysis software (e.g., Genetyx). Alternatively, the value of theoretical isoelectric point can be measured by performing a pharmacokinetic study of the antibody using, for example, the plasma of mice, rats, rabbits, dogs, monkeys, humans, or the like, in combination with a method known to those skilled in the art such as BIACORE, cell proliferation assay, ELISA, EIA (enzyme immunoassay), RIA (radioimmunoassay), or immunofluorescence.

Whether the plasma half-life of the antibody has changed before and after the amino acid variation (modification) may be verified by performing a pharmacokinetic study of the antibody using a method known to those skilled in the art, using, for example, the plasma of mice, rats, rabbits, dogs, monkeys, humans, or the like.

The antibody that inhibits IL-31 signaling of the present disclosure, in a still further embodiment or another embodiment, preferably does not (substantially) exhibit cross-reactivity with IL-31RA from any of mouse, rat, and rabbit, although it has cross-reactivity with IL-31RA from humans and cynomolgus monkeys.

Methods for preparing antibodies are well known to those skilled in the art, and antibodies can be prepared using the hybridoma method (Nature (1975) 256, 495) or the phage antibody library method (Nature (1991) 352, 624-628, J Mol Biol (1991) 222, 581-597), for example. Using the IL-31 protein or IL-31 receptor protein as an antigen, a large number of anti-IL-31 antibodies or anti-IL-31 receptor antibodies can be obtained by these methods. Furthermore, screening of these antibodies using any of the above-described methods for detecting the compound that inhibits IL-31 signaling allows an anti-IL-31 neutralizing antibody or an anti-IL-31 receptor neutralizing antibody to be obtained. A protein such as IL-31 or the IL-31 receptor may also be prepared using a genetic engineering technology known to those skilled in the art. Specifically, such a protein can be prepared by inserting a gene encoding a desired protein into an expression vector, introducing the vector into an appropriate host cell, and then purifying the target protein expressed in the host cell or in the culture supernatant of the host cell.

Examples of preferred anti-IL-31 neutralizing antibodies include the anti-IL-31 antibodies described in WO 2006/122079, WO 2008/028192, and WO 2009/071696.

Examples of preferred anti-IL-31RA neutralizing antibodies include, but are not limited to, the anti-IL-31RA (NR10) antibody described in WO 2007/142325, the anti-IL-31RA (NR10) antibody described in WO 2009/072604, and the anti-IL-31RA (NR10) antibody described in WO 2010/064697.

Moreover, examples of other preferred anti-IL-31RA neutralizing antibodies include anti-human IL-31RA (neutralizing) antibodies, specifically including an anti-IL-31RA (neutralizing) antibody that recognizes domain 1 and/or domain 2 of human IL-31RA. As used herein, domain 1 of human IL-31RA designates the region from amino acid at position 53 to amino acid at position 152 (LPAKP to LENIA) in the amino acid sequence as set forth in SEQ ID NO: 11. Domain 2 designates the region from amino acid at position 153 to amino acid at position 259 (KTEPP to EEEAP) in the amino acid sequence as set forth in SEQ ID NO: 11.

Without any limitation, of the anti-IL-31RA neutralizing antibodies, more preferred is the anti-IL-31RA antibody described in WO 2010/064697 comprising an H chain (heavy chain) variable region comprising CDR1 as set forth in SEQ ID NO: 1, CDR2 as set forth in SEQ ID NO: 2, and CDR3 as set forth in SEQ ID NO: 3, and an L chain variable region comprising CDR1 as set forth in SEQ ID NO: 4, CDR2 as set forth in SEQ ID NO: 5, and CDR3 as set forth in SEQ ID NO: 6. More preferred is an anti-IL-31RA antibody comprising an H chain variable region as set forth in SEQ ID NO: 7 and an L chain (light chain) variable region as set forth in SEQ ID NO: 8. Particularly preferred is an anti-IL-31RA antibody comprising an H chain as set forth in SEQ ID NO: 9 and an L chain as set forth in SEQ ID NO: 10.

Known methods for defining CDRs include the method according to Kabat et al. (Sequences of Proteins of Immunological Interest, 5th Ed (1991), Bethesda, Md.), the method according to Chothia et al. (Science (1986) 233, 755-758), and the method based on antigen-antibody contact regions (J Mol Biol (1996) 262, 732-745). Specifically, each of the methods defines CDRs as follows:

| CDR | Kabat | Chothia | Contact |
|-----|-------|---------|---------|
| L1 | L24-L34 | L24-L34 | L30-L36 |
| L2 | L50-L56 | L50-L56 | L46-L55 |
| L3 | L89-L97 | L89-L97 | L89-L96 |
| H1 | H31-H35B | H26-H32/34 | H30-H35B (Kabat numbering) |
| H1 | H31-H35 | H26-H32 | H30-H35 (Chothia numbering) |
| H2 | H50-H65 | H52-H56 | H47-H58 |
| H3 | H95-H102 | H95-H102 | H93-H101 |

An example of a preferred anti-IL-31RA neutralizing antibody of the present disclosure includes an anti-IL-31RA antibody comprising CDR1, CDR2, and CDR3 contained in the H chain variable region as set forth in SEQ ID NO: 7, and CDR1, CDR2, and CDR3 contained in the L chain variable region as set forth in SEQ ID NO: 8, as H chain CDR1, CDR2, and CDR3, and L chain CDR1, CDR2, and CDR3, respectively. The CDRs in such an antibody may be defined in accordance with any of the method according to Kabat et al., the method according to Chothia et al., and the method based on antigen-antibody contact regions, or in accordance with a combination of these methods.

Similarly, preferred as the anti-IL-31RA neutralizing antibody is an anti-IL-31RA antibody that binds to the same epitope as that of the anti-IL-31RA antibody defined by the above-described sequences of CDRs of the H chain and L chain, H chain and L chain variable region sequences, and full-length H chain and L chain sequences. An epitope refers to a specific structural unit of an antigen to which an antibody recognizes and binds. When the antigen is a polypeptide, the epitope typically consists of about 6 to 10 amino acids. Epitope identification can be performed using a method known to those skilled in the art, for example, a method of synthesizing peptides by fragmentation of the antigen, a method of introducing site-directed mutagenesis into the antigen (e.g., arginine/glutamic acid scanning, J Biol Chem (1995) 270, 21619-21625, J Biol Chem (2006) 281, 20464-20473), and a method of crystallizing an antigen-antibody complex (Using Antibodies: A Laboratory Manual (1999), Cold Spring Harbor Laboratory Press, New York). In the present disclosure, the recitation "binds to the same epitope" means that the epitopes to which two antibodies bind at least partially overlap each other. The degree of the overlap is, but not limited to, at least 10% or more, preferably 20% or more, 30% or more, 40% or more, 50% or more, 60% or more, 70% or more, and 80% or more, particularly 90% or more, and most preferably 100%.

Similarly, preferred as the anti-IL-31RA neutralizing antibody is an anti-IL-31RA antibody that competes for binding to IL-31RA with the anti-IL-31RA antibody defined by the above-described sequences of CDRs of the H chain and L chain, H chain and L chain variable region sequences, and full-length H chain and L chain sequences. Whether the two antibodies compete with each other can be evaluated by using a competition binding assay utilizing ELISA, for example. A specific method is as follows: One of the two antibodies is pre-labeled with, for example, fluorescence. A system for detecting the binding of the antibody (labeled antibody) to the antigen is prepared. A comparison is made between the case where the other unlabeled antibody (test antibody) coexists and the case where the test antibody does not coexist in the system. If the level of binding of the labeled antibody to the antigen is decreased in the presence of the test antibody, it can be judged that the test antibody and the labeled antibody compete with each other. In the present disclosure, the degree of competition is, but not particularly limited to, at least 10% or more, preferably 20% or more, 30% or more, 40% or more, 50% or more, 60% or more, 70% or more, and 80% or more, and particularly preferably 90% or more, 95% or more, and 98% or more (that is, the level of binding of the other antibody is decreased).

A nucleotide sequence or amino acid sequence encoding the antibody that inhibits IL-31 signaling (e.g., the anti-IL-31 neutralizing antibody or the anti-IL-31RA neutralizing antibody) of the present disclosure can be obtained using a method known to those skilled in the art. Amino acids contained in the amino acid sequence of the antibody described in the present disclosure may undergo a post-translational modification (e.g., a modification involving the conversion of N-terminal glutamine to pyroglutamate by pyroglutamylation is well known to those skilled in the art). Even if the amino acids are thus post-translationally modified, the resulting amino acid sequence is naturally included in the amino acid sequences described in the present disclosure.

Atopic dermatitis in the present disclosure may preferably be atopic dermatitis caused by IL-31 signaling or induced by IL-31, or atopic dermatitis showing responsiveness to the prevention and/or treatment with the IL-31 antagonist, but not limited thereto.

Pruritus in the present disclosure may be atopic dermatitis-induced pruritus, and may preferably be pruritus due to atopic dermatitis caused by IL-31 signaling or induced by IL-31, but not limited thereto. Moreover, pruritus may be pruritus due to atopic dermatitis which shows responsiveness to the prevention and/or treatment with the IL-31 antagonist.

Atopic dermatitis may be moderate to severe atopic dermatitis, for example, and may preferably be moderate or severe atopic dermatitis for which topical therapy is not sufficiently effective or is intolerable, or standard topical therapy is not sufficiently effective or is intolerable, or standard topical therapy is prohibited (for reasons such as contraindications). More preferably, atopic dermatitis may be moderate or severe atopic dermatitis for which topical therapy is not sufficiently effective or is intolerable.

For topical therapy, topical steroids (e.g., glucocorticoids or their derivatives such as prednisolone and hydrocortisone) and topical calcineurin inhibitors known as immunosuppressants (e.g., tacrolimus and tacrolimus) are known, for example.

In addition to the topical steroids and topical calcineurin inhibitors, ciclosporin, methotrexate (MTX), or azathioprine (AZA), or antihistamines (various drugs are known as antihistaminic preparations, and are broadly classified into first-generation antihistamines and second-generation antihistamines) are known, for example, as therapeutic agents for atopic dermatitis.

More specifically, without any limitation, the following therapeutic methods are known for the treatment of atopic dermatitis ("Therapeutic Guidelines for Atopic Dermatitis", Furue et al., the Japanese journal of dermatology: 119 (8), pp. 1515-1534, 2009; "Guidelines of care for the management of atopic dermatitis: section 3. Management and treatment with phototherapy and systemic agents.", Sidbury R et al., J Am Acad Dermatol. (2014), pp. 327-337); and Saeki H, et al. J Dermatol 2009, 36, pp. 563-77).

(1) Ciclosporin Preparation (Brand Name: Neoral)

Typically, the ciclosporin preparation is orally administered to an adult at 3 mg/kg per day, calculated as ciclosporin, in two divided doses a day. The dose should not exceed 5 mg/kg per day, although it will vary as appropriate depending on the symptoms.

(2) Steroid Preparation for Oral Administration (Brand Name: Prednisolone Tablets)

Typically, the steroid preparation is orally administered to an adult at 5 to 60 mg per day, calculated as prednisolone (in the case of tablets, 1 to 12 tablets; in the case of powder, 0.5 to 6 g), in one to four divided doses. The dose will vary as appropriate depending on the age or symptoms.

(3) Ultraviolet Therapy

It is generally said that a patient needs to visit the hospital once or twice a week, although there is no established manual or guidelines.

(4) Antihistamine Preparation (Brand Name: Allegra)

Typically, the antihistamine preparation is orally administered to an adult at a single dose of 60 mg, calculated as fexofenadine hydrochloride, twice a day. Typically, the antihistamine preparation is orally administered to a child 7 years or older and younger than 12 years at a single dose of 30 mg, calculated as fexofenadine hydrochloride, twice a day, and is orally administered to a child 12 years or older at a single dose of 60 mg, calculated as fexofenadine hydrochloride, twice a day. The dose will vary as appropriate depending on the symptoms.

(5) Topical Steroid Preparation (Brand Name: Fulmeta)

Typically, an appropriate amount of the topical steroid preparation is applied to an affected area once to several times a day. The amount will vary as appropriate depending on the symptoms.

(6) Topical Steroid Preparation (Brand Name: Locoid)

Typically, an appropriate amount of the topical steroid preparation is applied once to several times a day. The amount will vary as appropriate depending on the symptoms.

(7) Tacrolimus Preparation (Brand Name: Protopic)

Typically, an appropriate amount of the tacrolimus preparation is applied to an affected area once or twice a day for an adult. The applied amount should be up to 5 g per application.

(8) Pimecrolimus Preparation (Brand Name: Elidel)

Typically, an appropriate amount of the pimecrolimus preparation is applied twice a day. The amount will vary as appropriate depending on the symptoms.

In one embodiment, the IL-31 antagonist (e.g., the anti-IL-31 neutralizing antibody or anti-IL-31RA neutralizing antibody) of the present disclosure may be administered in combination with the above-described existing therapeutic drug or therapeutic method. The IL-31 antagonist of the present disclosure may be administered in combination with a topical steroid or a topical calcineurin inhibitor, for example, and the IL-31 antagonist may be administered to a subject before, simultaneously with, or after administration (application) of the topical steroid or the topical calcineurin inhibitor. As will be discussed in detail in "(4-5) Effect of combined administration of CIM331 and a topical steroid or the like" below, when patients in which a sufficient dermatitis-improving effect was not demonstrated although a sufficient pruritus-improving effect was demonstrated through the administration of CIM331 in Part A period of a phase II repeated dose study, were administered with a topical steroid or the like in combination with CIM331 for a short period or a required period of time after the start of Part B period, a continuous and remarkable dermatitis-improving effect was surprisingly demonstrated.

Figure 4:
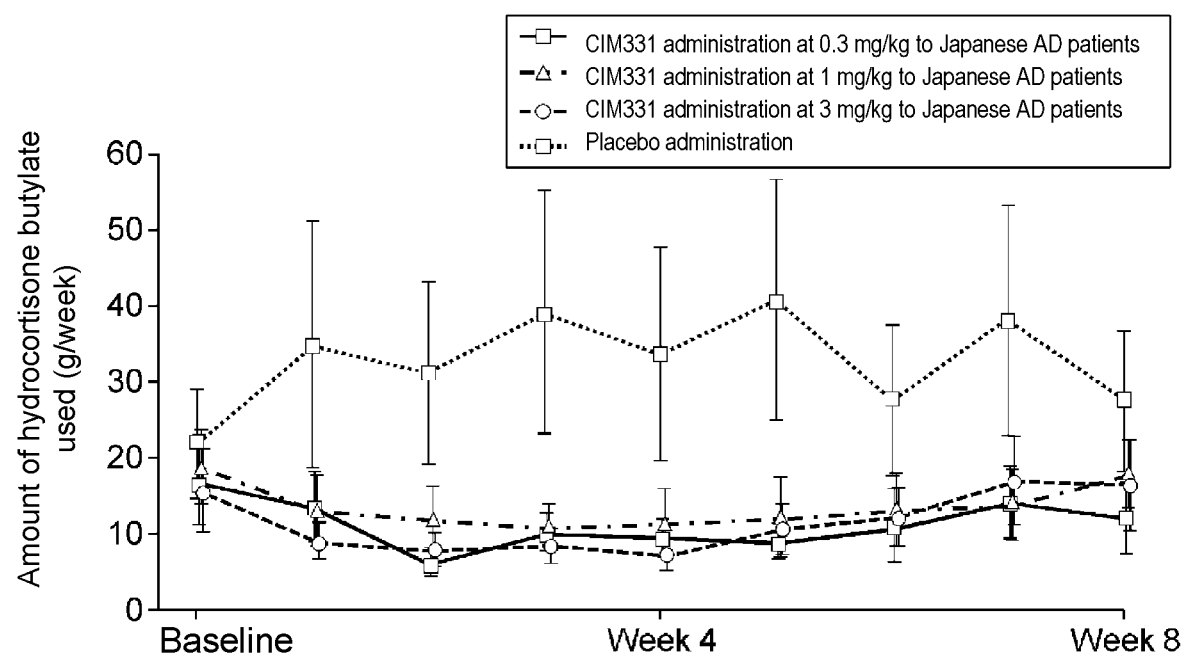
FIG. 4 is a graph showing the amounts of the topical steroid (Locoid) used after the administration of single subcutaneous doses of CIM331 or placebo to predetermined patients with atopic dermatitis.

When the IL-31 antagonist is administered in combination with the topical steroid or the topical calcineurin inhibitor, the order of administration, the timing of administration, and the frequency of administration of each agent are not particularly limited. The IL-31 antagonist of the present disclosure may be administered at equal continuous doses (which will be described below) and at an equal dosing interval between continuous doses (interval between doses). In a non-limiting preferred embodiment, the administration of the IL-31 antagonist of the present disclosure in combination with the topical steroid or topical calcineurin inhibitor can reduce the dose (applied amount) of the topical steroid or the topical calcineurin inhibitor, compared to the dose of the topical steroid or topical calcineurin inhibitor when continuously administered (applied) as a single agent (FIG. 4). The dose of the topical steroid or the topical calcineurin inhibitor may be reduced by 5%, 10%, 15%, 20%, 25%, 30%, 35%, 40%, 45%, 50%, 60%, 70%, 80%, 90%, 95%, 98%, or 100%, compared to the dose when continuously administered (applied) as a single agent, but not particularly limited thereto.

The topical steroid may be, but not limited thereto, hydrocortisone, desonide, or prednisolone, for example. The topical calcineurin inhibitor may be, but not limited thereto, pimecrolimus or tacrolimus, for example.

The severity (e.g., mild, moderate, or severe) of atopic dermatitis may be classified based on a classification method known to those skilled in the art for scoring the degree of rash or itchiness felt by the subject, such as Shiratori's severity criteria, the below-described Visual Analogue Scale (VAS), Verbal Rating Scale (VRS) for pruritus, SCORing Atopic Dermatitis (SCORAD) established by the European Task Force on Atopic Dermatitis, Eczema Area and Severity Index (EASI) established in the United States, or static Investigator's Global Assessment (sIGA), for example.

The VAS, for example, consists of a 100-mm straight line, on which the subject (patient) indicates the intensity of itchiness at the time of the measurement by drawing a line between 0 to 100 mm, where 0 mm represents no itchiness, and 100 mm represents the worst imaginable itchiness. For example, a subject determined to have a VAS score of 40 mm or more may be recognized as having moderate to severe atopic dermatitis, and in one embodiment, the VAS score may be 45 mm or more, or 50 mm or more. Likewise, in the case of the VRS, for example, a subject classified into the level of "moderate itchiness" or higher may be recognized as having moderate to severe atopic dermatitis (Reich et al. 2012). Alternatively, for example, a subject determined to have an EASI score of 10 or more, a sIGA score of 3 or more, or a total score of 4 or more in the evaluation of the degree of itchiness in the daytime or nighttime based on Shiratori's severity criteria may be recognized as having moderate to severe atopic dermatitis. Alternatively, a subject in which rash with intense inflammation affects, for example, 5% or more of the body surface area may be recognized as having moderate to severe atopic dermatitis. Alternatively, a subject in which one or a combination of a plurality of indices of those mentioned herein are satisfied, as appropriate, may be recognized as having moderate to severe atopic dermatitis.

As used herein, the "subject" may preferably be an animal, and more preferably a mammal (which may be a mouse, a rat, a rabbit, a dog, a monkey (e.g., a cynomolgus monkey), a human, or the like, and particularly preferably a human), but not limited thereto. The human may be an adult (18 years or older) or a child (0 to younger than 18 years, for example, 6 months to younger than 18 years).

In one embodiment, the present disclosure relates to a pharmaceutical composition for prevention and/or treatment of atopic dermatitis (the "pharmaceutical composition for prevention and/or treatment" may also be expressed as "a prophylactic agent and/or a therapeutic agent") comprising an IL-31 antagonist as an active ingredient.

In this case, the IL-31 antagonist may be intended to be repeatedly administered in equal amounts at the same dosing interval, using the predetermined dosing interval and the predetermined dose (dosage) that will be described in detail below.

In one embodiment, the pharmaceutical composition of the present disclosure may be used for prevention and/or treatment of pruritus due to topic dermatitis.

In a still further embodiment or another embodiment, the pharmaceutical composition of the present disclosure may be used for improvement of sleep disturbance caused by atopic dermatitis, wherein the sleep disturbance may be caused by pruritus due to atopic dermatitis. The improvement of sleep disturbance may be characterized by, for example, an increase in the time from falling asleep to awakening, and/or a decrease in sleep onset latency (the time from going to bed to falling asleep).

In a still further embodiment or another embodiment, the pharmaceutical composition of the present disclosure may be used for suppressing at least one symptom caused by atopic dermatitis selected from the group consisting of redness, induration, papules, edema, excoriations, and lichenification.

In one embodiment of the present disclosure, the prevention and/or treatment of atopic dermatitis may refer to, but not limited to, for example, administering a drug or the like to a subject who currently exhibits atopic dermatitis or various symptoms caused by atopic dermatitis (e.g., pruritus, redness, induration, papules, edema, excoriations, lichenification, decrease in QOL, and lack of sleep) to suppress one or more of these symptoms, and/or, for example, administering a drug or the like to a subject who has previously developed atopic dermatitis or various symptoms caused by atopic dermatitis to eliminate the development or reduce the incidence rate of one or more of these symptoms. The prevention and/or treatment of atopic dermatitis may be judged or determined to be useful for the prevention and/or treatment, as long as it improves any one of the various symptoms caused by atopic dermatitis, even though it cannot prevent and/or treat atopic dermatitis per se.

The subject potentially with atopic dermatitis may be a subject who has had atopic dermatitis in the past, and may have a risk of recurrence of the symptoms, or may be a subject with suspected atopic dermatitis before a doctor or the like makes a diagnosis or determination that the subject has atopic dermatitis, but not limited thereto.

In one embodiment, in some cases, the prevention and treatment of atopic dermatitis may be interpreted synonymously.

In a single subcutaneous dose study of the IL-31 antagonist for patients with atopic dermatitis in the Examples, an IL-31 antagonist-treated group demonstrated an improvement in sleep efficiency.

Although atopic dermatitis is not necessarily a life-threatening serious disease, the symptoms associated with the disease significantly affect daily life. In particular, pruritus, which is the most characteristic symptom, is an unpleasant sensation that markedly lowers the patient's quality of life (QOL), and has been reported to hinder the patient's sleep (Zuberbier T, Orlow S J, Paller A S, Taieb A, Allen R, Hemanz-Hermosa J M, Ocampo-Candiani J, Cox M, Langeraar J, Simon J C. Patient perspective on the management of atopic dermatitis. J Allergy Clin Immunol 2006; 118:226-32.). Furthermore, when the patient is a child, there is a significant burden not only on the affected child but also on the parents, and there is a report that the parents of a child with moderate or severe atopic dermatitis spend 3 hours every day in therapeutic treatment, and lose 1 to 2 hours of sleep every day (Su J C, Kemp A S, Varigos G A, Nolan T M. Atopic eczema: its impact on the family and financial cost. Arch Dis Chil 1997; 76:159-62.).

In another embodiment, therefore, the present disclosure relates to a pharmaceutical composition for prevention and/or treatment of atopic dermatitis comprising an IL-31 antagonist as an active ingredient, which is further for improvement of sleep disturbance caused by atopic dermatitis. Alternatively, in a further embodiment or another embodiment, the present disclosure relates to a pharmaceutical composition for improvement of a decrease in QOL caused by atopic dermatitis. The improvement of sleep disturbance may be characterized by, for example, an increase in the time from falling asleep to awakening, and/or a decrease in sleep onset latency (the time from going to bed to falling asleep).

As used herein, the recitation "repeatedly administered in equal amounts at the same dosing interval" in one embodiment may be intended to mean that the dosage (initial dose) at which the IL-31 antagonist of the present disclosure is initially administered to a subject is equal to a continuous dose at which the IL-31 antagonist is subsequently administered (namely, the dose to be continuously administered subsequent to the administration of the initial dose), and the IL-31 antagonist is administered at an equal dosing interval (interval between doses). Specifically, for example, the above-described recitation may mean that the interval between the administration of the initial dose and the administration of the first continuous dose, or every interval between the administration of the n-th (n is an integer of 1 or more) continuous dose and the administration of the (n+1)-th continuous dose is equal, and the doses are equal. Alternatively, in another embodiment, the recitation "repeatedly administered in equal amounts at the same dosing interval" may mean that although the initial dose differs from continuous doses, each continuous dose is equal, and the IL-31 antagonist is administered at an equal dosing interval between continuous doses (interval between doses).

The dose (dosage) expressed in terms of mg/kg or mg/body of the IL-31 antagonist of the present disclosure may be considered to refer to both the initial dose and continuous doses when the initial dose and continuous doses are intended to be the same, and may be considered to refer to continuous doses when the initial dose and continuous doses are intended to be different, unless otherwise indicated, and unless it is contradictory in the context.

A person skilled in the art will naturally understand that, for decided dosing intervals (e.g., every 4 weeks in the case where the dosing interval is decided to be every 4 weeks), each dosing interval has a "tolerable range", and the skilled person can decide the tolerable range, as appropriate.

In one embodiment, in the present disclosure, the repeated administration may mean that, for example, the number of continuous doses subsequent to the initial dose is 1 to 10000 or more, for example, and more specifically, 1, 2, 3, 4, 5, 6, 7, 8, 9, 10, 11, . . . 15, . . . 20, . . . 25, . . . 35, . . . 40, . . . 50, . . . 60, . . . 70, . . . 80, . . . 90, . . . 100, . . . 500, . . . 1000, . . . 10000, . . . , for example, but not limited thereto.

In one embodiment, it is contemplated that the dosing interval of the pharmaceutical composition of the present disclosure or the IL-31 antagonist of the present disclosure is a minimum period of 1 day or longer and a maximum period of 12 weeks or shorter, and may specifically be 1 day, 2 days, 3 days, 4 days, 5 days, 6 days, 1 week, 10 days, 2 weeks, 3 weeks, 4 weeks, 5 weeks, 6 weeks, 7 weeks, 8 weeks, 9 weeks, 10 weeks, 11 weeks, 12 weeks, 1 month, 2 months, or 3 months, for example. The dosing interval may also be expressed differently, and may be specified as once daily or once in 12 weeks, or may be specified as every day or every 12 weeks, for example.

In the present disclosure, the dosage (dose) may be expressed in terms of units other than mg/kg, for example, a fixed dose (mg/body) corresponding to a dose calculated in terms of body weight, or a dose calculated in terms of body surface area (mg/m$^2$).

For example, when it is intended that the IL-31 antagonist of the present disclosure be administered at a fixed dose (mg/body) to a subject with or potentially with atopic dermatitis, dosages in mg/kg of the IL-31 antagonist of the present disclosure may be converted to dosages in mg/body, and an appropriate dosage (mg/body) may be selected and administered to the subject. In this case, although the logic for converting mg/kg to mg/body is not limited, a dosage in mg/body may be determined as appropriate, using a logic known to those skilled in the art. One possible example of such a logic is as follows:

Assuming that there are the minimum effective serum concentration and the maximum tolerable (empirical) serum concentration of the IL-31 antagonist in the present disclosure, changing of a dosage in mg/kg into a dosage in mg/body may be considered such that a serum concentration of the IL-31 antagonist is achieved within this range of concentrations, regardless of body weight. The subject may be a subject having a body weight below 100 kg or below 120 kg, for example. A dosage in mg/body for a subject with a high body weight (e.g., a body weight over 100 kg or over 120 kg) may be increased, as required, but not limited thereto. Moreover, if a dosage in mg/body for a child with a low body weight may markedly increase the exposure, a dosage in mg/kg may be considered.

In a non-limiting embodiment, for a subject with or potentially with atopic dermatitis, for example, a human adult or child, one dosage may be selected from 0.1 to 1000 mg/body, for example, 0.2 mg to 360 mg/body, and preferably, for example, 10 mg to 100 mg/body, 10 mg to 75 mg/body, 10 mg to 50 mg/body, 10 mg to 40 mg/body, 10 mg to 39.5 mg/body, 10 mg to 39 mg/body, 10 mg to 38.5 mg/body, 10 mg to 38 mg/body, 10 mg to 37.5 mg/body, 15 mg to 100 mg/body, 15 mg to 75 mg/body, 15 mg to 50 mg/body, 15 mg to 40 mg/body, 15 mg to 39.5 mg/body, 15 mg to 39 mg/body, 15 mg to 38.5 mg/body, 15 mg to 38 mg/body, 15 mg to 37.5 mg/body, 17.5 mg to 100 mg/body, 17.5 mg to 75 mg/body, 17.5 mg to 50 mg/body, 17.5 mg to 40 mg/body, 17.5 mg to 39.5 mg/body, 17.5 mg to 39 mg/body, 17.5 mg to 38.5 mg/body, 17.5 mg to 38 mg/body, 17.5 mg to 37.5 mg/body, 20 mg to 100 mg/body, 20 mg to 75 mg/body, 20 mg to 50 mg/body, 20 mg to 40 mg/body, 20 mg to 39.5 mg/body, 20 mg to 39 mg/body, 20 mg to 38.5 mg/body, 20 mg to 38 mg/body, 20 mg to 37.5 mg/body, 22.5 mg to 100 mg/body, 22.5 mg to 75 mg/body, 22.5 mg to 50 mg/body, 22.5 mg to 40 mg/body, 22.5 mg to 39.5 mg/body, 22.5 mg to 39 mg/body, 22.5 mg to 38.5 mg/body, 22.5 mg to 38 mg/body, 22.5 mg to 37.5 mg/body, 25 mg to 500 mg/body, 25 mg to 200 mg/body, 25 mg to 120 mg/body, 25 mg to 110 mg/body, 25 mg to 100 mg/body, 25 mg to 90 mg/body, 25 mg to 80 mg/body, 25 mg to 79 mg/body, 25 mg to 78 mg/body, 25 mg to 77 mg/body, 25 mg to 76 mg/body, 25 mg to 75 mg/body, 25 mg to 74 mg/body, 25 mg to 73 mg/body, 25 mg to 72 mg/body, 25 mg to 71 mg/body, 25 mg to 70 mg/body, 25 mg to 50 mg/body, 30 mg to 50 mg/body, 30 mg to 75 mg/body, 30 mg to 100 mg/body, 30 mg to 150 mg/body, 30 mg to 200 mg/body, 30 mg to 250 mg/body, 30 mg to 300 mg/body, 40 mg to 70 mg/body, 40 mg to 71 mg/body, 40 mg to 72 mg/body, 40 mg to 73 mg/body, 40 mg to 74 mg/body, 40 mg to 75 mg/body, 40 mg to 76 mg/body, 40 mg to 77 mg/body, 40 mg to 78 mg/body, 40 mg to 79 mg/body, 40 mg to 80 mg/body, 40 mg to 90 mg/body, 40 mg to 100 mg/body, 40 mg to 110 mg/body, 40 mg to 120 mg/body, 42.5 mg to 70 mg/body, 42.5 mg to 71 mg/body, 42.5 mg to 72 mg/body, 42.5 mg to 73 mg/body, 42.5 mg to 74 mg/body, 42.5 mg to 75 mg/body, 42.5 mg to 76 mg/body, 42.5 mg to 77 mg/body, 42.5 mg to 78 mg/body, 42.5 mg to 79 mg/body, 42.5 mg to 80 mg/body, 42.5 mg to 90 mg/body, 42.5 mg to 100 mg/body, 42.5 mg to 110 mg/body, 42.5 mg to 120 mg/body, 45 mg to 70 mg/body, 45 mg to 71 mg/body, 45 mg to 72 mg/body, 45 mg to 73 mg/body, 45 mg to 74 mg/body, 45 mg to 75 mg/body, 45 mg to 76 mg/body, 45 mg to 77 mg/body, 45 mg to 78 mg/body, 45 mg to 79 mg/body, 45 mg to 80 mg/body, 45 mg to 90 mg/body, 45 mg to 100 mg/body, 45 mg to 110 mg/body, 45 mg to 120 mg/body, 47.5 mg to 70 mg/body, 47.5 mg to 71 mg/body, 47.5 mg to 72 mg/body, 47.5 mg to 73 mg/body, 47.5 mg to 74 mg/body, 47.5 mg to 75 mg/body, 47.5 mg to 76 mg/body, 47.5 mg to 77 mg/body, 47.5 mg to 78 mg/body, 47.5 mg to 79 mg/body, 47.5 mg to 80 mg/body, 47.5 mg to 90 mg/body, 47.5 mg to 100 mg/body, 47.5 mg to 110 mg/body, 47.5 mg to 120 mg/body, 50 mg to 70 mg/body, 50 mg to 71 mg/body, 50 mg to 72 mg/body, 50 mg to 73 mg/body, 50 mg to 74 mg/body, 50 mg to 75 mg/body, 50 mg to 76 mg/body, 50 mg to 77 mg/body, 50 mg to 78 mg/body, 50 mg to 79 mg/body, 50 mg to 80 mg/body, 50 mg to 90 mg/body, 50 mg to 100 mg/body, 50 mg to 110 mg/body, 50 mg to 120 mg/body, 50 mg to 150 mg/body, 50 mg to 200 mg/body, 50 mg to 250 mg/body, 50 mg to 300 mg/body, 52.5 mg to 70 mg/body, 52.5 mg to 71 mg/body, 52.5 mg to 72 mg/body, 52.5 mg to 73 mg/body, 52.5 mg to 74 mg/body, 52.5 mg to 75 mg/body, 52.5 mg to 76 mg/body, 52.5 mg to 77 mg/body, 52.5 mg to 78 mg/body, 52.5 mg to 79 mg/body, 52.5 mg to 80 mg/body, 52.5 mg to 90 mg/body, 52.5 mg to 100 mg/body, 52.5 mg to 110 mg/body, 52.5 mg to 120 mg/body, 75 mg to 100 mg/body, 75 mg to 150 mg/body, 75 mg to 200 mg/body, 75 mg to 250 mg/body, 75 mg to 300 mg/body, 100 mg to 150 mg/body, 100 mg to 200 mg/body, 100 mg to 250 mg/body, 100 mg to 300 mg/body, 150 mg to 200 mg/body, 150 mg to 250 mg/body, 150 mg to 300 mg/body, 200 mg to 250 mg/body, and 200 to 300 mg/body, as the dosage of the IL-31 antagonist of the present disclosure, and may be repeatedly administered using the above-described dosing interval, in equal amounts at the same dosing interval. For the sake of avoiding any doubt, it is expressly stated that, for example, the recitation "0.1 to 1000 mg/body" is intended to mean that all the dosages included between 0.1 and 1000 mg/body are specifically and individually recited herein, with a variation of 0.1 mg/body, for example, 0.1 mg/body, 0.2 mg/body, 0.3 mg/body, 0.4 mg/body, . . . 49.9 mg/body, 50 mg/body, 50.1 mg/body, 50.2 mg/body, . . . 99.8 mg/body, 99.9 mg/body, 100 mg/body, 100.1 mg/body, 100.2 mg/body, . . . 199.9 mg/body, 200 mg/body, 200.1 mg/body, . . . 359.8 mg/body, 359.9 mg/body, 360 mg/body, 360.1 mg/body, . . . 999.8 mg/body, 999.9 mg/body, and 1000 mg/body. Thus, for example, a person skilled in the art who has read the recitation "50 to 200 mg/body", will naturally understand directly and unambiguously that, for example, values such as 50 mg/body, 50.5 mg/body, 51 mg/body, 51.5 mg/body, 52 mg/body, 52.5 mg/body, 53 mg/body, 53.5 mg/body, 54 mg/body, 54.5 mg/body, 55 mg/body, 55.5 mg/body, 56 mg/body, 56.5 mg/body, 57 mg/body, 57.5 mg/body, 58 mg/body, 58.5 mg/body, 59 mg/body, 59.5 mg/body, 60 mg/body, 60.5 mg/body, 61 mg/body, 61.5 mg/body, 62 mg/body, 62.5 mg/body, 63 mg/body, 63.5 mg/body, 64 mg/body, 64.5 mg/body, 65 mg/body, 65.5 mg/body, 66 mg/body, 66.5 mg/body, 67 mg/body, 67.5 mg/body, 68 mg/body, 68.5 mg/body, 69 mg/body, 69.5 mg/body, 70 mg/body, 70.5 mg/body, 71 mg/body, 71.5 mg/body, 72 mg/body, 72.5 mg/body, 73 mg/body, 73.5 mg/body, 74 mg/body, 74.5 mg/body, 75 mg/body, 75.5 mg/body, 76 mg/body, 76.5 mg/body, 77 mg/body, 77.5 mg/body, 78 mg/body, 78.5 mg/body, 79 mg/body, 79.5 mg/body, 80 mg/body, 80.5 mg/body, 81 mg/body, 81.5 mg/body, 82 mg/body, 82.5 mg/body, 83 mg/body, 83.5 mg/body, 84 mg/body, 84.5 mg/body, 85 mg/body, 85.5 mg/body, 86 mg/body, 86.5 mg/body, 87 mg/body, 87.5 mg/body, 88 mg/body, 88.5 mg/body, 89 mg/body, 89.5 mg/body, 90 mg/body, 90.5 mg/body, 91 mg/body, 91.5 mg/body, 92 mg/body, 92.5 mg/body, 93 mg/body, 93.5 mg/body, 94 mg/body, 94.5 mg/body, 95 mg/body, 95.5 mg/body, 96 mg/body, 96.5 mg/body, 97 mg/body, 97.5 mg/body, 98 mg/body, 98.5 mg/body, 99 mg/body, 99.5 mg/body, 100 mg/body, 100.5 mg/body, 101 mg/body, 101.5 mg/body, 102 mg/body, 102.5 mg/body, 103 mg/body, 103.5 mg/body, 104 mg/body, 104.5 mg/body, 105 mg/body, 105.5 mg/body, 106 mg/body, 106.5 mg/body, 107 mg/body, 107.5 mg/body, 108 mg/body, 108.5 mg/body, 109 mg/body, 109.5 mg/body, 110 mg/body, 110.5 mg/body, 111 mg/body, 111.5 mg/body, 112 mg/body, 112.5 mg/body, 113 mg/body, 113.5 mg/body, 114 mg/body, 114.5 mg/body, 115 mg/body, 115.5 mg/body, 116 mg/body, 116.5 mg/body, 117 mg/body, 117.5 mg/body, 118 mg/body, 118.5 mg/body, 119 mg/body, 119.5 mg/body, 120 mg/body, 120.5 mg/body, 121 mg/body, 121.5 mg/body, 122 mg/body, 122.5 mg/body, 123 mg/body, 123.5 mg/body, 124 mg/body, 124.5 mg/body, 125 mg/body, 125.5 mg/body, 126 mg/body, 126.5 mg/body, 127 mg/body, 127.5 mg/body, 128 mg/body, 128.5 mg/body, 129 mg/body, 129.5 mg/body, 130 mg/body, 130.5 mg/body, 131 mg/body, 131.5 mg/body, 132 mg/body, 132.5 mg/body, 133 mg/body, 133.5 mg/body, 134 mg/body, 134.5 mg/body, 135 mg/body, 135.5 mg/body, 136 mg/body, 136.5 mg/body, 137 mg/body, 137.5 mg/body, 138 mg/body, 138.5 mg/body, 139 mg/body, 139.5 mg/body, 140 mg/body, 140.5 mg/body, 141 mg/body, 141.5 mg/body, 142 mg/body, 142.5 mg/body, 143 mg/body, 143.5 mg/body, 144 mg/body, 144.5 mg/body, 145 mg/body, 145.5 mg/body, 146 mg/body, 146.5 mg/body, 147 mg/body, 147.5 mg/body, 148 mg/body, 148.5 mg/body, 149 mg/body, 149.5 mg/body, 150 mg/body, 150.5 mg/body, 151 mg/body, 151.5 mg/body, 152 mg/body, 152.5 mg/body, 153 mg/body, 153.5 mg/body, 154 mg/body, 154.5 mg/body, 155 mg/body, 155.5 mg/body, 156 mg/body, 156.5 mg/body, 157 mg/body, 157.5 mg/body, 158 mg/body, 158.5 mg/body, 159 mg/body, 159.5 mg/body, 160 mg/body, 160.5 mg/body, 161 mg/body, 161.5 mg/body, 162 mg/body, 162.5 mg/body, 163 mg/body, 163.5 mg/body, 164 mg/body, 164.5 mg/body, 165 mg/body, 165.5 mg/body, 166 mg/body, 166.5 mg/body, 167 mg/body, 167.5 mg/body, 168 mg/body, 168.5 mg/body, 169 mg/body, 169.5 mg/body, 170 mg/body, 170.5 mg/body, 171 mg/body, 171.5 mg/body, 172 mg/body, 172.5 mg/body, 173 mg/body, 173.5 mg/body, 174 mg/body, 174.5 mg/body, 175 mg/body, 175.5 mg/body, 176 mg/body, 176.5 mg/body, 177 mg/body, 177.5 mg/body, 178 mg/body, 178.5 mg/body, 179 mg/body, 179.5 mg/body, 180 mg/body, 180.5 mg/body, 181 mg/body, 181.5 mg/body, 182 mg/body, 182.5 mg/body, 183 mg/body, 183.5 mg/body, 184 mg/body, 184.5 mg/body, 185 mg/body, 185.5 mg/body, 186 mg/body, 186.5 mg/body, 187 mg/body, 187.5 mg/body, 188 mg/body, 188.5 mg/body, 189 mg/body, 189.5 mg/body, 190 mg/body, 190.5 mg/body, 191 mg/body, 191.5 mg/body, 192 mg/body, 192.5 mg/body, 193 mg/body, 193.5 mg/body, 194 mg/body, 194.5 mg/body, 195 mg/body, 195.5 mg/body, 196 mg/body, 196.5 mg/body, 197 mg/body, 197.5 mg/body, 198 mg/body, 198.5 mg/body, 199 mg/body, 199.5 mg/body, and 200 mg/body are specifically and individually recited.

Alternatively, in another non-limiting embodiment, for a subject with or potentially with atopic dermatitis, for example, a human child, one dosage may be selected from 0.01 to 10 mg/kg, for example, 0.05 to 7.5 mg/kg, 0.075 to 5 mg/kg, or 0.1 to 3 mg/kg, and preferably, for example, 0.1 mg to 0.25 mg/kg, 0.1 mg to 0.3 mg/kg, 0.1 mg to 0.5 mg/kg, 0.1 mg to 0.75 mg/kg, 0.1 mg to 1 mg/kg, 0.1 mg to 1.5 mg/kg, 0.1 mg to 2 mg/kg, 0.1 mg to 3 mg/kg, 0.125 mg to 0.25 mg/kg, 0.125 mg to 0.3 mg/kg, 0.125 mg to 0.5 mg/kg, 0.125 mg to 0.75 mg/kg, 0.125 mg to 1 mg/kg, 0.125 mg to 1.5 mg/kg, 0.125 mg to 2 mg/kg, 0.125 mg to 3 mg/kg, 0.2 mg to 0.3 mg/kg, 0.2 mg to 0.5 mg/kg, 0.2 mg to 0.75 mg/kg, 0.2 mg to 1 mg/kg, 0.2 mg to 1.5 mg/kg, 0.2 mg to 2 mg/kg, 0.2 mg to 3 mg/kg, 0.25 mg to 0.3 mg/kg, 0.25 mg to 0.5 mg/kg, 0.25 mg to 0.75 mg/kg, 0.25 mg to 1 mg/kg, 0.25 mg to 1.5 mg/kg, 0.25 mg to 2 mg/kg, 0.25 mg to 3 mg/kg, 0.3 mg to 0.5 mg/kg, 0.3 mg to 0.75 mg/kg, 0.3 mg to 1 mg/kg, 0.3 mg to 1.5 mg/kg, 0.3 mg to 2 mg/kg, 0.3 mg to 3 mg/kg, 0.5 mg to 0.75 mg/kg, 0.5 mg to 1 mg/kg, 0.5 mg to 1.5 mg/kg, 0.5 mg to 2 mg/kg, 0.5 mg to 3 mg/kg, 0.75 mg to 1 mg/kg, 0.75 mg to 1.5 mg/kg, 0.75 mg to 2 mg/kg, 0.75 mg to 3 mg/kg, 1 mg to 1.5 mg/kg, 1 mg to 2 mg/kg, 1 mg to 3 mg/kg, 1.5 mg to 2 mg/kg, 1.5 mg to 3 mg/kg, 2 mg to 3 mg/kg, 0.15 mg to 2.9 mg/kg, 0.2 mg to 2.8 mg/kg, 0.25 mg to 2.7 mg/kg, 0.3 mg to 2.6 mg/kg, 0.35 mg to 2.5 mg/kg, 0.4 mg to 2.4 mg/kg, 0.425 mg to 2.3 mg/kg, 0.45 mg to 2.2 mg/kg, 0.475 to 2.1 mg/kg, or 0.5 to 2 mg/kg, or more preferably from 0.5 to 1.5 mg/kg, for example, as the dosage of the IL-31 antagonist of the present disclosure, and may be repeatedly administered using the above-described dosing interval, in equal amounts at the same dosing interval. For the sake of avoiding any doubt, it is expressly stated that, for example, the recitation "0.01 to 10 mg/kg" is intended to mean that all the dosages included between 0.01 and 10 mg/kg are specifically and individually recited herein, with a variation of 0.005 mg/body, for example, 0.01 mg/kg, 0.015 mg/kg, 0.02 mg/kg, 0.025 mg/kg, 0.03 mg/kg, 0.035 mg/kg, 0.04 mg/kg, . . . 0.125 mg/kg, . . . 0.49 mg/kg, 0.495 mg/kg, 0.5 mg/kg, 0.505 mg/kg, 0.51 mg/kg, . . . 0.98 mg/kg, 0.985 mg/kg, 0.99 mg/kg, 0.995 mg/kg, 1 mg/kg, 1.005 mg/kg, 1.01 mg/kg, . . . , 1.49 mg/kg, 1.495 mg/kg, 1.5 mg/kg, 1.505 mg/kg, 1.51 mg/kg, . . . 1.98 mg/kg, 1.985 mg/kg, 1.99 mg/kg, 1.995 mg/kg, 2 mg/kg, 2.005 mg/kg, 2.01 mg/kg, . . . 2.99 mg/kg, 2.995 mg/kg, 3 mg/kg, 3.005 mg/kg, 3.01 mg/kg, . . . 9.98 mg/kg, 9.985 mg/kg, 9.99 mg/kg, 9.995 mg/kg, and 10 mg/kg. Thus, for example, a person skilled in the art who has read the recitation "0.1 to 3 mg/kg", will naturally understand directly and unambiguously that, for example, values such as 0.1 mg/kg, 0.11 mg/kg, 0.12 mg/kg, 0.125 mg/kg, 0.13 mg/kg, 0.14 mg/kg, 0.15 mg/kg, 0.16 mg/kg, 0.17 mg/kg, 0.18 mg/kg, 0.19 mg/kg, 0.2 mg/kg, 0.21 mg/kg, 0.22 mg/kg, 0.23 mg/kg, 0.24 mg/kg, 0.25 mg/kg, 0.26 mg/kg, 0.27 mg/kg, 0.28 mg/kg, 0.29 mg/kg, 0.3 mg/kg, 0.31 mg/kg, 0.32 mg/kg, 0.33 mg/kg, 0.34 mg/kg, 0.35 mg/kg, 0.36 mg/kg, 0.37 mg/kg, 0.38 mg/kg, 0.39 mg/kg, 0.4 mg/kg, 0.41 mg/kg, 0.42 mg/kg, 0.43 mg/kg, 0.44 mg/kg, 0.45 mg/kg, 0.46 mg/kg, 0.47 mg/kg, 0.48 mg/kg, 0.49 mg/kg, 0.5 mg/kg, 0.51 mg/kg, 0.52 mg/kg, 0.53 mg/kg, 0.54 mg/kg, 0.55 mg/kg, 0.56 mg/kg, 0.57 mg/kg, 0.58 mg/kg, 0.59 mg/kg, 0.6 mg/kg, 0.61 mg/kg, 0.62 mg/kg, 0.63 mg/kg, 0.64 mg/kg, 0.65 mg/kg, 0.66 mg/kg, 0.67 mg/kg, 0.68 mg/kg, 0.69 mg/kg, 0.7 mg/kg, 0.71 mg/kg, 0.72 mg/kg, 0.73 mg/kg, 0.74 mg/kg, 0.75 mg/kg, 0.76 mg/kg, 0.77 mg/kg, 0.78 mg/kg, 0.79 mg/kg, 0.8 mg/kg, 0.81 mg/kg, 0.82 mg/kg, 0.83 mg/kg, 0.84 mg/kg, 0.85 mg/kg, 0.86 mg/kg, 0.87 mg/kg, 0.88 mg/kg, 0.89 mg/kg, 0.9 mg/kg, 0.91 mg/kg, 0.92 mg/kg, 0.93 mg/kg, 0.94 mg/kg, 0.95 mg/kg, 0.96 mg/kg, 0.97 mg/kg, 0.98 mg/kg, 0.99 mg/kg, 1 mg/kg, 1.01 mg/kg, 1.02 mg/kg, 1.03 mg/kg, 1.04 mg/kg, 1.05 mg/kg, 1.06 mg/kg, 1.07 mg/kg, 1.08 mg/kg, 1.09 mg/kg, 1.1 mg/kg, 1.11 mg/kg, 1.12 mg/kg, 1.13 mg/kg, 1.14 mg/kg, 1.15 mg/kg, 1.16 mg/kg, 1.17 mg/kg, 1.18 mg/kg, 1.19 mg/kg, 1.2 mg/kg, 1.21 mg/kg, 1.22 mg/kg, 1.23 mg/kg, 1.24 mg/kg, 1.25 mg/kg, 1.26 mg/kg, 1.27 mg/kg, 1.28 mg/kg, 1.29 mg/kg, 1.3 mg/kg, 1.31 mg/kg, 1.32 mg/kg, 1.33 mg/kg, 1.34 mg/kg, 1.35 mg/kg, 1.36 mg/kg, 1.37 mg/kg, 1.38 mg/kg, 1.39 mg/kg, 1.4 mg/kg, 1.41 mg/kg, 1.42 mg/kg, 1.43 mg/kg, 1.44 mg/kg, 1.45 mg/kg, 1.46 mg/kg, 1.47 mg/kg, 1.48 mg/kg, 1.49 mg/kg, 1.5 mg/kg, 1.51 mg/kg, 1.52 mg/kg, 1.53 mg/kg, 1.54 mg/kg, 1.55 mg/kg, 1.56 mg/kg, 1.57 mg/kg, 1.58 mg/kg, 1.59 mg/kg, 1.6 mg/kg, 1.61 mg/kg, 1.62 mg/kg, 1.63 mg/kg, 1.64 mg/kg, 1.65 mg/kg, 1.66 mg/kg, 1.67 mg/kg, 1.68 mg/kg, 1.69 mg/kg, 1.7 mg/kg, 1.71 mg/kg, 1.72 mg/kg, 1.73 mg/kg, 1.74 mg/kg, 1.75 mg/kg, 1.76 mg/kg, 1.77 mg/kg, 1.78 mg/kg, 1.79 mg/kg, 1.8 mg/kg, 1.81 mg/kg, 1.82 mg/kg, 1.83 mg/kg, 1.84 mg/kg, 1.85 mg/kg, 1.86 mg/kg, 1.87 mg/kg, 1.88 mg/kg, 1.89 mg/kg, 1.9 mg/kg, 1.91 mg/kg, 1.92 mg/kg, 1.93 mg/kg, 1.94 mg/kg, 1.95 mg/kg, 1.96 mg/kg, 1.97 mg/kg, 1.98 mg/kg, 1.99 mg/kg, 2 mg/kg, 2.01 mg/kg, 2.02 mg/kg, 2.03 mg/kg, 2.04 mg/kg, 2.05 mg/kg, 2.06 mg/kg, 2.07 mg/kg, 2.08 mg/kg, 2.09 mg/kg, 2.1 mg/kg, 2.11 mg/kg, 2.12 mg/kg, 2.13 mg/kg, 2.14 mg/kg, 2.15 mg/kg, 2.16 mg/kg, 2.17 mg/kg, 2.18 mg/kg, 2.19 mg/kg, 2.2 mg/kg, 2.21 mg/kg, 2.22 mg/kg, 2.23 mg/kg, 2.24 mg/kg, 2.25 mg/kg, 2.26 mg/kg, 2.27 mg/kg, 2.28 mg/kg, 2.29 mg/kg, 2.3 mg/kg, 2.31 mg/kg, 2.32 mg/kg, 2.33 mg/kg, 2.34 mg/kg, 2.35 mg/kg, 2.36 mg/kg, 2.37 mg/kg, 2.38 mg/kg, 2.39 mg/kg, 2.4 mg/kg, 2.41 mg/kg, 2.42 mg/kg, 2.43 mg/kg, 2.44 mg/kg, 2.45 mg/kg, 2.46 mg/kg, 2.47 mg/kg, 2.48 mg/kg, 2.49 mg/kg, 2.5 mg/kg, 2.51 mg/kg, 2.52 mg/kg, 2.53 mg/kg, 2.54 mg/kg, 2.55 mg/kg, 2.56 mg/kg, 2.57 mg/kg, 2.58 mg/kg, 2.59 mg/kg, 2.6 mg/kg, 2.61 mg/kg, 2.62 mg/kg, 2.63 mg/kg, 2.64 mg/kg, 2.65 mg/kg, 2.66 mg/kg, 2.67 mg/kg, 2.68 mg/kg, 2.69 mg/kg, 2.7 mg/kg, 2.71 mg/kg, 2.72 mg/kg, 2.73 mg/kg, 2.74 mg/kg, 2.75 mg/kg, 2.76 mg/kg, 2.77 mg/kg, 2.78 mg/kg, 2.79 mg/kg, 2.8 mg/kg, 2.81 mg/kg, 2.82 mg/kg, 2.83 mg/kg, 2.84 mg/kg, 2.85 mg/kg, 2.86 mg/kg, 2.87 mg/kg, 2.88 mg/kg, 2.89 mg/kg, 2.9 mg/kg, 2.91 mg/kg, 2.92 mg/kg, 2.93 mg/kg, 2.94 mg/kg, 2.95 mg/kg, 2.96 mg/kg, 2.97 mg/kg, 2.98 mg/kg, 2.99 mg/kg, and 3 mg/kg are specifically and individually recited.

As described above, in an embodiment where the IL-31 antagonist of the present disclosure is repeatedly administered in equal amounts at the same dosing interval, using a predetermined dosing interval and a predetermined dose (dosage), the IL-31 antagonist of the present disclosure may be administered at "0.1 to 1000 mg/body/1 day to 12 weeks". As used herein, the recitation "0.1 to 1000 mg/body/1 day to 12 weeks", for example, is contemplated to mean that one dosage is selected from 0.1 to 1000 mg as the dosage (e.g., 100 mg/body) of the IL-31 antagonist of the present disclosure, and any one dosing interval is selected from 1 day to 12 weeks as the dosing interval (e.g., 4 weeks) of the IL-31 antagonist of the present disclosure, and the IL-31 antagonist is repeatedly administered to a subject in equal amounts at the same dosing interval. As an example, the recitation "100 mg/body/4 weeks" is contemplated to mean that 100 mg/body of the IL-31 antagonist of the present disclosure is repeatedly administered to a subject every 4 weeks in equal amounts at the same dosing interval. In an embodiment where the IL-31 antagonist of the present disclosure is repeatedly administered in equal amounts at the same dosing interval, using a predetermined dosing interval and a predetermined dose (dosage), the IL-31 antagonist of the present disclosure is preferably administered at 0.1 to 1000 mg/body/2 to 8 weeks, and may be administered at, for example, 0.1 to 1000 mg/body/2 weeks, 0.1 to 1000 mg/body/4 weeks, 0.1 to 1000 mg/body/6 weeks, or 0.1 to 1000 mg/body/8 weeks, but not limited thereto. Alternatively, the IL-31 antagonist of the present disclosure is more preferably administered at 0.2 to 360 mg/body/2 to 8 weeks, and may be administered at, for example, 0.2 to 360 mg/body/2 weeks, 0.2 to 360 mg/body/4 weeks, 0.2 to 360 mg/body/6 weeks, or 0.2 to 360 mg/body/8 weeks. Alternatively, as an example, the IL-31 antagonist of the present disclosure is still more preferably administered at 10 to 200 mg/body/2 to 8 weeks, and may be administered at, for example, 10 to 200 mg/body/2 weeks, 10 to 200 mg/body/4 weeks, 10 to 200 mg/body/6 weeks, or 10 to 200 mg/body/8 weeks. Alternatively, as an example, the IL-31 antagonist of the present disclosure is even more preferably administered at 10 to 100 mg/body/2 to 8 weeks, and may be administered at, for example, 10 to 100 mg/body/2 weeks, 10 to 100 mg/body/4 weeks, 10 to 100 mg/body/6 weeks, or 10 to 100 mg/body/8 weeks. Alternatively, as an example, the IL-31 antagonist of the present disclosure may be administered at 25 to 100 mg/body/4 weeks, 25 to 80 mg/body/4 weeks, 25 to 75 mg/body/4 weeks, 50 to 100 mg/body/4 weeks, 50 to 80 mg/body/4 weeks, or 50 to 75 mg/body/4 weeks, or at 10 to 50 mg/body/2 weeks or 20 to 40 mg/body/2 weeks. In a non-limiting embodiment, the IL-31 antagonist of the present disclosure may be administered at, for example, 50 mg/body/4 weeks, 50.5 mg/body/4 weeks, 51 mg/body/4 weeks, 51.5 mg/body/4 weeks, 52 mg/body/4 weeks, 52.5 mg/body/4 weeks, 53 mg/body/4 weeks, 53.5 mg/body/4 weeks, 54 mg/body/4 weeks, 54.5 mg/body/4 weeks, 55 mg/body/4 weeks, 55.5 mg/body/4 weeks, 56 mg/body/4 weeks, 56.5 mg/body/4 weeks, 57 mg/body/4 weeks, 57.5 mg/body/4 weeks, 58 mg/body/4 weeks, 58.5 mg/body/4 weeks, 59 mg/body/4 weeks, 59.5 mg/body/4 weeks, 60 mg/body/4 weeks, 60.5 mg/body/4 weeks, 61 mg/body/4 weeks, 61.5 mg/body/4 weeks, 62 mg/body/4 weeks, 62.5 mg/body/4 weeks, 63 mg/body/4 weeks, 63.5 mg/body/4 weeks, 64 mg/body/4 weeks, 64.5 mg/body/4 weeks, 65 mg/body/4 weeks, 65.5 mg/body/4 weeks, 66 mg/body/4 weeks, 66.5 mg/body/4 weeks, 67 mg/body/4 weeks, 67.5 mg/body/4 weeks, 68 mg/body/4 weeks, 68.5 mg/body/4 weeks, 69 mg/body/4 weeks, 69.5 mg/body/4 weeks, 70 mg/body/4 weeks, 70.5 mg/body/4 weeks, 71 mg/body/4 weeks, 71.5 mg/body/4 weeks, 72 mg/body/4 weeks, 72.5 mg/body/4 weeks, 73 mg/body/4 weeks, 73.5 mg/body/4 weeks, 74 mg/body/4 weeks, 74.5 mg/body/4 weeks, 75 mg/body/4 weeks, 75.5 mg/body/4 weeks, 76 mg/body/4 weeks, 76.5 mg/body/4 weeks, 77 mg/body/4 weeks, 77.5 mg/body/4 weeks, 78 mg/body/4 weeks, 78.5 mg/body/4 weeks, 79 mg/body/4 weeks, 79.5 mg/body/4 weeks, 80 mg/body/4 weeks, 80.5 mg/body/4 weeks, 81 mg/body/4 weeks, 81.5 mg/body/4 weeks, 82 mg/body/4 weeks, 82.5 mg/body/4 weeks, 83 mg/body/4 weeks, 83.5 mg/body/4 weeks, 84 mg/body/4 weeks, 84.5 mg/body/4 weeks, 85 mg/body/4 weeks, 85.5 mg/body/4 weeks, 86 mg/body/4 weeks, 86.5 mg/body/4 weeks, 87 mg/body/4 weeks, 87.5 mg/body/4 weeks, 88 mg/body/4 weeks, 88.5 mg/body/4 weeks, 89 mg/body/4 weeks, 89.5 mg/body/4 weeks, 90 mg/body/4 weeks, 90.5 mg/body/4 weeks, 91 mg/body/4 weeks, 91.5 mg/body/4 weeks, 92 mg/body/4 weeks, 92.5 mg/body/4 weeks, 93 mg/body/4 weeks, 93.5 mg/body/4 weeks, 94 mg/body/4 weeks, 94.5 mg/body/4 weeks, 95 mg/body/4 weeks, 95.5 mg/body/4 weeks, 96 mg/body/4 weeks, 96.5 mg/body/4 weeks, 97 mg/body/4 weeks, 97.5 mg/body/4 weeks, 98 mg/body/4 weeks, 98.5 mg/body/4 weeks, 99 mg/body/4 weeks, 99.5 mg/body/4 weeks, 100 mg/body/4 weeks, 100.5 mg/body/4 weeks, 101 mg/body/4 weeks, 101.5 mg/body/4 weeks, 102 mg/body/4 weeks, 102.5 mg/body/4 weeks, 103 mg/body/4 weeks, 103.5 mg/body/4 weeks, 104 mg/body/4 weeks, 104.5 mg/body/4 weeks, 105 mg/body/4 weeks, 105.5 mg/body/4 weeks, 106 mg/body/4 weeks, 106.5 mg/body/4 weeks, 107 mg/body/4 weeks, 107.5 mg/body/4 weeks, 108 mg/body/4 weeks, 108.5 mg/body/4 weeks, 109 mg/body/4 weeks, 109.5 mg/body/4 weeks, 110 mg/body/4 weeks, 110.5 mg/body/4 weeks, 111 mg/body/4 weeks, 111.5 mg/body/4 weeks, 112 mg/body/4 weeks, 112.5 mg/body/4 weeks, 113 mg/body/4 weeks, 113.5 mg/body/4 weeks, 114 mg/body/4 weeks, 114.5 mg/body/4 weeks, 115 mg/body/4 weeks, 115.5 mg/body/4 weeks, 116 mg/body/4 weeks, 116.5 mg/body/4 weeks, 117 mg/body/4 weeks, 117.5 mg/body/4 weeks, 118 mg/body/4 weeks, 118.5 mg/body/4 weeks, 119 mg/body/4 weeks, 119.5 mg/body/4 weeks, 120 mg/body/4 weeks, 120.5 mg/body/4 weeks, 121 mg/body/4 weeks, 121.5 mg/body/4 weeks, 122 mg/body/4 weeks, 122.5 mg/body/4 weeks, 123 mg/body/4 weeks, 123.5 mg/body/4 weeks, 124 mg/body/4 weeks, 124.5 mg/body/4 weeks, 125 mg/body/4 weeks, 125.5 mg/body/4 weeks, 126 mg/body/4 weeks, 126.5 mg/body/4 weeks, 127 mg/body/4 weeks, 127.5 mg/body/4 weeks, 128 mg/body/4 weeks, 128.5 mg/body/4 weeks, 129 mg/body/4 weeks, 129.5 mg/body/4 weeks, 130 mg/body/4 weeks, 130.5 mg/body/4 weeks, 131 mg/body/4 weeks, 131.5 mg/body/4 weeks, 132 mg/body/4 weeks, 132.5 mg/body/4 weeks, 133 mg/body/4 weeks, 133.5 mg/body/4 weeks, 134 mg/body/4 weeks, 134.5 mg/body/4 weeks, 135 mg/body/4 weeks, 135.5 mg/body/4 weeks, 136 mg/body/4 weeks, 136.5 mg/body/4 weeks, 137 mg/body/4 weeks, 137.5 mg/body/4 weeks, 138 mg/body/4 weeks, 138.5 mg/body/4 weeks, 139 mg/body/4 weeks, 139.5 mg/body/4 weeks, 140 mg/body/4 weeks, 140.5 mg/body/4 weeks, 141 mg/body/4 weeks, 141.5 mg/body/4 weeks, 142 mg/body/4 weeks, 142.5 mg/body/4 weeks, 143 mg/body/4 weeks, 143.5 mg/body/4 weeks, 144 mg/body/4 weeks, 144.5 mg/body/4 weeks, 145 mg/body/4 weeks, 145.5 mg/body/4 weeks, 146 mg/body/4 weeks, 146.5 mg/body/4 weeks, 147 mg/body/4 weeks, 147.5 mg/body/4 weeks, 148 mg/body/4 weeks, 148.5 mg/body/4 weeks, 149 mg/body/4 weeks, 149.5 mg/body/4 weeks, 150 mg/body/4 weeks, 150.5 mg/body/4 weeks, 151 mg/body/4 weeks, 151.5 mg/body/4 weeks, 152 mg/body/4 weeks, 152.5 mg/body/4 weeks, 153 mg/body/4 weeks, 153.5 mg/body/4 weeks, 154 mg/body/4 weeks, 154.5 mg/body/4 weeks, 155 mg/body/4 weeks, 155.5 mg/body/4 weeks, 156 mg/body/4 weeks, 156.5 mg/body/4 weeks, 157 mg/body/4 weeks, 157.5 mg/body/4 weeks, 158 mg/body/4 weeks, 158.5 mg/body/4 weeks, 159 mg/body/4 weeks, 159.5 mg/body/4 weeks, 160 mg/body/4 weeks, 160.5 mg/body/4 weeks, 161 mg/body/4 weeks, 161.5 mg/body/4 weeks, 162 mg/body/4 weeks, 162.5 mg/body/4 weeks, 163 mg/body/4 weeks, 163.5 mg/body/4 weeks, 164 mg/body/4 weeks, 164.5 mg/body/4 weeks, 165 mg/body/4 weeks, 165.5 mg/body/4 weeks, 166 mg/body/4 weeks, 166.5 mg/body/4 weeks, 167 mg/body/4 weeks, 167.5 mg/body/4 weeks, 168 mg/body/4 weeks, 168.5 mg/body/4 weeks, 169 mg/body/4 weeks, 169.5 mg/body/4 weeks, 170 mg/body/4 weeks, 170.5 mg/body/4 weeks, 171 mg/body/4 weeks, 171.5 mg/body/4 weeks, 172 mg/body/4 weeks, 172.5 mg/body/4 weeks, 173 mg/body/4 weeks, 173.5 mg/body/4 weeks, 174 mg/body/4 weeks, 174.5 mg/body/4 weeks, 175 mg/body/4 weeks, 175.5 mg/body/4 weeks, 176 mg/body/4 weeks, 176.5 mg/body/4 weeks, 177 mg/body/4 weeks, 177.5 mg/body/4 weeks, 178 mg/body/4 weeks, 178.5 mg/body/4 weeks, 179 mg/body/4 weeks, 179.5 mg/body/4 weeks, 180 mg/body/4 weeks, 180.5 mg/body/4 weeks, 181 mg/body/4 weeks, 181.5 mg/body/4 weeks, 182 mg/body/4 weeks, 182.5 mg/body/4 weeks, 183 mg/body/4 weeks, 183.5 mg/body/4 weeks, 184 mg/body/4 weeks, 184.5 mg/body/4 weeks, 185 mg/body/4 weeks, 185.5 mg/body/4 weeks, 186 mg/body/4 weeks, 186.5 mg/body/4 weeks, 187 mg/body/4 weeks, 187.5 mg/body/4 weeks, 188 mg/body/4 weeks, 188.5 mg/body/4 weeks, 189 mg/body/4 weeks, 189.5 mg/body/4 weeks, 190 mg/body/4 weeks, 190.5 mg/body/4 weeks, 191 mg/body/4 weeks, 191.5 mg/body/4 weeks, 192 mg/body/4 weeks, 192.5 mg/body/4 weeks, 193 mg/body/4 weeks, 193.5 mg/body/4 weeks, 194 mg/body/4 weeks, 194.5 mg/body/4 weeks, 195 mg/body/4 weeks, 195.5 mg/body/4 weeks, 196 mg/body/4 weeks, 196.5 mg/body/4 weeks, 197 mg/body/4 weeks, 197.5 mg/body/4 weeks, 198 mg/body/4 weeks, 198.5 mg/body/4 weeks, 199 mg/body/4 weeks, 199.5 mg/body/4 weeks, or 200 mg/body/4 weeks. Alternatively, in a non-limiting embodiment, the IL-31 antagonist of the present disclosure may be administered at, for example, 50 mg/body/6 weeks, 50.5 mg/body/6 weeks, 51 mg/body/6 weeks, 51.5 mg/body/6 weeks, 52 mg/body/6 weeks, 52.5 mg/body/6 weeks, 53 mg/body/6 weeks, 53.5 mg/body/6 weeks, 54 mg/body/6 weeks, 54.5 mg/body/6 weeks, 55 mg/body/6 weeks, 55.5 mg/body/6 weeks, 56 mg/body/6 weeks, 56.5 mg/body/6 weeks, 57 mg/body/6 weeks, 57.5 mg/body/6 weeks, 58 mg/body/6 weeks, 58.5 mg/body/6 weeks, 59 mg/body/6 weeks, 59.5 mg/body/6 weeks, 60 mg/body/6 weeks, 60.5 mg/body/6 weeks, 61 mg/body/6 weeks, 61.5 mg/body/6 weeks, 62 mg/body/6 weeks, 62.5 mg/body/6 weeks, 63 mg/body/6 weeks, 63.5 mg/body/6 weeks, 64 mg/body/6 weeks, 64.5 mg/body/6 weeks, 65 mg/body/6 weeks, 65.5 mg/body/6 weeks, 66 mg/body/6 weeks, 66.5 mg/body/6 weeks, 67 mg/body/6 weeks, 67.5 mg/body/6 weeks, 68 mg/body/6 weeks, 68.5 mg/body/6 weeks, 69 mg/body/6 weeks, 69.5 mg/body/6 weeks, 70 mg/body/6 weeks, 70.5 mg/body/6 weeks, 71 mg/body/6 weeks, 71.5 mg/body/6 weeks, 72 mg/body/6 weeks, 72.5 mg/body/6 weeks, 73 mg/body/6 weeks, 73.5 mg/body/6 weeks, 74 mg/body/6 weeks, 74.5 mg/body/6 weeks, 75 mg/body/6 weeks, 75.5 mg/body/6 weeks, 76 mg/body/6 weeks, 76.5 mg/body/6 weeks, 77 mg/body/6 weeks, 77.5 mg/body/6 weeks, 78 mg/body/6 weeks, 78.5 mg/body/6 weeks, 79 mg/body/6 weeks, 79.5 mg/body/6 weeks, 80 mg/body/6 weeks, 80.5 mg/body/6 weeks, 81 mg/body/6 weeks, 81.5 mg/body/6 weeks, 82 mg/body/6 weeks, 82.5 mg/body/6 weeks, 83 mg/body/6 weeks, 83.5 mg/body/6 weeks, 84 mg/body/6 weeks, 84.5 mg/body/6 weeks, 85 mg/body/6 weeks, 85.5 mg/body/6 weeks, 86 mg/body/6 weeks, 86.5 mg/body/6 weeks, 87 mg/body/6 weeks, 87.5 mg/body/6 weeks, 88 mg/body/6 weeks, 88.5 mg/body/6 weeks, 89 mg/body/6 weeks, 89.5 mg/body/6 weeks, 90 mg/body/6 weeks, 90.5 mg/body/6 weeks, 91 mg/body/6 weeks, 91.5 mg/body/6 weeks, 92 mg/body/6 weeks, 92.5 mg/body/6 weeks, 93 mg/body/6 weeks, 93.5 mg/body/6 weeks, 94 mg/body/6 weeks, 94.5 mg/body/6 weeks, 95 mg/body/6 weeks, 95.5 mg/body/6 weeks, 96 mg/body/6 weeks, 96.5 mg/body/6 weeks, 97 mg/body/6 weeks, 97.5 mg/body/6 weeks, 98 mg/body/6 weeks, 98.5 mg/body/6 weeks, 99 mg/body/6 weeks, 99.5 mg/body/6 weeks, 100 mg/body/6 weeks, 100.5 mg/body/6 weeks, 101 mg/body/6 weeks, 101.5 mg/body/6 weeks, 102 mg/body/6 weeks, 102.5 mg/body/6 weeks, 103 mg/body/6 weeks, 103.5 mg/body/6 weeks, 104 mg/body/6 weeks, 104.5 mg/body/6 weeks, 105 mg/body/6 weeks, 105.5 mg/body/6 weeks, 106 mg/body/6 weeks, 106.5 mg/body/6 weeks, 107 mg/body/6 weeks, 107.5 mg/body/6 weeks, 108 mg/body/6 weeks, 108.5 mg/body/6 weeks, 109 mg/body/6 weeks, 109.5 mg/body/6 weeks, 110 mg/body/6 weeks, 110.5 mg/body/6 weeks, 111 mg/body/6 weeks, 111.5 mg/body/6 weeks, 112 mg/body/6 weeks, 112.5 mg/body/6 weeks, 113 mg/body/6 weeks, 113.5 mg/body/6 weeks, 114 mg/body/6 weeks, 114.5 mg/body/6 weeks, 115 mg/body/6 weeks, 115.5 mg/body/6 weeks, 116 mg/body/6 weeks, 116.5 mg/body/6 weeks, 117 mg/body/6 weeks, 117.5 mg/body/6 weeks, 118 mg/body/6 weeks, 118.5 mg/body/6 weeks, 119 mg/body/6 weeks, 119.5 mg/body/6 weeks, 120 mg/body/6 weeks, 120.5 mg/body/6 weeks, 121 mg/body/6 weeks, 121.5 mg/body/6 weeks, 122 mg/body/6 weeks, 122.5 mg/body/6 weeks, 123 mg/body/6 weeks, 123.5 mg/body/6 weeks, 124 mg/body/6 weeks, 124.5 mg/body/6 weeks, 125 mg/body/6 weeks, 125.5 mg/body/6 weeks, 126 mg/body/6 weeks, 126.5 mg/body/6 weeks, 127 mg/body/6 weeks, 127.5 mg/body/6 weeks, 128 mg/body/6 weeks, 128.5 mg/body/6 weeks, 129 mg/body/6 weeks, 129.5 mg/body/6 weeks, 130 mg/body/6 weeks, 130.5 mg/body/6 weeks, 131 mg/body/6 weeks, 131.5 mg/body/6 weeks, 132 mg/body/6 weeks, 132.5 mg/body/6 weeks, 133 mg/body/6 weeks, 133.5 mg/body/6 weeks, 134 mg/body/6 weeks, 134.5 mg/body/6 weeks, 135 mg/body/6 weeks, 135.5 mg/body/6 weeks, 136 mg/body/6 weeks, 136.5 mg/body/6 weeks, 137 mg/body/6 weeks, 137.5 mg/body/6 weeks, 138 mg/body/6 weeks, 138.5 mg/body/6 weeks, 139 mg/body/6 weeks, 139.5 mg/body/6 weeks, 140 mg/body/6 weeks, 140.5 mg/body/6 weeks, 141 mg/body/6 weeks, 141.5 mg/body/6 weeks, 142 mg/body/6 weeks, 142.5 mg/body/6 weeks, 143 mg/body/6 weeks, 143.5 mg/body/6 weeks, 144 mg/body/6 weeks, 144.5 mg/body/6 weeks, 145 mg/body/6 weeks, 145.5 mg/body/6 weeks, 146 mg/body/6 weeks, 146.5 mg/body/6 weeks, 147 mg/body/6 weeks, 147.5 mg/body/6 weeks, 148 mg/body/6 weeks, 148.5 mg/body/6 weeks, 149 mg/body/6 weeks, 149.5 mg/body/6 weeks, 150 mg/body/6 weeks, 150.5 mg/body/6 weeks, 151 mg/body/6 weeks, 151.5 mg/body/6 weeks, 152 mg/body/6 weeks, 152.5 mg/body/6 weeks, 153 mg/body/6 weeks, 153.5 mg/body/6 weeks, 154 mg/body/6 weeks, 154.5 mg/body/6 weeks, 155 mg/body/6 weeks, 155.5 mg/body/6 weeks, 156 mg/body/6 weeks, 156.5 mg/body/6 weeks, 157 mg/body/6 weeks, 157.5 mg/body/6 weeks, 158 mg/body/6 weeks, 158.5 mg/body/6 weeks, 159 mg/body/6 weeks, 159.5 mg/body/6 weeks, 160 mg/body/6 weeks, 160.5 mg/body/6 weeks, 161 mg/body/6 weeks, 161.5 mg/body/6 weeks, 162 mg/body/6 weeks, 162.5 mg/body/6 weeks, 163 mg/body/6 weeks, 163.5 mg/body/6 weeks, 164 mg/body/6 weeks, 164.5 mg/body/6 weeks, 165 mg/body/6 weeks, 165.5 mg/body/6 weeks, 166 mg/body/6 weeks, 166.5 mg/body/6 weeks, 167 mg/body/6 weeks, 167.5 mg/body/6 weeks, 168 mg/body/6 weeks, 168.5 mg/body/6 weeks, 169 mg/body/6 weeks, 169.5 mg/body/6 weeks, 170 mg/body/6 weeks, 170.5 mg/body/6 weeks, 171 mg/body/6 weeks, 171.5 mg/body/6 weeks, 172 mg/body/6 weeks, 172.5 mg/body/6 weeks, 173 mg/body/6 weeks, 173.5 mg/body/6 weeks, 174 mg/body/6 weeks, 174.5 mg/body/6 weeks, 175 mg/body/6 weeks, 175.5 mg/body/6 weeks, 176 mg/body/6 weeks, 176.5 mg/body/6 weeks, 177 mg/body/6 weeks, 177.5 mg/body/6 weeks, 178 mg/body/6 weeks, 178.5 mg/body/6 weeks, 179 mg/body/6 weeks, 179.5 mg/body/6 weeks, 180 mg/body/6 weeks, 180.5 mg/body/6 weeks, 181 mg/body/6 weeks, 181.5 mg/body/6 weeks, 182 mg/body/6 weeks, 182.5 mg/body/6 weeks, 183 mg/body/6 weeks, 183.5 mg/body/6 weeks, 184 mg/body/6 weeks, 184.5 mg/body/6 weeks, 185 mg/body/6 weeks, 185.5 mg/body/6 weeks, 186 mg/body/6 weeks, 186.5 mg/body/6 weeks, 187 mg/body/6 weeks, 187.5 mg/body/6 weeks, 188 mg/body/6 weeks, 188.5 mg/body/6 weeks, 189 mg/body/6 weeks, 189.5 mg/body/6 weeks, 190 mg/body/6 weeks, 190.5 mg/body/6 weeks, 191 mg/body/6 weeks, 191.5 mg/body/6 weeks, 192 mg/body/6 weeks, 192.5 mg/body/6 weeks, 193 mg/body/6 weeks, 193.5 mg/body/6 weeks, 194 mg/body/6 weeks, 194.5 mg/body/6 weeks, 195 mg/body/6 weeks, 195.5 mg/body/6 weeks, 196 mg/body/6 weeks, 196.5 mg/body/6 weeks, 197 mg/body/6 weeks, 197.5 mg/body/6 weeks, 198 mg/body/6 weeks, 198.5 mg/body/6 weeks, 199 mg/body/6 weeks, 199.5 mg/body/6 weeks, or 200 mg/body/6 weeks. Alternatively, in a non-limiting embodiment, the IL-31 antagonist of the present disclosure may be administered at, for example, 50 mg/body/8 weeks, 50.5 mg/body/8 weeks, 51 mg/body/8 weeks, 51.5 mg/body/8 weeks, 52 mg/body/8 weeks, 52.5 mg/body/8 weeks, 53 mg/body/8 weeks, 53.5 mg/body/8 weeks, 54 mg/body/8 weeks, 54.5 mg/body/8 weeks, 55 mg/body/8 weeks, 55.5 mg/body/8 weeks, 56 mg/body/8 weeks, 56.5 mg/body/8 weeks, 57 mg/body/8 weeks, 57.5 mg/body/8 weeks, 58 mg/body/8 weeks, 58.5 mg/body/8 weeks, 59 mg/body/8 weeks, 59.5 mg/body/8 weeks, 60 mg/body/8 weeks, 60.5 mg/body/8 weeks, 61 mg/body/8 weeks, 61.5 mg/body/8 weeks, 62 mg/body/8 weeks, 62.5 mg/body/8 weeks, 63 mg/body/8 weeks, 63.5 mg/body/8 weeks, 64 mg/body/8 weeks, 64.5 mg/body/8 weeks, 65 mg/body/8 weeks, 65.5 mg/body/8 weeks, 66 mg/body/8 weeks, 66.5 mg/body/8 weeks, 67 mg/body/8 weeks, 67.5 mg/body/8 weeks, 68 mg/body/8 weeks, 68.5 mg/body/8 weeks, 69 mg/body/8 weeks, 69.5 mg/body/8 weeks, 70 mg/body/8 weeks, 70.5 mg/body/8 weeks, 71 mg/body/8 weeks, 71.5 mg/body/8 weeks, 72 mg/body/8 weeks, 72.5 mg/body/8 weeks, 73 mg/body/8 weeks, 73.5 mg/body/8 weeks, 74 mg/body/8 weeks, 74.5 mg/body/8 weeks, 75 mg/body/8 weeks, 75.5 mg/body/8 weeks, 76 mg/body/8 weeks, 76.5 mg/body/8 weeks, 77 mg/body/8 weeks, 77.5 mg/body/8 weeks, 78 mg/body/8 weeks, 78.5 mg/body/8 weeks, 79 mg/body/8 weeks, 79.5 mg/body/8 weeks, 80 mg/body/8 weeks, 80.5 mg/body/8 weeks, 81 mg/body/8 weeks, 81.5 mg/body/8 weeks, 82 mg/body/8 weeks, 82.5 mg/body/8 weeks, 83 mg/body/8 weeks, 83.5 mg/body/8 weeks, 84 mg/body/8 weeks, 84.5 mg/body/8 weeks, 85 mg/body/8 weeks, 85.5 mg/body/8 weeks, 86 mg/body/8 weeks, 86.5 mg/body/8 weeks, 87 mg/body/8 weeks, 87.5 mg/body/8 weeks, 88 mg/body/8 weeks, 88.5 mg/body/8 weeks, 89 mg/body/8 weeks, 89.5 mg/body/8 weeks, 90 mg/body/8 weeks, 90.5 mg/body/8 weeks, 91 mg/body/8 weeks, 91.5 mg/body/8 weeks, 92 mg/body/8 weeks, 92.5 mg/body/8 weeks, 93 mg/body/8 weeks, 93.5 mg/body/8 weeks, 94 mg/body/8 weeks, 94.5 mg/body/8 weeks, 95 mg/body/8 weeks, 95.5 mg/body/8 weeks, 96 mg/body/8 weeks, 96.5 mg/body/8 weeks, 97 mg/body/8 weeks, 97.5 mg/body/8 weeks, 98 mg/body/8 weeks, 98.5 mg/body/8 weeks, 99 mg/body/8 weeks, 99.5 mg/body/8 weeks, 100 mg/body/8 weeks, 100.5 mg/body/8 weeks, 101 mg/body/8 weeks, 101.5 mg/body/8 weeks, 102 mg/body/8 weeks, 102.5 mg/body/8 weeks, 103 mg/body/8 weeks, 103.5 mg/body/8 weeks, 104 mg/body/8 weeks, 104.5 mg/body/8 weeks, 105 mg/body/8 weeks, 105.5 mg/body/8 weeks, 106 mg/body/8 weeks, 106.5 mg/body/8 weeks, 107 mg/body/8 weeks, 107.5 mg/body/8 weeks, 108 mg/body/8 weeks, 108.5 mg/body/8 weeks, 109 mg/body/8 weeks, 109.5 mg/body/8 weeks, 110 mg/body/8 weeks, 110.5 mg/body/8 weeks, 111 mg/body/8 weeks, 111.5 mg/body/8 weeks, 112 mg/body/8 weeks, 112.5 mg/body/8 weeks, 113 mg/body/8 weeks, 113.5 mg/body/8 weeks, 114 mg/body/8 weeks, 114.5 mg/body/8 weeks, 115 mg/body/8 weeks, 115.5 mg/body/8 weeks, 116 mg/body/8 weeks, 116.5 mg/body/8 weeks, 117 mg/body/8 weeks, 117.5 mg/body/8 weeks, 118 mg/body/8 weeks, 118.5 mg/body/8 weeks, 119 mg/body/8 weeks, 119.5 mg/body/8 weeks, 120 mg/body/8 weeks, 120.5 mg/body/8 weeks, 121 mg/body/8 weeks, 121.5 mg/body/8 weeks, 122 mg/body/8 weeks, 122.5 mg/body/8 weeks, 123 mg/body/8 weeks, 123.5 mg/body/8 weeks, 124 mg/body/8 weeks, 124.5 mg/body/8 weeks, 125 mg/body/8 weeks, 125.5 mg/body/8 weeks, 126 mg/body/8 weeks, 126.5 mg/body/8 weeks, 127 mg/body/8 weeks, 127.5 mg/body/8 weeks, 128 mg/body/8 weeks, 128.5 mg/body/8 weeks, 129 mg/body/8 weeks, 129.5 mg/body/8 weeks, 130 mg/body/8 weeks, 130.5 mg/body/8 weeks, 131 mg/body/8 weeks, 131.5 mg/body/8 weeks, 132 mg/body/8 weeks, 132.5 mg/body/8 weeks, 133 mg/body/8 weeks, 133.5 mg/body/8 weeks, 134 mg/body/8 weeks, 134.5 mg/body/8 weeks, 135 mg/body/8 weeks, 135.5 mg/body/8 weeks, 136 mg/body/8 weeks, 136.5 mg/body/8 weeks, 137 mg/body/8 weeks, 137.5 mg/body/8 weeks, 138 mg/body/8 weeks, 138.5 mg/body/8 weeks, 139 mg/body/8 weeks, 139.5 mg/body/8 weeks, 140 mg/body/8 weeks, 140.5 mg/body/8 weeks, 141 mg/body/8 weeks, 141.5 mg/body/8 weeks, 142 mg/body/8 weeks, 142.5 mg/body/8 weeks, 143 mg/body/8 weeks, 143.5 mg/body/8 weeks, 144 mg/body/8 weeks, 144.5 mg/body/8 weeks, 145 mg/body/8 weeks, 145.5 mg/body/8 weeks, 146 mg/body/8 weeks, 146.5 mg/body/8 weeks, 147 mg/body/8 weeks, 147.5 mg/body/8 weeks, 148 mg/body/8 weeks, 148.5 mg/body/8 weeks, 149 mg/body/8 weeks, 149.5 mg/body/8 weeks, 150 mg/body/8 weeks, 150.5 mg/body/8 weeks, 151 mg/body/8 weeks, 151.5 mg/body/8 weeks, 152 mg/body/8 weeks, 152.5 mg/body/8 weeks, 153 mg/body/8 weeks, 153.5 mg/body/8 weeks, 154 mg/body/8 weeks, 154.5 mg/body/8 weeks, 155 mg/body/8 weeks, 155.5 mg/body/8 weeks, 156 mg/body/8 weeks, 156.5 mg/body/8 weeks, 157 mg/body/8 weeks, 157.5 mg/body/8 weeks, 158 mg/body/8 weeks, 158.5 mg/body/8 weeks, 159 mg/body/8 weeks, 159.5 mg/body/8 weeks, 160 mg/body/8 weeks, 160.5 mg/body/8 weeks, 161 mg/body/8 weeks, 161.5 mg/body/8 weeks, 162 mg/body/8 weeks, 162.5 mg/body/8 weeks, 163 mg/body/8 weeks, 163.5 mg/body/8 weeks, 164 mg/body/8 weeks, 164.5 mg/body/8 weeks, 165 mg/body/8 weeks, 165.5 mg/body/8 weeks, 166 mg/body/8 weeks, 166.5 mg/body/8 weeks, 167 mg/body/8 weeks, 167.5 mg/body/8 weeks, 168 mg/body/8 weeks, 168.5 mg/body/8 weeks, 169 mg/body/8 weeks, 169.5 mg/body/8 weeks, 170 mg/body/8 weeks, 170.5 mg/body/8 weeks, 171 mg/body/8 weeks, 171.5 mg/body/8 weeks, 172 mg/body/8 weeks, 172.5 mg/body/8 weeks, 173 mg/body/8 weeks, 173.5 mg/body/8 weeks, 174 mg/body/8 weeks, 174.5 mg/body/8 weeks, 175 mg/body/8 weeks, 175.5 mg/body/8 weeks, 176 mg/body/8 weeks, 176.5 mg/body/8 weeks, 177 mg/body/8 weeks, 177.5 mg/body/8 weeks, 178 mg/body/8 weeks, 178.5 mg/body/8 weeks, 179 mg/body/8 weeks, 179.5 mg/body/8 weeks, 180 mg/body/8 weeks, 180.5 mg/body/8 weeks, 181 mg/body/8 weeks, 181.5 mg/body/8 weeks, 182 mg/body/8 weeks, 182.5 mg/body/8 weeks, 183 mg/body/8 weeks, 183.5 mg/body/8 weeks, 184 mg/body/8 weeks, 184.5 mg/body/8 weeks, 185 mg/body/8 weeks, 185.5 mg/body/8 weeks, 186 mg/body/8 weeks, 186.5 mg/body/8 weeks, 187 mg/body/8 weeks, 187.5 mg/body/8 weeks, 188 mg/body/8 weeks, 188.5 mg/body/8 weeks, 189 mg/body/8 weeks, 189.5 mg/body/8 weeks, 190 mg/body/8 weeks, 190.5 mg/body/8 weeks, 191 mg/body/8 weeks, 191.5 mg/body/8 weeks, 192 mg/body/8 weeks, 192.5 mg/body/8 weeks, 193 mg/body/8 weeks, 193.5 mg/body/8 weeks, 194 mg/body/8 weeks, 194.5 mg/body/8 weeks, 195 mg/body/8 weeks, 195.5 mg/body/8 weeks, 196 mg/body/8 weeks, 196.5 mg/body/8 weeks, 197 mg/body/8 weeks, 197.5 mg/body/8 weeks, 198 mg/body/8 weeks, 198.5 mg/body/8 weeks, 199 mg/body/8 weeks, 199.5 mg/body/8 weeks, or 200 mg/body/8 weeks. Alternatively, in a non-limiting embodiment, the IL-31 antagonist of the present disclosure may be administered at, for example, 50 mg/body/10 weeks, 50.5 mg/body/10 weeks, 51 mg/body/10 weeks, 51.5 mg/body/10 weeks, 52 mg/body/10 weeks, 52.5 mg/body/10 weeks, 53 mg/body/10 weeks, 53.5 mg/body/10 weeks, 54 mg/body/10 weeks, 54.5 mg/body/10 weeks, 55 mg/body/10 weeks, 55.5 mg/body/10 weeks, 56 mg/body/10 weeks, 56.5 mg/body/10 weeks, 57 mg/body/10 weeks, 57.5 mg/body/10 weeks, 58 mg/body/10 weeks, 58.5 mg/body/10 weeks, 59 mg/body/10 weeks, 59.5 mg/body/10 weeks, 60 mg/body/10 weeks, 60.5 mg/body/10 weeks, 61 mg/body/10 weeks, 61.5 mg/body/10 weeks, 62 mg/body/10 weeks, 62.5 mg/body/10 weeks, 63 mg/body/10 weeks, 63.5 mg/body/10 weeks, 64 mg/body/10 weeks, 64.5 mg/body/10 weeks, 65 mg/body/10 weeks, 65.5 mg/body/10 weeks, 66 mg/body/10 weeks, 66.5 mg/body/10 weeks, 67 mg/body/10 weeks, 67.5 mg/body/10 weeks, 68 mg/body/10 weeks, 68.5 mg/body/10 weeks, 69 mg/body/10 weeks, 69.5 mg/body/10 weeks, 70 mg/body/10 weeks, 70.5 mg/body/10 weeks, 71 mg/body/10 weeks, 71.5 mg/body/10 weeks, 72 mg/body/10 weeks, 72.5 mg/body/10 weeks, 73 mg/body/10 weeks, 73.5 mg/body/10 weeks, 74 mg/body/10 weeks, 74.5 mg/body/10 weeks, 75 mg/body/10 weeks, 75.5 mg/body/10 weeks, 76 mg/body/10 weeks, 76.5 mg/body/10 weeks, 77 mg/body/10 weeks, 77.5 mg/body/10 weeks, 78 mg/body/10 weeks, 78.5 mg/body/10 weeks, 79 mg/body/10 weeks, 79.5 mg/body/10 weeks, 80 mg/body/10 weeks, 80.5 mg/body/10 weeks, 81 mg/body/10 weeks, 81.5 mg/body/10 weeks, 82 mg/body/10 weeks, 82.5 mg/body/10 weeks, 83 mg/body/10 weeks, 83.5 mg/body/10 weeks, 84 mg/body/10 weeks, 84.5 mg/body/10 weeks, 85 mg/body/10 weeks, 85.5 mg/body/10 weeks, 86 mg/body/10 weeks, 86.5 mg/body/10 weeks, 87 mg/body/10 weeks, 87.5 mg/body/10 weeks, 88 mg/body/10 weeks, 88.5 mg/body/10 weeks, 89 mg/body/10 weeks, 89.5 mg/body/10 weeks, 90 mg/body/10 weeks, 90.5 mg/body/10 weeks, 91 mg/body/10 weeks, 91.5 mg/body/10 weeks, 92 mg/body/10 weeks, 92.5 mg/body/10 weeks, 93 mg/body/10 weeks, 93.5 mg/body/10 weeks, 94 mg/body/10 weeks, 94.5 mg/body/10 weeks, 95 mg/body/10 weeks, 95.5 mg/body/10 weeks, 96 mg/body/10 weeks, 96.5 mg/body/10 weeks, 97 mg/body/10 weeks, 97.5 mg/body/10 weeks, 98 mg/body/10 weeks, 98.5 mg/body/10 weeks, 99 mg/body/10 weeks, 99.5 mg/body/10 weeks, 100 mg/body/10 weeks, 100.5 mg/body/10 weeks, 101 mg/body/10 weeks, 101.5 mg/body/10 weeks, 102 mg/body/10 weeks, 102.5 mg/body/10 weeks, 103 mg/body/10 weeks, 103.5 mg/body/10 weeks, 104 mg/body/10 weeks, 104.5 mg/body/10 weeks, 105 mg/body/10 weeks, 105.5 mg/body/10 weeks, 106 mg/body/10 weeks, 106.5 mg/body/10 weeks, 107 mg/body/10 weeks, 107.5 mg/body/10 weeks, 108 mg/body/10 weeks, 108.5 mg/body/10 weeks, 109 mg/body/10 weeks, 109.5 mg/body/10 weeks, 110 mg/body/10 weeks, 110.5 mg/body/10 weeks, 111 mg/body/10 weeks, 111.5 mg/body/10 weeks, 112 mg/body/10 weeks, 112.5 mg/body/10 weeks, 113 mg/body/10 weeks, 113.5 mg/body/10 weeks, 114 mg/body/10 weeks, 114.5 mg/body/10 weeks, 115 mg/body/10 weeks, 115.5 mg/body/10 weeks, 116 mg/body/10 weeks, 116.5 mg/body/10 weeks, 117 mg/body/10 weeks, 117.5 mg/body/10 weeks, 118 mg/body/10 weeks, 118.5 mg/body/10 weeks, 119 mg/body/10 weeks, 119.5 mg/body/10 weeks, 120 mg/body/10 weeks, 120.5 mg/body/10 weeks, 121 mg/body/10 weeks, 121.5 mg/body/10 weeks, 122 mg/body/10 weeks, 122.5 mg/body/10 weeks, 123 mg/body/10 weeks, 123.5 mg/body/10 weeks, 124 mg/body/10 weeks, 124.5 mg/body/10 weeks, 125 mg/body/10 weeks, 125.5 mg/body/10 weeks, 126 mg/body/10 weeks, 126.5 mg/body/10 weeks, 127 mg/body/10 weeks, 127.5 mg/body/10 weeks, 128 mg/body/10 weeks, 128.5 mg/body/10 weeks, 129 mg/body/10 weeks, 129.5 mg/body/10 weeks, 130 mg/body/10 weeks, 130.5 mg/body/10 weeks, 131 mg/body/10 weeks, 131.5 mg/body/10 weeks, 132 mg/body/10 weeks, 132.5 mg/body/10 weeks, 133 mg/body/10 weeks, 133.5 mg/body/10 weeks, 134 mg/body/10 weeks, 134.5 mg/body/10 weeks, 135 mg/body/10 weeks, 135.5 mg/body/10 weeks, 136 mg/body/10 weeks, 136.5 mg/body/10 weeks, 137 mg/body/10 weeks, 137.5 mg/body/10 weeks, 138 mg/body/10 weeks, 138.5 mg/body/10 weeks, 139 mg/body/10 weeks, 139.5 mg/body/10 weeks, 140 mg/body/10 weeks, 140.5 mg/body/10 weeks, 141 mg/body/10 weeks, 141.5 mg/body/10 weeks, 142 mg/body/10 weeks, 142.5 mg/body/10 weeks, 143 mg/body/10 weeks, 143.5 mg/body/10 weeks, 144 mg/body/10 weeks, 144.5 mg/body/10 weeks, 145 mg/body/10 weeks, 145.5 mg/body/10 weeks, 146 mg/body/10 weeks, 146.5 mg/body/10 weeks, 147 mg/body/10 weeks, 147.5 mg/body/10 weeks, 148 mg/body/10 weeks, 148.5 mg/body/10 weeks, 149 mg/body/10 weeks, 149.5 mg/body/10 weeks, 150 mg/body/10 weeks, 150.5 mg/body/10 weeks, 151 mg/body/10 weeks, 151.5 mg/body/10 weeks, 152 mg/body/10 weeks, 152.5 mg/body/10 weeks, 153 mg/body/10 weeks, 153.5 mg/body/10 weeks, 154 mg/body/10 weeks, 154.5 mg/body/10 weeks, 155 mg/body/10 weeks, 155.5 mg/body/10 weeks, 156 mg/body/10 weeks, 156.5 mg/body/10 weeks, 157 mg/body/10 weeks, 157.5 mg/body/10 weeks, 158 mg/body/10 weeks, 158.5 mg/body/10 weeks, 159 mg/body/10 weeks, 159.5 mg/body/10 weeks, 160 mg/body/10 weeks, 160.5 mg/body/10 weeks, 161 mg/body/10 weeks, 161.5 mg/body/10 weeks, 162 mg/body/10 weeks, 162.5 mg/body/10 weeks, 163 mg/body/10 weeks, 163.5 mg/body/10 weeks, 164 mg/body/10 weeks, 164.5 mg/body/10 weeks, 165 mg/body/10 weeks, 165.5 mg/body/10 weeks, 166 mg/body/10 weeks, 166.5 mg/body/10 weeks, 167 mg/body/10 weeks, 167.5 mg/body/10 weeks, 168 mg/body/10 weeks, 168.5 mg/body/10 weeks, 169 mg/body/10 weeks, 169.5 mg/body/10 weeks, 170 mg/body/10 weeks, 170.5 mg/body/10 weeks, 171 mg/body/10 weeks, 171.5 mg/body/10 weeks, 172 mg/body/10 weeks, 172.5 mg/body/10 weeks, 173 mg/body/10 weeks, 173.5 mg/body/10 weeks, 174 mg/body/10 weeks, 174.5 mg/body/10 weeks, 175 mg/body/10 weeks, 175.5 mg/body/10 weeks, 176 mg/body/10 weeks, 176.5 mg/body/10 weeks, 177 mg/body/10 weeks, 177.5 mg/body/10 weeks, 178 mg/body/10 weeks, 178.5 mg/body/10 weeks, 179 mg/body/10 weeks, 179.5 mg/body/10 weeks, 180 mg/body/10 weeks, 180.5 mg/body/10 weeks, 181 mg/body/10 weeks, 181.5 mg/body/10 weeks, 182 mg/body/10 weeks, 182.5 mg/body/10 weeks, 183 mg/body/10 weeks, 183.5 mg/body/10 weeks, 184 mg/body/10 weeks, 184.5 mg/body/10 weeks, 185 mg/body/10 weeks, 185.5 mg/body/10 weeks, 186 mg/body/10 weeks, 186.5 mg/body/10 weeks, 187 mg/body/10 weeks, 187.5 mg/body/10 weeks, 188 mg/body/10 weeks, 188.5 mg/body/10 weeks, 189 mg/body/10 weeks, 189.5 mg/body/10 weeks, 190 mg/body/10 weeks, 190.5 mg/body/10 weeks, 191 mg/body/10 weeks, 191.5 mg/body/10 weeks, 192 mg/body/10 weeks, 192.5 mg/body/10 weeks, 193 mg/body/10 weeks, 193.5 mg/body/10 weeks, 194 mg/body/10 weeks, 194.5 mg/body/10 weeks, 195 mg/body/10 weeks, 195.5 mg/body/10 weeks, 196 mg/body/10 weeks, 196.5 mg/body/10 weeks, 197 mg/body/10 weeks, 197.5 mg/body/10 weeks, 198 mg/body/10 weeks, 198.5 mg/body/10 weeks, 199 mg/body/10 weeks, 199.5 mg/body/10 weeks, or 200 mg/body/10 weeks. Alternatively, in a non-limiting embodiment, the IL-31 antagonist of the present disclosure may be administered at, for example, 50 mg/body/12 weeks, 50.5 mg/body/12 weeks, 51 mg/body/12 weeks, 51.5 mg/body/12 weeks, 52 mg/body/12 weeks, 52.5 mg/body/12 weeks, 53 mg/body/12 weeks, 53.5 mg/body/12 weeks, 54 mg/body/12 weeks, 54.5 mg/body/12 weeks, 55 mg/body/12 weeks, 55.5 mg/body/12 weeks, 56 mg/body/12 weeks, 56.5 mg/body/12 weeks, 57 mg/body/12 weeks, 57.5 mg/body/12 weeks, 58 mg/body/12 weeks, 58.5 mg/body/12 weeks, 59 mg/body/12 weeks, 59.5 mg/body/12 weeks, 60 mg/body/12 weeks, 60.5 mg/body/12 weeks, 61 mg/body/12 weeks, 61.5 mg/body/12 weeks, 62 mg/body/12 weeks, 62.5 mg/body/12 weeks, 63 mg/body/12 weeks, 63.5 mg/body/12 weeks, 64 mg/body/12 weeks, 64.5 mg/body/12 weeks, 65 mg/body/12 weeks, 65.5 mg/body/12 weeks, 66 mg/body/12 weeks, 66.5 mg/body/12 weeks, 67 mg/body/12 weeks, 67.5 mg/body/12 weeks, 68 mg/body/12 weeks, 68.5 mg/body/12 weeks, 69 mg/body/12 weeks, 69.5 mg/body/12 weeks, 70 mg/body/12 weeks, 70.5 mg/body/12 weeks, 71 mg/body/12 weeks, 71.5 mg/body/12 weeks, 72 mg/body/12 weeks, 72.5 mg/body/12 weeks, 73 mg/body/12 weeks, 73.5 mg/body/12 weeks, 74 mg/body/12 weeks, 74.5 mg/body/12 weeks, 75 mg/body/12 weeks, 75.5 mg/body/12 weeks, 76 mg/body/12 weeks, 76.5 mg/body/12 weeks, 77 mg/body/12 weeks, 77.5 mg/body/12 weeks, 78 mg/body/12 weeks, 78.5 mg/body/12 weeks, 79 mg/body/12 weeks, 79.5 mg/body/12 weeks, 80 mg/body/12 weeks, 80.5 mg/body/12 weeks, 81 mg/body/12 weeks, 81.5 mg/body/12 weeks, 82 mg/body/12 weeks, 82.5 mg/body/12 weeks, 83 mg/body/12 weeks, 83.5 mg/body/12 weeks, 84 mg/body/12 weeks, 84.5 mg/body/12 weeks, 85 mg/body/12 weeks, 85.5 mg/body/12 weeks, 86 mg/body/12 weeks, 86.5 mg/body/12 weeks, 87 mg/body/12 weeks, 87.5 mg/body/12 weeks, 88 mg/body/12 weeks, 88.5 mg/body/12 weeks, 89 mg/body/12 weeks, 89.5 mg/body/12 weeks, 90 mg/body/12 weeks, 90.5 mg/body/12 weeks, 91 mg/body/12 weeks, 91.5 mg/body/12 weeks, 92 mg/body/12 weeks, 92.5 mg/body/12 weeks, 93 mg/body/12 weeks, 93.5 mg/body/12 weeks, 94 mg/body/12 weeks, 94.5 mg/body/12 weeks, 95 mg/body/12 weeks, 95.5 mg/body/12 weeks, 96 mg/body/12 weeks, 96.5 mg/body/12 weeks, 97 mg/body/12 weeks, 97.5 mg/body/12 weeks, 98 mg/body/12 weeks, 98.5 mg/body/12 weeks, 99 mg/body/12 weeks, 99.5 mg/body/12 weeks, 100 mg/body/12 weeks, 100.5 mg/body/12 weeks, 101 mg/body/12 weeks, 101.5 mg/body/12 weeks, 102 mg/body/12 weeks, 102.5 mg/body/12 weeks, 103 mg/body/12 weeks, 103.5 mg/body/12 weeks, 104 mg/body/12 weeks, 104.5 mg/body/12 weeks, 105 mg/body/12 weeks, 105.5 mg/body/12 weeks, 106 mg/body/12 weeks, 106.5 mg/body/12 weeks, 107 mg/body/12 weeks, 107.5 mg/body/12 weeks, 108 mg/body/12 weeks, 108.5 mg/body/12 weeks, 109 mg/body/12 weeks, 109.5 mg/body/12 weeks, 110 mg/body/12 weeks, 110.5 mg/body/12 weeks, 111 mg/body/12 weeks, 111.5 mg/body/12 weeks, 112 mg/body/12 weeks, 112.5 mg/body/12 weeks, 113 mg/body/12 weeks, 113.5 mg/body/12 weeks, 114 mg/body/12 weeks, 114.5 mg/body/12 weeks, 115 mg/body/12 weeks, 115.5 mg/body/12 weeks, 116 mg/body/12 weeks, 116.5 mg/body/12 weeks, 117 mg/body/12 weeks, 117.5 mg/body/12 weeks, 118 mg/body/12 weeks, 118.5 mg/body/12 weeks, 119 mg/body/12 weeks, 119.5 mg/body/12 weeks, 120 mg/body/12 weeks, 120.5 mg/body/12 weeks, 121 mg/body/12 weeks, 121.5 mg/body/12 weeks, 122 mg/body/12 weeks, 122.5 mg/body/12 weeks, 123 mg/body/12 weeks, 123.5 mg/body/12 weeks, 124 mg/body/12 weeks, 124.5 mg/body/12 weeks, 125 mg/body/12 weeks, 125.5 mg/body/12 weeks, 126 mg/body/12 weeks, 126.5 mg/body/12 weeks, 127 mg/body/12 weeks, 127.5 mg/body/12 weeks, 128 mg/body/12 weeks, 128.5 mg/body/12 weeks, 129 mg/body/12 weeks, 129.5 mg/body/12 weeks, 130 mg/body/12 weeks, 130.5 mg/body/12 weeks, 131 mg/body/12 weeks, 131.5 mg/body/12 weeks, 132 mg/body/12 weeks, 132.5 mg/body/12 weeks, 133 mg/body/12 weeks, 133.5 mg/body/12 weeks, 134 mg/body/12 weeks, 134.5 mg/body/12 weeks, 135 mg/body/12 weeks, 135.5 mg/body/12 weeks, 136 mg/body/12 weeks, 136.5 mg/body/12 weeks, 137 mg/body/12 weeks, 137.5 mg/body/12 weeks, 138 mg/body/12 weeks, 138.5 mg/body/12 weeks, 139 mg/body/12 weeks, 139.5 mg/body/12 weeks, 140 mg/body/12 weeks, 140.5 mg/body/12 weeks, 141 mg/body/12 weeks, 141.5 mg/body/12 weeks, 142 mg/body/12 weeks, 142.5 mg/body/12 weeks, 143 mg/body/12 weeks, 143.5 mg/body/12 weeks, 144 mg/body/12 weeks, 144.5 mg/body/12 weeks, 145 mg/body/12 weeks, 145.5 mg/body/12 weeks, 146 mg/body/12 weeks, 146.5 mg/body/12 weeks, 147 mg/body/12 weeks, 147.5 mg/body/12 weeks, 148 mg/body/12 weeks, 148.5 mg/body/12 weeks, 149 mg/body/12 weeks, 149.5 mg/body/12 weeks, 150 mg/body/12 weeks, 150.5 mg/body/12 weeks, 151 mg/body/12 weeks, 151.5 mg/body/12 weeks, 152 mg/body/12 weeks, 152.5 mg/body/12 weeks, 153 mg/body/12 weeks, 153.5 mg/body/12 weeks, 154 mg/body/12 weeks, 154.5 mg/body/12 weeks, 155 mg/body/12 weeks, 155.5 mg/body/12 weeks, 156 mg/body/12 weeks, 156.5 mg/body/12 weeks, 157 mg/body/12 weeks, 157.5 mg/body/12 weeks, 158 mg/body/12 weeks, 158.5 mg/body/12 weeks, 159 mg/body/12 weeks, 159.5 mg/body/12 weeks, 160 mg/body/12 weeks, 160.5 mg/body/12 weeks, 161 mg/body/12 weeks, 161.5 mg/body/12 weeks, 162 mg/body/12 weeks, 162.5 mg/body/12 weeks, 163 mg/body/12 weeks, 163.5 mg/body/12 weeks, 164 mg/body/12 weeks, 164.5 mg/body/12 weeks, 165 mg/body/12 weeks, 165.5 mg/body/12 weeks, 166 mg/body/12 weeks, 166.5 mg/body/12 weeks, 167 mg/body/12 weeks, 167.5 mg/body/12 weeks, 168 mg/body/12 weeks, 168.5 mg/body/12 weeks, 169 mg/body/12 weeks, 169.5 mg/body/12 weeks, 170 mg/body/12 weeks, 170.5 mg/body/12 weeks, 171 mg/body/12 weeks, 171.5 mg/body/12 weeks, 172 mg/body/12 weeks, 172.5 mg/body/12 weeks, 173 mg/body/12 weeks, 173.5 mg/body/12 weeks, 174 mg/body/12 weeks, 174.5 mg/body/12 weeks, 175 mg/body/12 weeks, 175.5 mg/body/12 weeks, 176 mg/body/12 weeks, 176.5 mg/body/12 weeks, 177 mg/body/12 weeks, 177.5 mg/body/12 weeks, 178 mg/body/12 weeks, 178.5 mg/body/12 weeks, 179 mg/body/12 weeks, 179.5 mg/body/12 weeks, 180 mg/body/12 weeks, 180.5 mg/body/12 weeks, 181 mg/body/12 weeks, 181.5 mg/body/12 weeks, 182 mg/body/12 weeks, 182.5 mg/body/12 weeks, 183 mg/body/12 weeks, 183.5 mg/body/12 weeks, 184 mg/body/12 weeks, 184.5 mg/body/12 weeks, 185 mg/body/12 weeks, 185.5 mg/body/12 weeks, 186 mg/body/12 weeks, 186.5 mg/body/12 weeks, 187 mg/body/12 weeks, 187.5 mg/body/12 weeks, 188 mg/body/12 weeks, 188.5 mg/body/12 weeks, 189 mg/body/12 weeks, 189.5 mg/body/12 weeks, 190 mg/body/12 weeks, 190.5 mg/body/12 weeks, 191 mg/body/12 weeks, 191.5 mg/body/12 weeks, 192 mg/body/12 weeks, 192.5 mg/body/12 weeks, 193 mg/body/12 weeks, 193.5 mg/body/12 weeks, 194 mg/body/12 weeks, 194.5 mg/body/12 weeks, 195 mg/body/12 weeks, 195.5 mg/body/12 weeks, 196 mg/body/12 weeks, 196.5 mg/body/12 weeks, 197 mg/body/12 weeks, 197.5 mg/body/12 weeks, 198 mg/body/12 weeks, 198.5 mg/body/12 weeks, 199 mg/body/12 weeks, 199.5 mg/body/12 weeks, or 200 mg/body/12 weeks.

In a non-limiting embodiment, the IL-31 antagonist of the present disclosure is preferably administered at 25 to 100 mg/body/4 weeks, 50 to 100 mg/body/4 weeks, or 50 to 75 mg/body/4 weeks. In another non-limiting embodiment, the IL-31 antagonist of the present disclosure is preferably administered at 10 to 50 mg/body/2 weeks or 20 to 40 mg/body/2 weeks.

Alternatively, in an embodiment where the IL-31 antagonist of the present disclosure is repeatedly administered in equal amounts at the same dosing interval, using a predetermined dosing interval and a predetermined dose (dosage), the IL-31 antagonist of the present disclosure may be administered at "0.01 to 10 mg/kg/1 day to 12 weeks". As used herein, the recitation "0.01 to 10 mg/kg/1 day to 12 weeks", for example, is contemplated to mean that one dosage is selected from 0.01 to 10 mg as the dosage of the IL-31 antagonist of the present disclosure, and any one dosing interval is selected from 1 day to 12 weeks as the dosing interval (e.g., 4 weeks) of the IL-31 antagonist of the present disclosure, and the IL-31 antagonist is repeatedly administered to a subject in equal amounts at the same dosing interval. In an embodiment where the IL-31 antagonist of the present disclosure is repeatedly administered in equal amounts at the same dosing interval, using a predetermined dosing interval and a predetermined dose (dosage), the IL-31 antagonist of the present disclosure is preferably administered at 0.01 to 10 mg/kg/2 to 8 weeks, and may be administered at, for example, 0.01 to 10 mg/kg/2 weeks, 0.01 to 10 mg/kg/4 weeks, 0.01 to 10 mg/kg/6 weeks, or 0.01 to 10 mg/kg/8 weeks, but not limited thereto. Alternatively, the IL-31 antagonist of the present disclosure is more preferably administered at 0.1 to 3 mg/body/2 to 8 weeks, and may be administered at, for example, 0.1 to 3 mg/kg/2 weeks, 0.1 to 3 mg/kg/4 weeks, 0.1 to 3 mg/kg/6 weeks, or 0.1 to 3 mg/kg/8 weeks. Alternatively, as an example, the IL-31 antagonist of the present disclosure is more preferably administered at 0.2 to 2 mg/body/2 to 8 weeks, and may be administered at, for example, 0.2 to 2 mg/kg/2 weeks, 0.2 to 2 mg/kg/4 weeks, 0.2 to 2 mg/kg/6 weeks, or 0.2 to 2 mg/kg/8 weeks. Alternatively, as an example, the IL-31 antagonist of the present disclosure is more preferably administered at 0.5 to 1.5 mg/body/4 to 8 weeks, and may be administered at, for example, 0.5 to 1.5 mg/kg/4 weeks, 0.5 to 1.5 mg/kg/6 weeks, or 0.5 to 1.5 mg/kg/8 weeks. In a non-limiting embodiment, the IL-31 antagonist of the present disclosure may be administered at, for example, 0.1 mg/kg/4 weeks, 0.11 mg/kg/4 weeks, 0.12 mg/kg/4 weeks, 0.125 mg/kg/4 weeks, 0.13 mg/kg/4 weeks, 0.14 mg/kg/4 weeks, 0.15 mg/kg/4 weeks, 0.16 mg/kg/4 weeks, 0.17 mg/kg/4 weeks, 0.18 mg/kg/4 weeks, 0.19 mg/kg/4 weeks, 0.2 mg/kg/4 weeks, 0.21 mg/kg/4 weeks, 0.22 mg/kg/4 weeks, 0.23 mg/kg/4 weeks, 0.24 mg/kg/4 weeks, 0.25 mg/kg/4 weeks, 0.26 mg/kg/4 weeks, 0.27 mg/kg/4 weeks, 0.28 mg/kg/4 weeks, 0.29 mg/kg/4 weeks, 0.3 mg/kg/4 weeks, 0.31 mg/kg/4 weeks, 0.32 mg/kg/4 weeks, 0.33 mg/kg/4 weeks, 0.34 mg/kg/4 weeks, 0.35 mg/kg/4 weeks, 0.36 mg/kg/4 weeks, 0.37 mg/kg/4 weeks, 0.38 mg/kg/4 weeks, 0.39 mg/kg/4 weeks, 0.4 mg/kg/4 weeks, 0.41 mg/kg/4 weeks, 0.42 mg/kg/4 weeks, 0.43 mg/kg/4 weeks, 0.44 mg/kg/4 weeks, 0.45 mg/kg/4 weeks, 0.46 mg/kg/4 weeks, 0.47 mg/kg/4 weeks, 0.48 mg/kg/4 weeks, 0.49 mg/kg/4 weeks, 0.5 mg/kg/4 weeks, 0.51 mg/kg/4 weeks, 0.52 mg/kg/4 weeks, 0.53 mg/kg/4 weeks, 0.54 mg/kg/4 weeks, 0.55 mg/kg/4 weeks, 0.56 mg/kg/4 weeks, 0.57 mg/kg/4 weeks, 0.58 mg/kg/4 weeks, 0.59 mg/kg/4 weeks, 0.6 mg/kg/4 weeks, 0.61 mg/kg/4 weeks, 0.62 mg/kg/4 weeks, 0.63 mg/kg/4 weeks, 0.64 mg/kg/4 weeks, 0.65 mg/kg/4 weeks, 0.66 mg/kg/4 weeks, 0.67 mg/kg/4 weeks, 0.68 mg/kg/4 weeks, 0.69 mg/kg/4 weeks, 0.7 mg/kg/4 weeks, 0.71 mg/kg/4 weeks, 0.72 mg/kg/4 weeks, 0.73 mg/kg/4 weeks, 0.74 mg/kg/4 weeks, 0.75 mg/kg/4 weeks, 0.76 mg/kg/4 weeks, 0.77 mg/kg/4 weeks, 0.78 mg/kg/4 weeks, 0.79 mg/kg/4 weeks, 0.8 mg/kg/4 weeks, 0.81 mg/kg/4 weeks, 0.82 mg/kg/4 weeks, 0.83 mg/kg/4 weeks, 0.84 mg/kg/4 weeks, 0.85 mg/kg/4 weeks, 0.86 mg/kg/4 weeks, 0.87 mg/kg/4 weeks, 0.88 mg/kg/4 weeks, 0.89 mg/kg/4 weeks, 0.9 mg/kg/4 weeks, 0.91 mg/kg/4 weeks, 0.92 mg/kg/4 weeks, 0.93 mg/kg/4 weeks, 0.94 mg/kg/4 weeks, 0.95 mg/kg/4 weeks, 0.96 mg/kg/4 weeks, 0.97 mg/kg/4 weeks, 0.98 mg/kg/4 weeks, 0.99 mg/kg/4 weeks, 1 mg/kg/4 weeks, 1.01 mg/kg/4 weeks, 1.02 mg/kg/4 weeks, 1.03 mg/kg/4 weeks, 1.04 mg/kg/4 weeks, 1.05 mg/kg/4 weeks, 1.06 mg/kg/4 weeks, 1.07 mg/kg/4 weeks, 1.08 mg/kg/4 weeks, 1.09 mg/kg/4 weeks, 1.1 mg/kg/4 weeks, 1.11 mg/kg/4 weeks, 1.12 mg/kg/4 weeks, 1.13 mg/kg/4 weeks, 1.14 mg/kg/4 weeks, 1.15 mg/kg/4 weeks, 1.16 mg/kg/4 weeks, 1.17 mg/kg/4 weeks, 1.18 mg/kg/4 weeks, 1.19 mg/kg/4 weeks, 1.2 mg/kg/4 weeks, 1.21 mg/kg/4 weeks, 1.22 mg/kg/4 weeks, 1.23 mg/kg/4 weeks, 1.24 mg/kg/4 weeks, 1.25 mg/kg/4 weeks, 1.26 mg/kg/4 weeks, 1.27 mg/kg/4 weeks, 1.28 mg/kg/4 weeks, 1.29 mg/kg/4 weeks, 1.3 mg/kg/4 weeks, 1.31 mg/kg/4 weeks, 1.32 mg/kg/4 weeks, 1.33 mg/kg/4 weeks, 1.34 mg/kg/4 weeks, 1.35 mg/kg/4 weeks, 1.36 mg/kg/4 weeks, 1.37 mg/kg/4 weeks, 1.38 mg/kg/4 weeks, 1.39 mg/kg/4 weeks, 1.4 mg/kg/4 weeks, 1.41 mg/kg/4 weeks, 1.42 mg/kg/4 weeks, 1.43 mg/kg/4 weeks, 1.44 mg/kg/4 weeks, 1.45 mg/kg/4 weeks, 1.46 mg/kg/4 weeks, 1.47 mg/kg/4 weeks, 1.48 mg/kg/4 weeks, 1.49 mg/kg/4 weeks, 1.5 mg/kg/4 weeks, 1.51 mg/kg/4 weeks, 1.52 mg/kg/4 weeks, 1.53 mg/kg/4 weeks, 1.54 mg/kg/4 weeks, 1.55 mg/kg/4 weeks, 1.56 mg/kg/4 weeks, 1.57 mg/kg/4 weeks, 1.58 mg/kg/4 weeks, 1.59 mg/kg/4 weeks, 1.6 mg/kg/4 weeks, 1.61 mg/kg/4 weeks, 1.62 mg/kg/4 weeks, 1.63 mg/kg/4 weeks, 1.64 mg/kg/4 weeks, 1.65 mg/kg/4 weeks, 1.66 mg/kg/4 weeks, 1.67 mg/kg/4 weeks, 1.68 mg/kg/4 weeks, 1.69 mg/kg/4 weeks, 1.7 mg/kg/4 weeks, 1.71 mg/kg/4 weeks, 1.72 mg/kg/4 weeks, 1.73 mg/kg/4 weeks, 1.74 mg/kg/4 weeks, 1.75 mg/kg/4 weeks, 1.76 mg/kg/4 weeks, 1.77 mg/kg/4 weeks, 1.78 mg/kg/4 weeks, 1.79 mg/kg/4 weeks, 1.8 mg/kg/4 weeks, 1.81 mg/kg/4 weeks, 1.82 mg/kg/4 weeks, 1.83 mg/kg/4 weeks, 1.84 mg/kg/4 weeks, 1.85 mg/kg/4 weeks, 1.86 mg/kg/4 weeks, 1.87 mg/kg/4 weeks, 1.88 mg/kg/4 weeks, 1.89 mg/kg/4 weeks, 1.9 mg/kg/4 weeks, 1.91 mg/kg/4 weeks, 1.92 mg/kg/4 weeks, 1.93 mg/kg/4 weeks, 1.94 mg/kg/4 weeks, 1.95 mg/kg/4 weeks, 1.96 mg/kg/4 weeks, 1.97 mg/kg/4 weeks, 1.98 mg/kg/4 weeks, 1.99 mg/kg/4 weeks, 2 mg/kg/4 weeks, 2.01 mg/kg/4 weeks, 2.02 mg/kg/4 weeks, 2.03 mg/kg/4 weeks, 2.04 mg/kg/4 weeks, 2.05 mg/kg/4 weeks, 2.06 mg/kg/4 weeks, 2.07 mg/kg/4 weeks, 2.08 mg/kg/4 weeks, 2.09 mg/kg/4 weeks, 2.1 mg/kg/4 weeks, 2.11 mg/kg/4 weeks, 2.12 mg/kg/4 weeks, 2.13 mg/kg/4 weeks, 2.14 mg/kg/4 weeks, 2.15 mg/kg/4 weeks, 2.16 mg/kg/4 weeks, 2.17 mg/kg/4 weeks, 2.18 mg/kg/4 weeks, 2.19 mg/kg/4 weeks, 2.2 mg/kg/4 weeks, 2.21 mg/kg/4 weeks, 2.22 mg/kg/4 weeks, 2.23 mg/kg/4 weeks, 2.24 mg/kg/4 weeks, 2.25 mg/kg/4 weeks, 2.26 mg/kg/4 weeks, 2.27 mg/kg/4 weeks, 2.28 mg/kg/4 weeks, 2.29 mg/kg/4 weeks, 2.3 mg/kg/4 weeks, 2.31 mg/kg/4 weeks, 2.32 mg/kg/4 weeks, 2.33 mg/kg/4 weeks, 2.34 mg/kg/4 weeks, 2.35 mg/kg/4 weeks, 2.36 mg/kg/4 weeks, 2.37 mg/kg/4 weeks, 2.38 mg/kg/4 weeks, 2.39 mg/kg/4 weeks, 2.4 mg/kg/4 weeks, 2.41 mg/kg/4 weeks, 2.42 mg/kg/4 weeks, 2.43 mg/kg/4 weeks, 2.44 mg/kg/4 weeks, 2.45 mg/kg/4 weeks, 2.46 mg/kg/4 weeks, 2.47 mg/kg/4 weeks, 2.48 mg/kg/4 weeks, 2.49 mg/kg/4 weeks, 2.5 mg/kg/4 weeks, 2.51 mg/kg/4 weeks, 2.52 mg/kg/4 weeks, 2.53 mg/kg/4 weeks, 2.54 mg/kg/4 weeks, 2.55 mg/kg/4 weeks, 2.56 mg/kg/4 weeks, 2.57 mg/kg/4 weeks, 2.58 mg/kg/4 weeks, 2.59 mg/kg/4 weeks, 2.6 mg/kg/4 weeks, 2.61 mg/kg/4 weeks, 2.62 mg/kg/4 weeks, 2.63 mg/kg/4 weeks, 2.64 mg/kg/4 weeks, 2.65 mg/kg/4 weeks, 2.66 mg/kg/4 weeks, 2.67 mg/kg/4 weeks, 2.68 mg/kg/4 weeks, 2.69 mg/kg/4 weeks, 2.7 mg/kg/4 weeks, 2.71 mg/kg/4 weeks, 2.72 mg/kg/4 weeks, 2.73 mg/kg/4 weeks, 2.74 mg/kg/4 weeks, 2.75 mg/kg/4 weeks, 2.76 mg/kg/4 weeks, 2.77 mg/kg/4 weeks, 2.78 mg/kg/4 weeks, 2.79 mg/kg/4 weeks, 2.8 mg/kg/4 weeks, 2.81 mg/kg/4 weeks, 2.82 mg/kg/4 weeks, 2.83 mg/kg/4 weeks, 2.84 mg/kg/4 weeks, 2.85 mg/kg/4 weeks, 2.86 mg/kg/4 weeks, 2.87 mg/kg/4 weeks, 2.88 mg/kg/4 weeks, 2.89 mg/kg/4 weeks, 2.9 mg/kg/4 weeks, 2.91 mg/kg/4 weeks, 2.92 mg/kg/4 weeks, 2.93 mg/kg/4 weeks, 2.94 mg/kg/4 weeks, 2.95 mg/kg/4 weeks, 2.96 mg/kg/4 weeks, 2.97 mg/kg/4 weeks, 2.98 mg/kg/4 weeks, 2.99 mg/kg/4 weeks, or 3 mg/kg/4 weeks. Alternatively, in a non-limiting embodiment, the IL-31 antagonist of the present disclosure may be administered at, for example, 0.1 mg/kg/6 weeks, 0.11 mg/kg/6 weeks, 0.12 mg/kg/6 weeks, 0.125 mg/kg/6 weeks, 0.13 mg/kg/6 weeks, 0.14 mg/kg/6 weeks, 0.15 mg/kg/6 weeks, 0.16 mg/kg/6 weeks, 0.17 mg/kg/6 weeks, 0.18 mg/kg/6 weeks, 0.19 mg/kg/6 weeks, 0.2 mg/kg/6 weeks, 0.21 mg/kg/6 weeks, 0.22 mg/kg/6 weeks, 0.23 mg/kg/6 weeks, 0.24 mg/kg/6 weeks, 0.25 mg/kg/6 weeks, 0.26 mg/kg/6 weeks, 0.27 mg/kg/6 weeks, 0.28 mg/kg/6 weeks, 0.29 mg/kg/6 weeks, 0.3 mg/kg/6 weeks, 0.31 mg/kg/6 weeks, 0.32 mg/kg/6 weeks, 0.33 mg/kg/6 weeks, 0.34 mg/kg/6 weeks, 0.35 mg/kg/6 weeks, 0.36 mg/kg/6 weeks, 0.37 mg/kg/6 weeks, 0.38 mg/kg/6 weeks, 0.39 mg/kg/6 weeks, 0.4 mg/kg/6 weeks, 0.41 mg/kg/6 weeks, 0.42 mg/kg/6 weeks, 0.43 mg/kg/6 weeks, 0.44 mg/kg/6 weeks, 0.45 mg/kg/6 weeks, 0.46 mg/kg/6 weeks, 0.47 mg/kg/6 weeks, 0.48 mg/kg/6 weeks, 0.49 mg/kg/6 weeks, 0.5 mg/kg/6 weeks, 0.51 mg/kg/6 weeks, 0.52 mg/kg/6 weeks, 0.53 mg/kg/6 weeks, 0.54 mg/kg/6 weeks, 0.55 mg/kg/6 weeks, 0.56 mg/kg/6 weeks, 0.57 mg/kg/6 weeks, 0.58 mg/kg/6 weeks, 0.59 mg/kg/6 weeks, 0.6 mg/kg/6 weeks, 0.61 mg/kg/6 weeks, 0.62 mg/kg/6 weeks, 0.63 mg/kg/6 weeks, 0.64 mg/kg/6 weeks, 0.65 mg/kg/6 weeks, 0.66 mg/kg/6 weeks, 0.67 mg/kg/6 weeks, 0.68 mg/kg/6 weeks, 0.69 mg/kg/6 weeks, 0.7 mg/kg/6 weeks, 0.71 mg/kg/6 weeks, 0.72 mg/kg/6 weeks, 0.73 mg/kg/6 weeks, 0.74 mg/kg/6 weeks, 0.75 mg/kg/6 weeks, 0.76 mg/kg/6 weeks, 0.77 mg/kg/6 weeks, 0.78 mg/kg/6 weeks, 0.79 mg/kg/6 weeks, 0.8 mg/kg/6 weeks, 0.81 mg/kg/6 weeks, 0.82 mg/kg/6 weeks, 0.83 mg/kg/6 weeks, 0.84 mg/kg/6 weeks, 0.85 mg/kg/6 weeks, 0.86 mg/kg/6 weeks, 0.87 mg/kg/6 weeks, 0.88 mg/kg/6 weeks, 0.89 mg/kg/6 weeks, 0.9 mg/kg/6 weeks, 0.91 mg/kg/6 weeks, 0.92 mg/kg/6 weeks, 0.93 mg/kg/6 weeks, 0.94 mg/kg/6 weeks, 0.95 mg/kg/6 weeks, 0.96 mg/kg/6 weeks, 0.97 mg/kg/6 weeks, 0.98 mg/kg/6 weeks, 0.99 mg/kg/6 weeks, 1 mg/kg/6 weeks, 1.01 mg/kg/6 weeks, 1.02 mg/kg/6 weeks, 1.03 mg/kg/6 weeks, 1.04 mg/kg/6 weeks, 1.05 mg/kg/6 weeks, 1.06 mg/kg/6 weeks, 1.07 mg/kg/6 weeks, 1.08 mg/kg/6 weeks, 1.09 mg/kg/6 weeks, 1.1 mg/kg/6 weeks, 1.11 mg/kg/6 weeks, 1.12 mg/kg/6 weeks, 1.13 mg/kg/6 weeks, 1.14 mg/kg/6 weeks, 1.15 mg/kg/6 weeks, 1.16 mg/kg/6 weeks, 1.17 mg/kg/6 weeks, 1.18 mg/kg/6 weeks, 1.19 mg/kg/6 weeks, 1.2 mg/kg/6 weeks, 1.21 mg/kg/6 weeks, 1.22 mg/kg/6 weeks, 1.23 mg/kg/6 weeks, 1.24 mg/kg/6 weeks, 1.25 mg/kg/6 weeks, 1.26 mg/kg/6 weeks, 1.27 mg/kg/6 weeks, 1.28 mg/kg/6 weeks, 1.29 mg/kg/6 weeks, 1.3 mg/kg/6 weeks, 1.31 mg/kg/6 weeks, 1.32 mg/kg/6 weeks, 1.33 mg/kg/6 weeks, 1.34 mg/kg/6 weeks, 1.35 mg/kg/6 weeks, 1.36 mg/kg/6 weeks, 1.37 mg/kg/6 weeks, 1.38 mg/kg/6 weeks, 1.39 mg/kg/6 weeks, 1.4 mg/kg/6 weeks, 1.41 mg/kg/6 weeks, 1.42 mg/kg/6 weeks, 1.43 mg/kg/6 weeks, 1.44 mg/kg/6 weeks, 1.45 mg/kg/6 weeks, 1.46 mg/kg/6 weeks, 1.47 mg/kg/6 weeks, 1.48 mg/kg/6 weeks, 1.49 mg/kg/6 weeks, 1.5 mg/kg/6 weeks, 1.51 mg/kg/6 weeks, 1.52 mg/kg/6 weeks, 1.53 mg/kg/6 weeks, 1.54 mg/kg/6 weeks, 1.55 mg/kg/6 weeks, 1.56 mg/kg/6 weeks, 1.57 mg/kg/6 weeks, 1.58 mg/kg/6 weeks, 1.59 mg/kg/6 weeks, 1.6 mg/kg/6 weeks, 1.61 mg/kg/6 weeks, 1.62 mg/kg/6 weeks, 1.63 mg/kg/6 weeks, 1.64 mg/kg/6 weeks, 1.65 mg/kg/6 weeks, 1.66 mg/kg/6 weeks, 1.67 mg/kg/6 weeks, 1.68 mg/kg/6 weeks, 1.69 mg/kg/6 weeks, 1.7 mg/kg/6 weeks, 1.71 mg/kg/6 weeks, 1.72 mg/kg/6 weeks, 1.73 mg/kg/6 weeks, 1.74 mg/kg/6 weeks, 1.75 mg/kg/6 weeks, 1.76 mg/kg/6 weeks, 1.77 mg/kg/6 weeks, 1.78 mg/kg/6 weeks, 1.79 mg/kg/6 weeks, 1.8 mg/kg/6 weeks, 1.81 mg/kg/6 weeks, 1.82 mg/kg/6 weeks, 1.83 mg/kg/6 weeks, 1.84 mg/kg/6 weeks, 1.85 mg/kg/6 weeks, 1.86 mg/kg/6 weeks, 1.87 mg/kg/6 weeks, 1.88 mg/kg/6 weeks, 1.89 mg/kg/6 weeks, 1.9 mg/kg/6 weeks, 1.91 mg/kg/6 weeks, 1.92 mg/kg/6 weeks, 1.93 mg/kg/6 weeks, 1.94 mg/kg/6 weeks, 1.95 mg/kg/6 weeks, 1.96 mg/kg/6 weeks, 1.97 mg/kg/6 weeks, 1.98 mg/kg/6 weeks, 1.99 mg/kg/6 weeks, 2 mg/kg/6 weeks, 2.01 mg/kg/6 weeks, 2.02 mg/kg/6 weeks, 2.03 mg/kg/6 weeks, 2.04 mg/kg/6 weeks, 2.05 mg/kg/6 weeks, 2.06 mg/kg/6 weeks, 2.07 mg/kg/6 weeks, 2.08 mg/kg/6 weeks, 2.09 mg/kg/6 weeks, 2.1 mg/kg/6 weeks, 2.11 mg/kg/6 weeks, 2.12 mg/kg/6 weeks, 2.13 mg/kg/6 weeks, 2.14 mg/kg/6 weeks, 2.15 mg/kg/6 weeks, 2.16 mg/kg/6 weeks, 2.17 mg/kg/6 weeks, 2.18 mg/kg/6 weeks, 2.19 mg/kg/6 weeks, 2.2 mg/kg/6 weeks, 2.21 mg/kg/6 weeks, 2.22 mg/kg/6 weeks, 2.23 mg/kg/6 weeks, 2.24 mg/kg/6 weeks, 2.25 mg/kg/6 weeks, 2.26 mg/kg/6 weeks, 2.27 mg/kg/6 weeks, 2.28 mg/kg/6 weeks, 2.29 mg/kg/6 weeks, 2.3 mg/kg/6 weeks, 2.31 mg/kg/6 weeks, 2.32 mg/kg/6 weeks, 2.33 mg/kg/6 weeks, 2.34 mg/kg/6 weeks, 2.35 mg/kg/6 weeks, 2.36 mg/kg/6 weeks, 2.37 mg/kg/6 weeks, 2.38 mg/kg/6 weeks, 2.39 mg/kg/6 weeks, 2.4 mg/kg/6 weeks, 2.41 mg/kg/6 weeks, 2.42 mg/kg/6 weeks, 2.43 mg/kg/6 weeks, 2.44 mg/kg/6 weeks, 2.45 mg/kg/6 weeks, 2.46 mg/kg/6 weeks, 2.47 mg/kg/6 weeks, 2.48 mg/kg/6 weeks, 2.49 mg/kg/6 weeks, 2.5 mg/kg/6 weeks, 2.51 mg/kg/6 weeks, 2.52 mg/kg/6 weeks, 2.53 mg/kg/6 weeks, 2.54 mg/kg/6 weeks, 2.55 mg/kg/6 weeks, 2.56 mg/kg/6 weeks, 2.57 mg/kg/6 weeks, 2.58 mg/kg/6 weeks, 2.59 mg/kg/6 weeks, 2.6 mg/kg/6 weeks, 2.61 mg/kg/6 weeks, 2.62 mg/kg/6 weeks, 2.63 mg/kg/6 weeks, 2.64 mg/kg/6 weeks, 2.65 mg/kg/6 weeks, 2.66 mg/kg/6 weeks, 2.67 mg/kg/6 weeks, 2.68 mg/kg/6 weeks, 2.69 mg/kg/6 weeks, 2.7 mg/kg/6 weeks, 2.71 mg/kg/6 weeks, 2.72 mg/kg/6 weeks, 2.73 mg/kg/6 weeks, 2.74 mg/kg/6 weeks, 2.75 mg/kg/6 weeks, 2.76 mg/kg/6 weeks, 2.77 mg/kg/6 weeks, 2.78 mg/kg/6 weeks, 2.79 mg/kg/6 weeks, 2.8 mg/kg/6 weeks, 2.81 mg/kg/6 weeks, 2.82 mg/kg/6 weeks, 2.83 mg/kg/6 weeks, 2.84 mg/kg/6 weeks, 2.85 mg/kg/6 weeks, 2.86 mg/kg/6 weeks, 2.87 mg/kg/6 weeks, 2.88 mg/kg/6 weeks, 2.89 mg/kg/6 weeks, 2.9 mg/kg/6 weeks, 2.91 mg/kg/6 weeks, 2.92 mg/kg/6 weeks, 2.93 mg/kg/6 weeks, 2.94 mg/kg/6 weeks, 2.95 mg/kg/6 weeks, 2.96 mg/kg/6 weeks, 2.97 mg/kg/6 weeks, 2.98 mg/kg/6 weeks, 2.99 mg/kg/6 weeks, or 3 mg/kg/6 weeks. Alternatively, in a non-limiting embodiment, the IL-31 antagonist of the present disclosure may be administered at, for example, 0.1 mg/kg/8 weeks, 0.11 mg/kg/8 weeks, 0.12 mg/kg/8 weeks, 0.125 mg/kg/8 weeks, 0.13 mg/kg/8 weeks, 0.14 mg/kg/8 weeks, 0.15 mg/kg/8 weeks, 0.16 mg/kg/8 weeks, 0.17 mg/kg/8 weeks, 0.18 mg/kg/8 weeks, 0.19 mg/kg/8 weeks, 0.2 mg/kg/8 weeks, 0.21 mg/kg/8 weeks, 0.22 mg/kg/8 weeks, 0.23 mg/kg/8 weeks, 0.24 mg/kg/8 weeks, 0.25 mg/kg/8 weeks, 0.26 mg/kg/8 weeks, 0.27 mg/kg/8 weeks, 0.28 mg/kg/8 weeks, 0.29 mg/kg/8 weeks, 0.3 mg/kg/8 weeks, 0.31 mg/kg/8 weeks, 0.32 mg/kg/8 weeks, 0.33 mg/kg/8 weeks, 0.34 mg/kg/8 weeks, 0.35 mg/kg/8 weeks, 0.36 mg/kg/8 weeks, 0.37 mg/kg/8 weeks, 0.38 mg/kg/8 weeks, 0.39 mg/kg/8 weeks, 0.4 mg/kg/8 weeks, 0.41 mg/kg/8 weeks, 0.42 mg/kg/8 weeks, 0.43 mg/kg/8 weeks, 0.44 mg/kg/8 weeks, 0.45 mg/kg/8 weeks, 0.46 mg/kg/8 weeks, 0.47 mg/kg/8 weeks, 0.48 mg/kg/8 weeks, 0.49 mg/kg/8 weeks, 0.5 mg/kg/8 weeks, 0.51 mg/kg/8 weeks, 0.52 mg/kg/8 weeks, 0.53 mg/kg/8 weeks, 0.54 mg/kg/8 weeks, 0.55 mg/kg/8 weeks, 0.56 mg/kg/8 weeks, 0.57 mg/kg/8 weeks, 0.58 mg/kg/8 weeks, 0.59 mg/kg/8 weeks, 0.6 mg/kg/8 weeks, 0.61 mg/kg/8 weeks, 0.62 mg/kg/8 weeks, 0.63 mg/kg/8 weeks, 0.64 mg/kg/8 weeks, 0.65 mg/kg/8 weeks, 0.66 mg/kg/8 weeks, 0.67 mg/kg/8 weeks, 0.68 mg/kg/8 weeks, 0.69 mg/kg/8 weeks, 0.7 mg/kg/8 weeks, 0.71 mg/kg/8 weeks, 0.72 mg/kg/8 weeks, 0.73 mg/kg/8 weeks, 0.74 mg/kg/8 weeks, 0.75 mg/kg/8 weeks, 0.76 mg/kg/8 weeks, 0.77 mg/kg/8 weeks, 0.78 mg/kg/8 weeks, 0.79 mg/kg/8 weeks, 0.8 mg/kg/8 weeks, 0.81 mg/kg/8 weeks, 0.82 mg/kg/8 weeks, 0.83 mg/kg/8 weeks, 0.84 mg/kg/8 weeks, 0.85 mg/kg/8 weeks, 0.86 mg/kg/8 weeks, 0.87 mg/kg/8 weeks, 0.88 mg/kg/8 weeks, 0.89 mg/kg/8 weeks, 0.9 mg/kg/8 weeks, 0.91 mg/kg/8 weeks, 0.92 mg/kg/8 weeks, 0.93 mg/kg/8 weeks, 0.94 mg/kg/8 weeks, 0.95 mg/kg/8 weeks, 0.96 mg/kg/8 weeks, 0.97 mg/kg/8 weeks, 0.98 mg/kg/8 weeks, 0.99 mg/kg/8 weeks, 1 mg/kg/8 weeks, 1.01 mg/kg/8 weeks, 1.02 mg/kg/8 weeks, 1.03 mg/kg/8 weeks, 1.04 mg/kg/8 weeks, 1.05 mg/kg/8 weeks, 1.06 mg/kg/8 weeks, 1.07 mg/kg/8 weeks, 1.08 mg/kg/8 weeks, 1.09 mg/kg/8 weeks, 1.1 mg/kg/8 weeks, 1.11 mg/kg/8 weeks, 1.12 mg/kg/8 weeks, 1.13 mg/kg/8 weeks, 1.14 mg/kg/8 weeks, 1.15 mg/kg/8 weeks, 1.16 mg/kg/8 weeks, 1.17 mg/kg/8 weeks, 1.18 mg/kg/8 weeks, 1.19 mg/kg/8 weeks, 1.2 mg/kg/8 weeks, 1.21 mg/kg/8 weeks, 1.22 mg/kg/8 weeks, 1.23 mg/kg/8 weeks, 1.24 mg/kg/8 weeks, 1.25 mg/kg/8 weeks, 1.26 mg/kg/8 weeks, 1.27 mg/kg/8 weeks, 1.28 mg/kg/8 weeks, 1.29 mg/kg/8 weeks, 1.3 mg/kg/8 weeks, 1.31 mg/kg/8 weeks, 1.32 mg/kg/8 weeks, 1.33 mg/kg/8 weeks, 1.34 mg/kg/8 weeks, 1.35 mg/kg/8 weeks, 1.36 mg/kg/8 weeks, 1.37 mg/kg/8 weeks, 1.38 mg/kg/8 weeks, 1.39 mg/kg/8 weeks, 1.4 mg/kg/8 weeks, 1.41 mg/kg/8 weeks, 1.42 mg/kg/8 weeks, 1.43 mg/kg/8 weeks, 1.44 mg/kg/8 weeks, 1.45 mg/kg/8 weeks, 1.46 mg/kg/8 weeks, 1.47 mg/kg/8 weeks, 1.48 mg/kg/8 weeks, 1.49 mg/kg/8 weeks, 1.5 mg/kg/8 weeks, 1.51 mg/kg/8 weeks, 1.52 mg/kg/8 weeks, 1.53 mg/kg/8 weeks, 1.54 mg/kg/8 weeks, 1.55 mg/kg/8 weeks, 1.56 mg/kg/8 weeks, 1.57 mg/kg/8 weeks, 1.58 mg/kg/8 weeks, 1.59 mg/kg/8 weeks, 1.6 mg/kg/8 weeks, 1.61 mg/kg/8 weeks, 1.62 mg/kg/8 weeks, 1.63 mg/kg/8 weeks, 1.64 mg/kg/8 weeks, 1.65 mg/kg/8 weeks, 1.66 mg/kg/8 weeks, 1.67 mg/kg/8 weeks, 1.68 mg/kg/8 weeks, 1.69 mg/kg/8 weeks, 1.7 mg/kg/8 weeks, 1.71 mg/kg/8 weeks, 1.72 mg/kg/8 weeks, 1.73 mg/kg/8 weeks, 1.74 mg/kg/8 weeks, 1.75 mg/kg/8 weeks, 1.76 mg/kg/8 weeks, 1.77 mg/kg/8 weeks, 1.78 mg/kg/8 weeks, 1.79 mg/kg/8 weeks, 1.8 mg/kg/8 weeks, 1.81 mg/kg/8 weeks, 1.82 mg/kg/8 weeks, 1.83 mg/kg/8 weeks, 1.84 mg/kg/8 weeks, 1.85 mg/kg/8 weeks, 1.86 mg/kg/8 weeks, 1.87 mg/kg/8 weeks, 1.88 mg/kg/8 weeks, 1.89 mg/kg/8 weeks, 1.9 mg/kg/8 weeks, 1.91 mg/kg/8 weeks, 1.92 mg/kg/8 weeks, 1.93 mg/kg/8 weeks, 1.94 mg/kg/8 weeks, 1.95 mg/kg/8 weeks, 1.96 mg/kg/8 weeks, 1.97 mg/kg/8 weeks, 1.98 mg/kg/8 weeks, 1.99 mg/kg/8 weeks, 2 mg/kg/8 weeks, 2.01 mg/kg/8 weeks, 2.02 mg/kg/8 weeks, 2.03 mg/kg/8 weeks, 2.04 mg/kg/8 weeks, 2.05 mg/kg/8 weeks, 2.06 mg/kg/8 weeks, 2.07 mg/kg/8 weeks, 2.08 mg/kg/8 weeks, 2.09 mg/kg/8 weeks, 2.1 mg/kg/8 weeks, 2.11 mg/kg/8 weeks, 2.12 mg/kg/8 weeks, 2.13 mg/kg/8 weeks, 2.14 mg/kg/8 weeks, 2.15 mg/kg/8 weeks, 2.16 mg/kg/8 weeks, 2.17 mg/kg/8 weeks, 2.18 mg/kg/8 weeks, 2.19 mg/kg/8 weeks, 2.2 mg/kg/8 weeks, 2.21 mg/kg/8 weeks, 2.22 mg/kg/8 weeks, 2.23 mg/kg/8 weeks, 2.24 mg/kg/8 weeks, 2.25 mg/kg/8 weeks, 2.26 mg/kg/8 weeks, 2.27 mg/kg/8 weeks, 2.28 mg/kg/8 weeks, 2.29 mg/kg/8 weeks, 2.3 mg/kg/8 weeks, 2.31 mg/kg/8 weeks, 2.32 mg/kg/8 weeks, 2.33 mg/kg/8 weeks, 2.34 mg/kg/8 weeks, 2.35 mg/kg/8 weeks, 2.36 mg/kg/8 weeks, 2.37 mg/kg/8 weeks, 2.38 mg/kg/8 weeks, 2.39 mg/kg/8 weeks, 2.4 mg/kg/8 weeks, 2.41 mg/kg/8 weeks, 2.42 mg/kg/8 weeks, 2.43 mg/kg/8 weeks, 2.44 mg/kg/8 weeks, 2.45 mg/kg/8 weeks, 2.46 mg/kg/8 weeks, 2.47 mg/kg/8 weeks, 2.48 mg/kg/8 weeks, 2.49 mg/kg/8 weeks, 2.5 mg/kg/8 weeks, 2.51 mg/kg/8 weeks, 2.52 mg/kg/8 weeks, 2.53 mg/kg/8 weeks, 2.54 mg/kg/8 weeks, 2.55 mg/kg/8 weeks, 2.56 mg/kg/8 weeks, 2.57 mg/kg/8 weeks, 2.58 mg/kg/8 weeks, 2.59 mg/kg/8 weeks, 2.6 mg/kg/8 weeks, 2.61 mg/kg/8 weeks, 2.62 mg/kg/8 weeks, 2.63 mg/kg/8 weeks, 2.64 mg/kg/8 weeks, 2.65 mg/kg/8 weeks, 2.66 mg/kg/8 weeks, 2.67 mg/kg/8 weeks, 2.68 mg/kg/8 weeks, 2.69 mg/kg/8 weeks, 2.7 mg/kg/8 weeks, 2.71 mg/kg/8 weeks, 2.72 mg/kg/8 weeks, 2.73 mg/kg/8 weeks, 2.74 mg/kg/8 weeks, 2.75 mg/kg/8 weeks, 2.76 mg/kg/8 weeks, 2.77 mg/kg/8 weeks, 2.78 mg/kg/8 weeks, 2.79 mg/kg/8 weeks, 2.8 mg/kg/8 weeks, 2.81 mg/kg/8 weeks, 2.82 mg/kg/8 weeks, 2.83 mg/kg/8 weeks, 2.84 mg/kg/8 weeks, 2.85 mg/kg/8 weeks, 2.86 mg/kg/8 weeks, 2.87 mg/kg/8 weeks, 2.88 mg/kg/8 weeks, 2.89 mg/kg/8 weeks, 2.9 mg/kg/8 weeks, 2.91 mg/kg/8 weeks, 2.92 mg/kg/8 weeks, 2.93 mg/kg/8 weeks, 2.94 mg/kg/8 weeks, 2.95 mg/kg/8 weeks, 2.96 mg/kg/8 weeks, 2.97 mg/kg/8 weeks, 2.98 mg/kg/8 weeks, 2.99 mg/kg/8 weeks, or 3 mg/kg/8 weeks. Alternatively, in a non-limiting embodiment, the IL-31 antagonist of the present disclosure may be administered at, for example, 0.1 mg/kg/10 weeks, 0.11 mg/kg/10 weeks, 0.12 mg/kg/10 weeks, 0.125 mg/kg/10 weeks, 0.13 mg/kg/10 weeks, 0.14 mg/kg/10 weeks, 0.15 mg/kg/10 weeks, 0.16 mg/kg/10 weeks, 0.17 mg/kg/10 weeks, 0.18 mg/kg/10 weeks, 0.19 mg/kg/10 weeks, 0.2 mg/kg/10 weeks, 0.21 mg/kg/10 weeks, 0.22 mg/kg/10 weeks, 0.23 mg/kg/10 weeks, 0.24 mg/kg/10 weeks, 0.25 mg/kg/10 weeks, 0.26 mg/kg/10 weeks, 0.27 mg/kg/10 weeks, 0.28 mg/kg/10 weeks, 0.29 mg/kg/10 weeks, 0.3 mg/kg/10 weeks, 0.31 mg/kg/10 weeks, 0.32 mg/kg/10 weeks, 0.33 mg/kg/10 weeks, 0.34 mg/kg/10 weeks, 0.35 mg/kg/10 weeks, 0.36 mg/kg/10 weeks, 0.37 mg/kg/10 weeks, 0.38 mg/kg/10 weeks, 0.39 mg/kg/10 weeks, 0.4 mg/kg/10 weeks, 0.41 mg/kg/10 weeks, 0.42 mg/kg/10 weeks, 0.43 mg/kg/10 weeks, 0.44 mg/kg/10 weeks, 0.45 mg/kg/10 weeks, 0.46 mg/kg/10 weeks, 0.47 mg/kg/10 weeks, 0.48 mg/kg/10 weeks, 0.49 mg/kg/10 weeks, 0.5 mg/kg/10 weeks, 0.51 mg/kg/10 weeks, 0.52 mg/kg/10 weeks, 0.53 mg/kg/10 weeks, 0.54 mg/kg/10 weeks, 0.55 mg/kg/10 weeks, 0.56 mg/kg/10 weeks, 0.57 mg/kg/10 weeks, 0.58 mg/kg/10 weeks, 0.59 mg/kg/10 weeks, 0.6 mg/kg/10 weeks, 0.61 mg/kg/10 weeks, 0.62 mg/kg/10 weeks, 0.63 mg/kg/10 weeks, 0.64 mg/kg/10 weeks, 0.65 mg/kg/10 weeks, 0.66 mg/kg/10 weeks, 0.67 mg/kg/10 weeks, 0.68 mg/kg/10 weeks, 0.69 mg/kg/10 weeks, 0.7 mg/kg/10 weeks, 0.71 mg/kg/10 weeks, 0.72 mg/kg/10 weeks, 0.73 mg/kg/10 weeks, 0.74 mg/kg/10 weeks, 0.75 mg/kg/10 weeks, 0.76 mg/kg/10 weeks, 0.77 mg/kg/10 weeks, 0.78 mg/kg/10 weeks, 0.79 mg/kg/10 weeks, 0.8 mg/kg/10 weeks, 0.81 mg/kg/10 weeks, 0.82 mg/kg/10 weeks, 0.83 mg/kg/10 weeks, 0.84 mg/kg/10 weeks, 0.85 mg/kg/10 weeks, 0.86 mg/kg/10 weeks, 0.87 mg/kg/10 weeks, 0.88 mg/kg/10 weeks, 0.89 mg/kg/10 weeks, 0.9 mg/kg/10 weeks, 0.91 mg/kg/10 weeks, 0.92 mg/kg/10 weeks, 0.93 mg/kg/10 weeks, 0.94 mg/kg/10 weeks, 0.95 mg/kg/10 weeks, 0.96 mg/kg/10 weeks, 0.97 mg/kg/10 weeks, 0.98 mg/kg/10 weeks, 0.99 mg/kg/10 weeks, 1 mg/kg/10 weeks, 1.01 mg/kg/10 weeks, 1.02 mg/kg/10 weeks, 1.03 mg/kg/10 weeks, 1.04 mg/kg/10 weeks, 1.05 mg/kg/10 weeks, 1.06 mg/kg/10 weeks, 1.07 mg/kg/10 weeks, 1.08 mg/kg/10 weeks, 1.09 mg/kg/10 weeks, 1.1 mg/kg/10 weeks, 1.11 mg/kg/10 weeks, 1.12 mg/kg/10 weeks, 1.13 mg/kg/10 weeks, 1.14 mg/kg/10 weeks, 1.15 mg/kg/10 weeks, 1.16 mg/kg/10 weeks, 1.17 mg/kg/10 weeks, 1.18 mg/kg/10 weeks, 1.19 mg/kg/10 weeks, 1.2 mg/kg/10 weeks, 1.21 mg/kg/10 weeks, 1.22 mg/kg/10 weeks, 1.23 mg/kg/10 weeks, 1.24 mg/kg/10 weeks, 1.25 mg/kg/10 weeks, 1.26 mg/kg/10 weeks, 1.27 mg/kg/10 weeks, 1.28 mg/kg/10 weeks, 1.29 mg/kg/10 weeks, 1.3 mg/kg/10 weeks, 1.31 mg/kg/10 weeks, 1.32 mg/kg/10 weeks, 1.33 mg/kg/10 weeks, 1.34 mg/kg/10 weeks, 1.35 mg/kg/10 weeks, 1.36 mg/kg/10 weeks, 1.37 mg/kg/10 weeks, 1.38 mg/kg/10 weeks, 1.39 mg/kg/10 weeks, 1.4 mg/kg/10 weeks, 1.41 mg/kg/10 weeks, 1.42 mg/kg/10 weeks, 1.43 mg/kg/10 weeks, 1.44 mg/kg/10 weeks, 1.45 mg/kg/10 weeks, 1.46 mg/kg/10 weeks, 1.47 mg/kg/10 weeks, 1.48 mg/kg/10 weeks, 1.49 mg/kg/10 weeks, 1.5 mg/kg/10 weeks, 1.51 mg/kg/10 weeks, 1.52 mg/kg/10 weeks, 1.53 mg/kg/10 weeks, 1.54 mg/kg/10 weeks, 1.55 mg/kg/10 weeks, 1.56 mg/kg/10 weeks, 1.57 mg/kg/10 weeks, 1.58 mg/kg/10 weeks, 1.59 mg/kg/10 weeks, 1.6 mg/kg/10 weeks, 1.61 mg/kg/10 weeks, 1.62 mg/kg/10 weeks, 1.63 mg/kg/10 weeks, 1.64 mg/kg/10 weeks, 1.65 mg/kg/10 weeks, 1.66 mg/kg/10 weeks, 1.67 mg/kg/10 weeks, 1.68 mg/kg/10 weeks, 1.69 mg/kg/10 weeks, 1.7 mg/kg/10 weeks, 1.71 mg/kg/10 weeks, 1.72 mg/kg/10 weeks, 1.73 mg/kg/10 weeks, 1.74 mg/kg/10 weeks, 1.75 mg/kg/10 weeks, 1.76 mg/kg/10 weeks, 1.77 mg/kg/10 weeks, 1.78 mg/kg/10 weeks, 1.79 mg/kg/10 weeks, 1.8 mg/kg/10 weeks, 1.81 mg/kg/10 weeks, 1.82 mg/kg/10 weeks, 1.83 mg/kg/10 weeks, 1.84 mg/kg/10 weeks, 1.85 mg/kg/10 weeks, 1.86 mg/kg/10 weeks, 1.87 mg/kg/10 weeks, 1.88 mg/kg/10 weeks, 1.89 mg/kg/10 weeks, 1.9 mg/kg/10 weeks, 1.91 mg/kg/10 weeks, 1.92 mg/kg/10 weeks, 1.93 mg/kg/10 weeks, 1.94 mg/kg/10 weeks, 1.95 mg/kg/10 weeks, 1.96 mg/kg/10 weeks, 1.97 mg/kg/10 weeks, 1.98 mg/kg/10 weeks, 1.99 mg/kg/10 weeks, 2 mg/kg/10 weeks, 2.01 mg/kg/10 weeks, 2.02 mg/kg/10 weeks, 2.03 mg/kg/10 weeks, 2.04 mg/kg/10 weeks, 2.05 mg/kg/10 weeks, 2.06 mg/kg/10 weeks, 2.07 mg/kg/10 weeks, 2.08 mg/kg/10 weeks, 2.09 mg/kg/10 weeks, 2.1 mg/kg/10 weeks, 2.11 mg/kg/10 weeks, 2.12 mg/kg/10 weeks, 2.13 mg/kg/10 weeks, 2.14 mg/kg/10 weeks, 2.15 mg/kg/10 weeks, 2.16 mg/kg/10 weeks, 2.17 mg/kg/10 weeks, 2.18 mg/kg/10 weeks, 2.19 mg/kg/10 weeks, 2.2 mg/kg/10 weeks, 2.21 mg/kg/10 weeks, 2.22 mg/kg/10 weeks, 2.23 mg/kg/10 weeks, 2.24 mg/kg/10 weeks, 2.25 mg/kg/10 weeks, 2.26 mg/kg/10 weeks, 2.27 mg/kg/10 weeks, 2.28 mg/kg/10 weeks, 2.29 mg/kg/10 weeks, 2.3 mg/kg/10 weeks, 2.31 mg/kg/10 weeks, 2.32 mg/kg/10 weeks, 2.33 mg/kg/10 weeks, 2.34 mg/kg/10 weeks, 2.35 mg/kg/10 weeks, 2.36 mg/kg/10 weeks, 2.37 mg/kg/10 weeks, 2.38 mg/kg/10 weeks, 2.39 mg/kg/10 weeks, 2.4 mg/kg/10 weeks, 2.41 mg/kg/10 weeks, 2.42 mg/kg/10 weeks, 2.43 mg/kg/10 weeks, 2.44 mg/kg/10 weeks, 2.45 mg/kg/10 weeks, 2.46 mg/kg/10 weeks, 2.47 mg/kg/10 weeks, 2.48 mg/kg/10 weeks, 2.49 mg/kg/10 weeks, 2.5 mg/kg/10 weeks, 2.51 mg/kg/10 weeks, 2.52 mg/kg/10 weeks, 2.53 mg/kg/10 weeks, 2.54 mg/kg/10 weeks, 2.55 mg/kg/10 weeks, 2.56 mg/kg/10 weeks, 2.57 mg/kg/10 weeks, 2.58 mg/kg/10 weeks, 2.59 mg/kg/10 weeks, 2.6 mg/kg/10 weeks, 2.61 mg/kg/10 weeks, 2.62 mg/kg/10 weeks, 2.63 mg/kg/10 weeks, 2.64 mg/kg/10 weeks, 2.65 mg/kg/10 weeks, 2.66 mg/kg/10 weeks, 2.67 mg/kg/10 weeks, 2.68 mg/kg/10 weeks, 2.69 mg/kg/10 weeks, 2.7 mg/kg/10 weeks, 2.71 mg/kg/10 weeks, 2.72 mg/kg/10 weeks, 2.73 mg/kg/10 weeks, 2.74 mg/kg/10 weeks, 2.75 mg/kg/10 weeks, 2.76 mg/kg/10 weeks, 2.77 mg/kg/10 weeks, 2.78 mg/kg/10 weeks, 2.79 mg/kg/10 weeks, 2.8 mg/kg/10 weeks, 2.81 mg/kg/10 weeks, 2.82 mg/kg/10 weeks, 2.83 mg/kg/10 weeks, 2.84 mg/kg/10 weeks, 2.85 mg/kg/10 weeks, 2.86 mg/kg/10 weeks, 2.87 mg/kg/10 weeks, 2.88 mg/kg/10 weeks, 2.89 mg/kg/10 weeks, 2.9 mg/kg/10 weeks, 2.91 mg/kg/10 weeks, 2.92 mg/kg/10 weeks, 2.93 mg/kg/10 weeks, 2.94 mg/kg/10 weeks, 2.95 mg/kg/10 weeks, 2.96 mg/kg/10 weeks, 2.97 mg/kg/10 weeks, 2.98 mg/kg/10 weeks, 2.99 mg/kg/10 weeks, or 3 mg/kg/10 weeks. Alternatively, in a non-limiting embodiment, the IL-31 antagonist of the present disclosure may be administered at, for example, 0.1 mg/kg/12 weeks, 0.11 mg/kg/12 weeks, 0.12 mg/kg/12 weeks, 0.125 mg/kg/12 weeks, 0.13 mg/kg/12 weeks, 0.14 mg/kg/12 weeks, 0.15 mg/kg/12 weeks, 0.16 mg/kg/12 weeks, 0.17 mg/kg/12 weeks, 0.18 mg/kg/12 weeks, 0.19 mg/kg/12 weeks, 0.2 mg/kg/12 weeks, 0.21 mg/kg/12 weeks, 0.22 mg/kg/12 weeks, 0.23 mg/kg/12 weeks, 0.24 mg/kg/12 weeks, 0.25 mg/kg/12 weeks, 0.26 mg/kg/12 weeks, 0.27 mg/kg/12 weeks, 0.28 mg/kg/12 weeks, 0.29 mg/kg/12 weeks, 0.3 mg/kg/12 weeks, 0.31 mg/kg/12 weeks, 0.32 mg/kg/12 weeks, 0.33 mg/kg/12 weeks, 0.34 mg/kg/12 weeks, 0.35 mg/kg/12 weeks, 0.36 mg/kg/12 weeks, 0.37 mg/kg/12 weeks, 0.38 mg/kg/12 weeks, 0.39 mg/kg/12 weeks, 0.4 mg/kg/12 weeks, 0.41 mg/kg/12 weeks, 0.42 mg/kg/12 weeks, 0.43 mg/kg/12 weeks, 0.44 mg/kg/12 weeks, 0.45 mg/kg/12 weeks, 0.46 mg/kg/12 weeks, 0.47 mg/kg/12 weeks, 0.48 mg/kg/12 weeks, 0.49 mg/kg/12 weeks, 0.5 mg/kg/12 weeks, 0.51 mg/kg/12 weeks, 0.52 mg/kg/12 weeks, 0.53 mg/kg/12 weeks, 0.54 mg/kg/12 weeks, 0.55 mg/kg/12 weeks, 0.56 mg/kg/12 weeks, 0.57 mg/kg/12 weeks, 0.58 mg/kg/12 weeks, 0.59 mg/kg/12 weeks, 0.6 mg/kg/12 weeks, 0.61 mg/kg/12 weeks, 0.62 mg/kg/12 weeks, 0.63 mg/kg/12 weeks, 0.64 mg/kg/12 weeks, 0.65 mg/kg/12 weeks, 0.66 mg/kg/12 weeks, 0.67 mg/kg/12 weeks, 0.68 mg/kg/12 weeks, 0.69 mg/kg/12 weeks, 0.7 mg/kg/12 weeks, 0.71 mg/kg/12 weeks, 0.72 mg/kg/12 weeks, 0.73 mg/kg/12 weeks, 0.74 mg/kg/12 weeks, 0.75 mg/kg/12 weeks, 0.76 mg/kg/12 weeks, 0.77 mg/kg/12 weeks, 0.78 mg/kg/12 weeks, 0.79 mg/kg/12 weeks, 0.8 mg/kg/12 weeks, 0.81 mg/kg/12 weeks, 0.82 mg/kg/12 weeks, 0.83 mg/kg/12 weeks, 0.84 mg/kg/12 weeks, 0.85 mg/kg/12 weeks, 0.86 mg/kg/12 weeks, 0.87 mg/kg/12 weeks, 0.88 mg/kg/12 weeks, 0.89 mg/kg/12 weeks, 0.9 mg/kg/12 weeks, 0.91 mg/kg/12 weeks, 0.92 mg/kg/12 weeks, 0.93 mg/kg/12 weeks, 0.94 mg/kg/12 weeks, 0.95 mg/kg/12 weeks, 0.96 mg/kg/12 weeks, 0.97 mg/kg/12 weeks, 0.98 mg/kg/12 weeks, 0.99 mg/kg/12 weeks, 1 mg/kg/12 weeks, 1.01 mg/kg/12 weeks, 1.02 mg/kg/12 weeks, 1.03 mg/kg/12 weeks, 1.04 mg/kg/12 weeks, 1.05 mg/kg/12 weeks, 1.06 mg/kg/12 weeks, 1.07 mg/kg/12 weeks, 1.08 mg/kg/12 weeks, 1.09 mg/kg/12 weeks, 1.1 mg/kg/12 weeks, 1.11 mg/kg/12 weeks, 1.12 mg/kg/12 weeks, 1.13 mg/kg/12 weeks, 1.14 mg/kg/12 weeks, 1.15 mg/kg/12 weeks, 1.16 mg/kg/12 weeks, 1.17 mg/kg/12 weeks, 1.18 mg/kg/12 weeks, 1.19 mg/kg/12 weeks, 1.2 mg/kg/12 weeks, 1.21 mg/kg/12 weeks, 1.22 mg/kg/12 weeks, 1.23 mg/kg/12 weeks, 1.24 mg/kg/12 weeks, 1.25 mg/kg/12 weeks, 1.26 mg/kg/12 weeks, 1.27 mg/kg/12 weeks, 1.28 mg/kg/12 weeks, 1.29 mg/kg/12 weeks, 1.3 mg/kg/12 weeks, 1.31 mg/kg/12 weeks, 1.32 mg/kg/12 weeks, 1.33 mg/kg/12 weeks, 1.34 mg/kg/12 weeks, 1.35 mg/kg/12 weeks, 1.36 mg/kg/12 weeks, 1.37 mg/kg/12 weeks, 1.38 mg/kg/12 weeks, 1.39 mg/kg/12 weeks, 1.4 mg/kg/12 weeks, 1.41 mg/kg/12 weeks, 1.42 mg/kg/12 weeks, 1.43 mg/kg/12 weeks, 1.44 mg/kg/12 weeks, 1.45 mg/kg/12 weeks, 1.46 mg/kg/12 weeks, 1.47 mg/kg/12 weeks, 1.48 mg/kg/12 weeks, 1.49 mg/kg/12 weeks, 1.5 mg/kg/12 weeks, 1.51 mg/kg/12 weeks, 1.52 mg/kg/12 weeks, 1.53 mg/kg/12 weeks, 1.54 mg/kg/12 weeks, 1.55 mg/kg/12 weeks, 1.56 mg/kg/12 weeks, 1.57 mg/kg/12 weeks, 1.58 mg/kg/12 weeks, 1.59 mg/kg/12 weeks, 1.6 mg/kg/12 weeks, 1.61 mg/kg/12 weeks, 1.62 mg/kg/12 weeks, 1.63 mg/kg/12 weeks, 1.64 mg/kg/12 weeks, 1.65 mg/kg/12 weeks, 1.66 mg/kg/12 weeks, 1.67 mg/kg/12 weeks, 1.68 mg/kg/12 weeks, 1.69 mg/kg/12 weeks, 1.7 mg/kg/12 weeks, 1.71 mg/kg/12 weeks, 1.72 mg/kg/12 weeks, 1.73 mg/kg/12 weeks, 1.74 mg/kg/12 weeks, 1.75 mg/kg/12 weeks, 1.76 mg/kg/12 weeks, 1.77 mg/kg/12 weeks, 1.78 mg/kg/12 weeks, 1.79 mg/kg/12 weeks, 1.8 mg/kg/12 weeks, 1.81 mg/kg/12 weeks, 1.82 mg/kg/12 weeks, 1.83 mg/kg/12 weeks, 1.84 mg/kg/12 weeks, 1.85 mg/kg/12 weeks, 1.86 mg/kg/12 weeks, 1.87 mg/kg/12 weeks, 1.88 mg/kg/12 weeks, 1.89 mg/kg/12 weeks, 1.9 mg/kg/12 weeks, 1.91 mg/kg/12 weeks, 1.92 mg/kg/12 weeks, 1.93 mg/kg/12 weeks, 1.94 mg/kg/12 weeks, 1.95 mg/kg/12 weeks, 1.96 mg/kg/12 weeks, 1.97 mg/kg/12 weeks, 1.98 mg/kg/12 weeks, 1.99 mg/kg/12 weeks, 2 mg/kg/12 weeks, 2.01 mg/kg/12 weeks, 2.02 mg/kg/12 weeks, 2.03 mg/kg/12 weeks, 2.04 mg/kg/12 weeks, 2.05 mg/kg/12 weeks, 2.06 mg/kg/12 weeks, 2.07 mg/kg/12 weeks, 2.08 mg/kg/12 weeks, 2.09 mg/kg/12 weeks, 2.1 mg/kg/12 weeks, 2.11 mg/kg/12 weeks, 2.12 mg/kg/12 weeks, 2.13 mg/kg/12 weeks, 2.14 mg/kg/12 weeks, 2.15 mg/kg/12 weeks, 2.16 mg/kg/12 weeks, 2.17 mg/kg/12 weeks, 2.18 mg/kg/12 weeks, 2.19 mg/kg/12 weeks, 2.2 mg/kg/12 weeks, 2.21 mg/kg/12 weeks, 2.22 mg/kg/12 weeks, 2.23 mg/kg/12 weeks, 2.24 mg/kg/12 weeks, 2.25 mg/kg/12 weeks, 2.26 mg/kg/12 weeks, 2.27 mg/kg/12 weeks, 2.28 mg/kg/12 weeks, 2.29 mg/kg/12 weeks, 2.3 mg/kg/12 weeks, 2.31 mg/kg/12 weeks, 2.32 mg/kg/12 weeks, 2.33 mg/kg/12 weeks, 2.34 mg/kg/12 weeks, 2.35 mg/kg/12 weeks, 2.36 mg/kg/12 weeks, 2.37 mg/kg/12 weeks, 2.38 mg/kg/12 weeks, 2.39 mg/kg/12 weeks, 2.4 mg/kg/12 weeks, 2.41 mg/kg/12 weeks, 2.42 mg/kg/12 weeks, 2.43 mg/kg/12 weeks, 2.44 mg/kg/12 weeks, 2.45 mg/kg/12 weeks, 2.46 mg/kg/12 weeks, 2.47 mg/kg/12 weeks, 2.48 mg/kg/12 weeks, 2.49 mg/kg/12 weeks, 2.5 mg/kg/12 weeks, 2.51 mg/kg/12 weeks, 2.52 mg/kg/12 weeks, 2.53 mg/kg/12 weeks, 2.54 mg/kg/12 weeks, 2.55 mg/kg/12 weeks, 2.56 mg/kg/12 weeks, 2.57 mg/kg/12 weeks, 2.58 mg/kg/12 weeks, 2.59 mg/kg/12 weeks, 2.6 mg/kg/12 weeks, 2.61 mg/kg/12 weeks, 2.62 mg/kg/12 weeks, 2.63 mg/kg/12 weeks, 2.64 mg/kg/12 weeks, 2.65 mg/kg/12 weeks, 2.66 mg/kg/12 weeks, 2.67 mg/kg/12 weeks, 2.68 mg/kg/12 weeks, 2.69 mg/kg/12 weeks, 2.7 mg/kg/12 weeks, 2.71 mg/kg/12 weeks, 2.72 mg/kg/12 weeks, 2.73 mg/kg/12 weeks, 2.74 mg/kg/12 weeks, 2.75 mg/kg/12 weeks, 2.76 mg/kg/12 weeks, 2.77 mg/kg/12 weeks, 2.78 mg/kg/12 weeks, 2.79 mg/kg/12 weeks, 2.8 mg/kg/12 weeks, 2.81 mg/kg/12 weeks, 2.82 mg/kg/12 weeks, 2.83 mg/kg/12 weeks, 2.84 mg/kg/12 weeks, 2.85 mg/kg/12 weeks, 2.86 mg/kg/12 weeks, 2.87 mg/kg/12 weeks, 2.88 mg/kg/12 weeks, 2.89 mg/kg/12 weeks, 2.9 mg/kg/12 weeks, 2.91 mg/kg/12 weeks, 2.92 mg/kg/12 weeks, 2.93 mg/kg/12 weeks, 2.94 mg/kg/12 weeks, 2.95 mg/kg/12 weeks, 2.96 mg/kg/12 weeks, 2.97 mg/kg/12 weeks, 2.98 mg/kg/12 weeks, 2.99 mg/kg/12 weeks, or 3 mg/kg/12 weeks.

When the IL-31 antagonist of the present disclosure is repeatedly administered in equal amounts at the same dosing interval to a subject with or potentially with atopic dermatitis, using the above-described predetermined dosing interval and predetermined dose (dosage), it can persistently suppress or improve atopic dermatitis and/or one or more of various symptoms caused by atopic dermatitis (e.g., pruritus, redness, induration, papules, edema, excoriations, lichenification, decrease in QOL, and lack of sleep). The dosage to be administered in equal amounts and the same dosing interval are determined, for example, in view of effect and safety.

In one embodiment, oral or parenteral administration can be selected as the method of administering the pharmaceutical composition of present disclosure to a subject. Typically, when the active ingredient is a low-molecular-weight compound, oral or parenteral administration may be selected, and when the active ingredient is a high-molecular-weight compound, parenteral administration is preferred, but not limited thereto. Examples of parenteral administration include injection, nasal, pulmonary, and percutaneous administration. Additionally, examples of injections include intravenous, intramuscular, intraperitoneal, and subcutaneous injections. Using these methods of administration, the pharmaceutical composition of present disclosure can be systemically or topically administered. For example, subcutaneous administration by subcutaneous injection is preferred.

In one embodiment, the pharmaceutical composition of the present disclosure can be prepared by combining the IL-31 antagonist as an active ingredient with pharmaceutically acceptable carriers, using a known method. For example, the IL-31 antagonist may be combined, as appropriate, with pharmaceutically acceptable carriers or media such as sterilized water or saline solution, vegetable oils, emulsifiers, suspensions, surfactants, stabilizers, flavoring agents, excipients, vehicles, preservatives, and binders, for example, and formulated into a pharmaceutical preparation. Examples of carriers include light anhydrous silicic acid, lactose, crystalline cellulose, mannitol, starch, carmellose calcium, carmellose sodium, hydroxypropylcellulose, hydroxypropylmethylcellulose, polyvinylacetal diethylaminoacetate, polyvinyl pyrrolidone, gelatin, medium chain fatty acid triglycerides, polyoxyethylene hydrogenated castor oil 60, sucrose, carboxymethyl cellulose, corn starch, and inorganic salts. The amount of the active ingredient in these preparations can be set as appropriate within the designated range of doses.

In another embodiment, the present disclosure relates to a method for preventing and/or treating atopic dermatitis comprising administering an IL-31 antagonist to a subject with or potentially with atopic dermatitis.

In this case, the IL-31 antagonist may be repeatedly administered in equal amounts at the same dosing interval to the subject with or potentially with atopic dermatitis, at 0.1 to 1000 mg/body/1 day to 12 weeks, preferably at 0.1 to 1000 mg/body/2 weeks, 0.1 to 1000 mg/body/4 weeks, or 0.1 to 1000 mg/body/8 weeks. Alternatively, the IL-31 antagonist may be repeatedly administered in equal amounts at the same dosing interval to the subject with or potentially with atopic dermatitis, at 0.01 to 10 mg/kg/1 day to 12 weeks, preferably at 0.01 to 10 mg/kg/2 weeks, 0.01 to 10 mg/kg/4 weeks, or 0.01 to 10 mg/kg/8 weeks. Furthermore, in this prophylactic or therapeutic method, the IL-31 antagonist may be administered before, simultaneously with, or after the administration of the topical steroid or the topical calcineurin inhibitor.

In another embodiment, the present disclosure provides a product comprising at least (i) a container (e.g., an injection); (ii) a pharmaceutical composition comprising an IL-31 antagonist as an active ingredient within the container; and (iii) a document instructing that the IL-31 antagonist be repeatedly administered in equal amounts at the same dosing interval to a subject with or potentially with atopic dermatitis, at 0.1 to 1000 mg/body/1 day to 12 weeks or 0.01 to 10 mg/kg/1 day to 12 weeks. Additionally, a label, a syringe, an injection needle, a pharmacologically acceptable medium, an alcohol cotton cloth, plaster, and the like may be additionally packaged, as appropriate, with this product. The container may be a bottle, a glass bottle, or a syringe, for example, and may be made of any of various materials such as glass and plastics. The container contains the pharmaceutical composition, and has an outlet sealed with a rubber stopper, for example. The container is provided with, for example, a label indicating that the pharmaceutical composition is for use in preventing or treating a selected pathological condition. In some cases, this label may describe the embodiment where the IL-31 antagonist is used in combination with the topical steroid or the topical calcineurin inhibitor.

All the technical documents cited herein are incorporated herein by reference in their entirety.

As used herein, the meaning of the term "and/or" is a combination of the terms used before and after the phrase "and/or", and is understood to include all combinations in which "and" and "or" are combined as appropriate.

The terms used herein are employed for illustrating specific embodiments, and should not be understood as limiting the invention. Unless different definitions are expressly described, the terms (including technical and scientific terms) used herein should be interpreted to have the same meanings as broadly understood by those skilled in the art to which the present disclosure pertains, and should not be interpreted in any idealized or excessively formal meaning.

The term "comprise", "comprises", or "comprising" as used herein is intended to mean the presence of the stated matter(s) (e.g., member(s), step(s), element(s), and number(s)), and does not exclude the presence of other matter(s) (e.g., member(s), step(s), element(s), and number(s)), unless it should be understood in clearly different ways in the context.

The embodiments of the present disclosure, which may be described with reference to schematic diagrams, may be expressed in an exaggerated manner for the sake of clear illustration.

A numerical value recited herein may be understood to have a certain range of variations in light of the common knowledge in the art, unless it is contradictory in the context. For example, the recitation "1 mg" is understood to be recited as "about 1 mg", and is understood to include a certain range of variations based on the disclosure of the present specification and the common knowledge in the art. Moreover, the recitation "1 to 5 times", for example, as used herein may be understood to recite "1, 2, 3, 4, or 5 times" as if to specifically and individually recite each value, unless it is contradictory in the context. Furthermore, the recitation "20, . . . 25 times", for example, as used herein may be understood to recite "20, 21, 22, 23, 24, or 25 times" as if to specifically and individually recite each value, unless it is contradictory in the context. Moreover, the recitation "1 to 5000 pg/mL", for example, as used herein may be understood to recite, for example, "1 pg/mL, 2 pg/mL, 3 pg/mL, 4 pg/mL, 5 pg/mL, 6 pg/mL, 7 pg/mL, 8 pg/mL, 9 pg/mL, 10 pg/mL, . . . 15 pg/mL, . . . 20 pg/mL, . . . 25 pg/mL, . . . 30 pg/mL, . . . 35 pg/mL, . . . 40 pg/mL, . . . 45 pg/mL, . . . 50 pg/mL, . . . 55 pg/mL, . . . 60 pg/mL, . . . 65 pg/mL, . . . 70 pg/mL, . . . 75 pg/mL, . . . 80 pg/mL, . . . 85 pg/mL, . . . 90 pg/mL, . . . 95 pg/mL, . . . 100 pg/mL, . . . 150 pg/mL, . . . 200 pg/mL, . . . 250 pg/mL, . . . 300 pg/mL, . . . 350 pg/mL, . . . 400 pg/mL, . . . 450 pg/mL, . . . 500 pg/mL, . . . 600 pg/mL, . . . 700 pg/mL, . . . 800 pg/mL, . . . 900 pg/mL, . . . 1000 pg/mL, . . . 2000 pg/mL, . . . 3000 pg/mL, . . . 4000 pg/mL, . . . 5000 pg/mL", but not limited thereto, unless it is contradictory in the context. Furthermore, the recitation "10 pg/mL, . . . 15 pg/mL", for example, as used herein may be understood to recite "10 pg/mL, 11 pg/mL, 12 pg/mL, 13 pg/mL, 14 pg/mL, or 15 pg/mL" as if it recites specifically and individually each value, unless it is contradictory in the context. Naturally, therefore, a person skilled in the art will directly and unambiguously understand that the recitation "1 to 5000 pg/mL", for example, is meant to specifically and individually recite values such as 100 pg/mL, 224 pg/ml, and 1500 pg/mL, for example. The same interpretation applies, as appropriate, to numerical values recited herein, unless it is contradictory in the context, and likewise, a person skilled in the art may naturally understand directly and unambiguously that each value is specifically and individually recited.

EXAMPLES

The present disclosure will be more specifically described hereinafter with examples; however, the present disclosure is not limited to these examples.

Example 1

Preparation of an Anti-Human IL-3 IRA Antibody

CIM331 (H chain, SEQ ID NO: 9; L chain, SEQ ID NO: 10), which is an anti-human IL-31RA antibody also described in WO 2010/064697, was prepared using a method known to those skilled in the art, in accordance with the disclosure of the aforementioned patent document. As disclosed in WO 2010/064697, CIM331 has neutralizing activity against human IL-31RA and cynomolgus monkey IL-31RA.

Example 2

Modification of Amino Acid Residues in the Antibody

An antibody wherein at least one amino acid residue that can be exposed on the antibody surface has been modified to reduce the isoelectric point (pI) of the antibody (hereinafter also referred to as the "pI-reduced antibody") can reduce intracellular uptake of the antibody, or can retard the elimination of the antibody from plasma, as disclosed or suggested in WO 2009/041643, for example. An anti-human IL-31RA antibody, CIM331, was prepared by the substitution of a plurality of sites of the amino acid residues in CDRs that can change the pI, as disclosed in WO 2009/041643 (e.g., K62Q, K64Q, and G65D in the H chain variable region; R24Q, N27aD, and L54E in the L chain variable region (Kabat numbering)).

It has been found recently that the pI can also be changed by the substitution of amino acid residues in antibody constant regions. Such a method is described in WO 2014/145159, for example.

To verify the effect of the substitution of amino acid residues in antibody constant regions upon pI, an anti-human IgE antibody was prepared using the method described in Reference Example 1. Specifically, a normal antibody Ab1 containing Ab1H (SEQ ID NO: 12) as the heavy chain and Ab1L (SEQ ID NO: 13) as the light chain was prepared.

The theoretical isoelectric point (pI) of the thus-prepared antibody was calculated by a method known to those skilled in the art, using GENETYX-SV/RC Ver 9.1.0 (GENETYX CORPORATION) (Skoog, B. and Wichman, A. 1986. Calculation of the isoelectric points of polypeptides from the amino acid composition. trends in analytical chemistry, vol. 5, No. 4, 82-83). In the antibody molecule, all the cysteine side chains were assumed to form disulfide bonds, and the calculation was performed to exclude the contribution of the pKa of the cysteine side chains. The theoretical pI of Ab1 was 6.77.

The prepared Ab1 was an antibody having a natural human IgG1 as constant regions. Here, Ab1H-P600 was created by modifying the Fc region of the heavy chain Ab1H of Ab1 by the substitution of proline at position 238 and serine at position 298 as defined by the EU numbering with aspartic acid and alanine, respectively. Furthermore, an Fc variant was prepared (Ab1H-P850) using the method described in Reference Example 1, by introducing a Q419K (EU numbering) mutation, which is a substitution of an uncharged amino acid with a positively charged amino acid, into the Fc region of Ab1H-P600. Ab1L (SEQ ID NO: 13) was used as the light chain.

Concerning an antibody containing the prepared Fc variant (Ab1H-P850), an experiment was performed using Biacore T200 (GE Healthcare) on binding between soluble human Fcγ R2b (also referred to as "human Fcγ RIIb" or "hFcγ R2b") and an antigen-antibody complex. The soluble human Fcγ R2b was prepared in the form of a His-tagged molecule, using a method known to those skilled in the art. An appropriate amount of an anti-His antibody was immobilized onto Sensor Chip CM5 (GE Healthcare) by the amine coupling method, using His capture kit (GE Healthcare), and the human Fcγ R2b was captured thereon. Next, the antigen-antibody complex and a running buffer (as a reference solution) were injected, and interacted with the human Fcγ R2b captured on the sensor chip. As the running buffer, 20 mM N-(2-acetamide)-2-aminoethanesulfonic acid, 150 mM NaCl, 1.2 mM $CaCl_2$, and 0.05% (w/v) Tween 20, pH 7.4 were used, and this buffer was also used for dilution of the soluble human Fcγ RIIb. For regeneration of the sensor chip, 10 mM glycine-HCl, pH 1.5 was used. All measurements were conducted at 25° C. Analysis was performed based on the binding (RU) calculated from the sensorgram obtained by the measurements, and the result was expressed as a relative value when the amount of binding obtained with P600 was taken as 1.00. For calculation of parameters, Biacore T100 Evaluation Software (GE Healthcare) was used.

As a result, a comparison between Ab1H-P600 and Ab1H-P850 showed that the binding property for hFcγ R2b immobilized onto the Biacore sensor chip was increased in Ab1H-P850 (when the value for Ab1H-P600 was taken as 1.00, the value for Ab1H-P850 was 2.22). The affinity of Ab1H-P850 for hFcγ R2b per se had been verified to be comparable to the affinity of Ab1H-P600 for hFcγ R2b per se, using Biacore (data not shown).

While not being bound by a specific theory, this result can be explained as follows.

It is known that the Biacore sensor chip is negatively charged, and the charged state can be considered to be similar to a cell membrane surface. Hence, it is inferred that the binding property of the antigen-antibody complex for hFcγ R2b immobilized onto the negatively charged Biacore sensor chip is similar to the way in which the antigen-antibody complex binds to hFcγ R2b present on a cell membrane surface that is similarly negatively charged.

Here, in the antibody containing the Fc variant (Ab1H-P850) obtained by introducing the modification that increases the pI into position 419 of the Fc region, the charge of the Fe region is more on the positive side, compared to that before the introduction of the modification (antibody containing Ab1H-P600). It can therefore be thought that the Coulomb interaction between the Fc region (positive charge) and the sensor chip (negative charge) was strengthened by the amino acid modification that increases the pI. Furthermore, this effect is expected to similarly occur on the cell membrane surface similarly having a negative charge. Hence, it is expected that the effect of accelerating the rate of intracellular uptake in vivo will be demonstrated.

Conversely, if an Fc variant obtained by introducing an amino acid that reduces the pI (e.g., aspartic acid or glutamic acid) into position 419 of the Fc region is used, the charge of the Fc region will be more on the negative side, compared to that before the introduction of the modification. As a result, the Coulomb interaction between the Fc region (negative charge) and the cell membrane surface (negative charge) will be weakened by the amino acid modification that reduces the pI. This will be expected to retard the rate of intracellular uptake in vivo, and demonstrate the effect of increasing the plasma half-life of the antibody. Ab1 is an antibody having a natural human IgG1 as constant regions, and the amino acid residue at position 419 (EU numbering) is glutamine (Q) in all of natural human IgG1 to IgG4. Thus, a person skilled in the art will understand that regardless of the type of IgG, the above-described result can be similarly observed.

The amino acid sequence of CIM331 has an amino acid variation bearing the substitution Gln(Q)419Glu(E).

In relation with a nonclinical study preceding the clinical study of CIM331, the following important fact to be noted was found. The antigen-antibody interaction of CIM331 with IL-31RA from each of mouse, rat, and rabbit was evaluated with Biacore (Biacore T100 (GE Healthcare)), using a method known to those skilled in the art. As a result, it was revealed that CIM331 does not exhibit cross-reactivity with IL-31RA from any of mouse, rat, and rabbit (Sakurai T, Esaki K. Cross-reactivity of CH5427227 with NR10 (IL-31RA) from mice, rats and rabbits (Study No. TOX08-0198S). Chugai Pharmaceutical Co., Ltd. In-house report, 2010.).

Thus, to verify the below-described effect concerning the dosage of CIM331 in humans and the dosing interval, even a person skilled in the art needed to actually administer CIM331 to humans, or needed to administer CIM331 to human models (e.g., cynomolgus monkeys) exhibiting cross-reactivity, and then predict the effect by extrapolating the results to humans.

Example 3A

Suppressive Effect of Subcutaneous Administration of CIM331 on IL-31-Induced Pruritus in Cynomolgus Monkeys The effect of subcutaneous administration of CIM331 on pruritus induced by intravenous administration of cynomolgus monkey IL-31 to cynomolgus monkeys was studied. The frequency of pruritic behavior was measured as an index of reactivity to pruritus. The frequency of pruritic behavior was measured visually by watching the video recordings (2 hours) of each monkey's behavior, and the movement of scratching a part of the body with a front or hind leg was counted as one occurrence of pruritic behavior. However, pruritic behaviors that ended in one or two scratching movements were excluded from the frequency of pruritic behavior because they were considered to be coincidental events.

First, before the administration of CIM331, the behavior of each animal without the administration of cynomolgus monkey IL-31 was recorded with a video camera (2 hours). Subsequently, the behavior of each animal was observed by playing back the video, and the frequency of pruritic behavior without the administration of cynomolgus monkey IL-31 was measured using the above-described method.

A single subcutaneous dose of 0.2 or 1 mg/kg of CIM331 was administered to cynomolgus monkeys, and the frequency of pruritic behavior after the administration of cynomolgus monkey IL-31 was measured as follows, to evaluate the effect of subcutaneous administration of CIM331. A single subcutaneous dose of 0.2 mg/kg of CIM331 was administered to cynomolgus monkeys, and 1 μg/kg of cynomolgus monkey IL-31 was intravenously administered before the subcutaneous administration of CIM331 and on days 3, 15, 28, 42, 56, and 93 after the subcutaneous administration of CIM331. After the administration of cynomolgus monkey IL-31, the individual behavior was recorded with a video camera (2 hours). Likewise, a single subcutaneous dose of 1 mg/kg of CIM331 was administered to cynomolgus monkeys, and 1 μg/kg of cynomolgus monkey IL-31 was intravenously administered before the subcutaneous administration of CIM331 and on days 28, 42, 56, 77, 79, 81, 84, and 93 after the subcutaneous administration of CIM331. After the administration of cynomolgus monkey IL-31, the individual behavior was recorded with a video camera (2 hours). The individual behavior was subsequently observed by playing the video, and the frequency of pruritic behavior after the administration of cynomolgus monkey IL-31 was measured using the above-described method.

It was verified that the administration of cynomolgus monkey IL-31 before the administration of CIM331 induced pruritus in that it increased the frequency of pruritic behavior, compared to that before the administration of cynomolgus monkey IL-31. It was also verified that the administration of a single subcutaneous dose of CIM331 to cynomolgus monkeys reduced the frequency of pruritic behavior after the administration of cynomolgus monkey IL-31.

Figure 6:
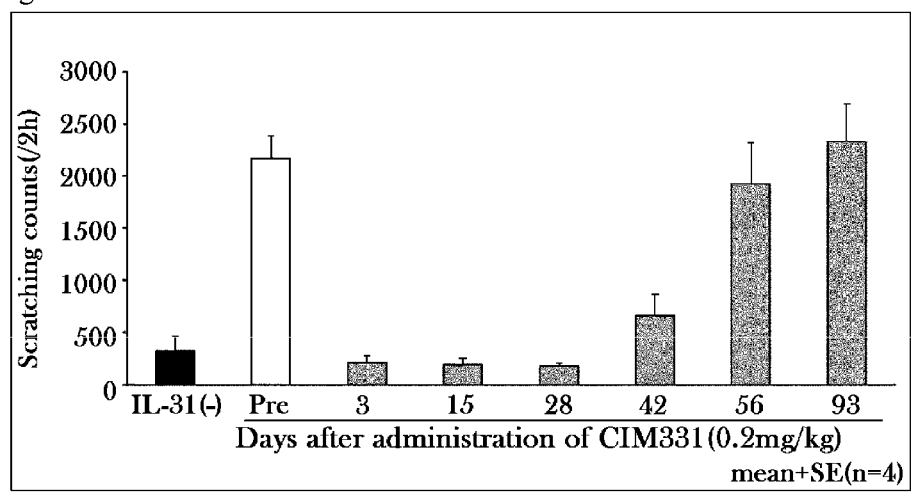
FIG. 6 is a graph showing the frequency of IL-31-induced pruritic behavior after the administration of a single subcutaneous dose of 0.2 mg/kg of CIM331 to cynomolgus monkeys.
Figure 7:
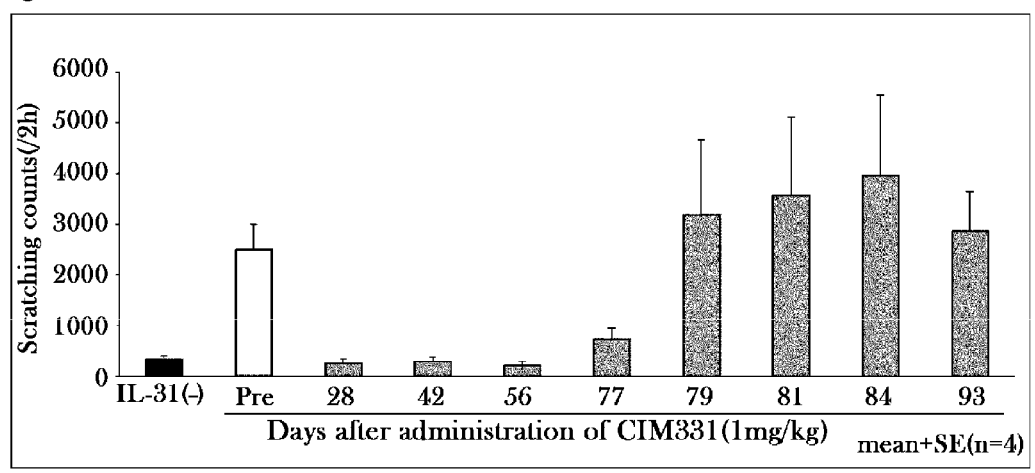
FIG. 7 is a graph showing the frequency of IL-31-induced pruritic behavior after the administration of a single subcutaneous dose of 1 mg/kg of CIM331 to cynomolgus monkeys.

The administration of a single subcutaneous dose of 0.2 mg/kg of CIM331 to cynomolgus monkeys was shown to reduce the mean value of the frequency of pruritic behavior after the administration of cynomolgus monkey IL-31 in the evaluation on day 3 after the CIM331 administration, compared to that before the CIM331 administration; and was shown to reduce the mean value of the frequency of pruritic behavior after the administration of cynomolgus monkey IL-31 even on day 42 after the CIM331 administration (FIG. 6). Furthermore, the administration of a single subcutaneous dose of 1 mg/kg of CIM331 was shown to reduce the mean value of the frequency of pruritic behavior after the administration of cynomolgus monkey IL-31, even on day 77 after the CIM331 administration (FIG. 7).

Figure 8:
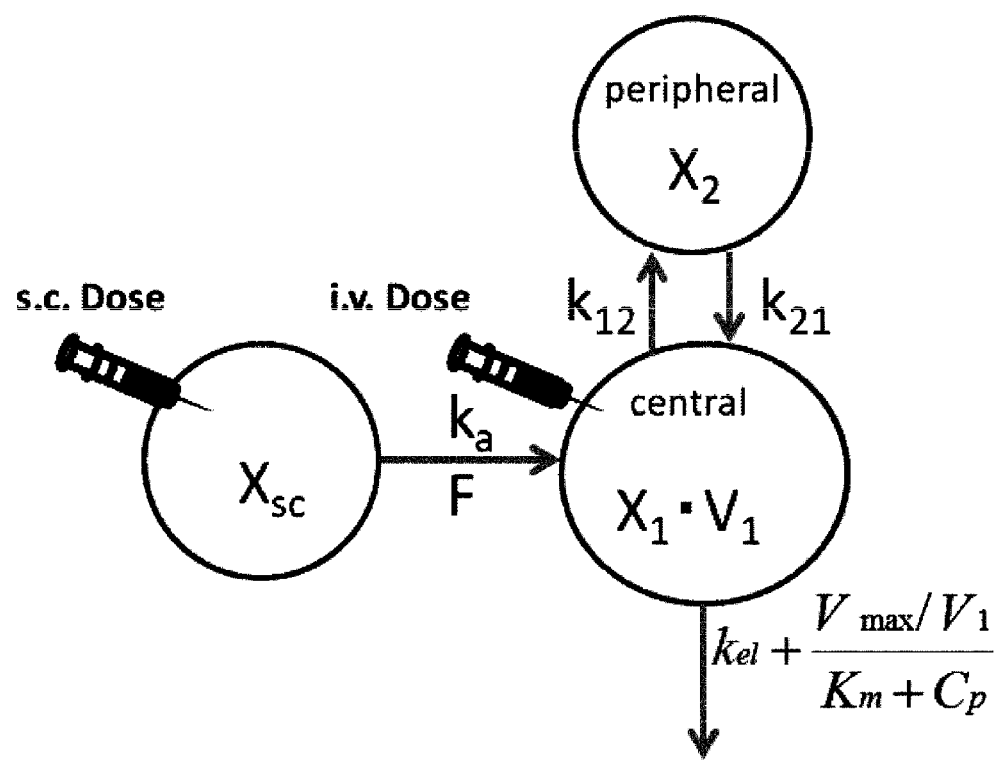
FIG. 8 shows a nonlinear analytical model adopting the Michaelis-Menten equation, wherein the symbols designate the following: $X_{sc}$: the amount of drug at the site of subcutaneous administration; $X_1$: the amount of drug in a central compartment; $X_2$: the amount of drug in a peripheral compartment; F: bioavailability; $k_{12}$: the drug transfer rate constant from the central compartment to the peripheral compartment; $k_{21}$: the drug transfer rate constant from the peripheral compartment to the central compartment; $k_a$: the absorption rate constant; $k_{el}$: the non-saturable elimination rate constant; Vi: the distribution volume of the central compartment; $V_{max}$: the elimination rate of the antibody when the antibody binds to all the receptors: $K_m$: the antibody concentration for binding to 50% of the entire amount of antigen; and $C_p$: the antibody concentration.

For setting a dosage for humans, the effective plasma concentration of CIM331 was determined from the outcome of a study using an in vivo cynomolgus monkey IL-31-induced pruritus model in which systemic pruritus was induced by the administration of cynomolgus monkey IL-31 to a cynomolgus monkey. In this study, CIM331 was intravenously administered to the same cynomolgus monkey individual while gradually increasing the dosage from 3 to 100 μg/kg (3, 10, 40, 60, and 100 μg/kg) to increase the plasma concentration. On the day following the CIM331 administration in each stage, blood was collected to measure the plasma concentration of CIM331. Additionally, pruritic behavior induced by intravenous administration of 1 μg/kg of cynomolgus monkey IL-31 was recorded with a video camera for 2 hours after the administration, and the frequency of pruritic behavior was measured. To measure the frequency of pruritic behavior, the behavior of the monkey recorded with a video camera (2 hours) was visually observed, and the movement of scratching a part of the body with a forelimb or hindlimb was counted as one occurrence of pruritic behavior. However, a pruritic behavior that ended in one or two scratching movements was considered to be accidental, and excluded from the frequency of pruritic behavior. By intravenously administering CIM331 while gradually increasing the dosage, the mean plasma concentration of CIM331 on the day following the CIM331 administration was gradually increased, depending on the dosage. CIM331 demonstrated an evident suppressive effect on cynomolgus monkey IL-31-induced pruritus subsequent to the administration of 40 μg/kg of CIM331 (the mean plasma concentration on the day following the administration was 670 ng/mL). A mean plasma concentration of 670 ng/mL was defined as the estimated effective serum concentration of CIM331 in humans. It has been reported that the in vivo pharmacokinetics of antibodies is similar between human and cynomolgus monkey (Jennifer Q. Dong et al., Quantitative Prediction of Human Pharmacokinetics for Monoclonal Antibodies. Clin Pharmacokinet 2011; 50(2): 131-142; Jie Ling et al., Interspecies Scaling of Therapeutic Monoclonal Antibodies: Initial Look. J Clin Pharmacol 2009:49 (12):1382-1402; Rong Deng et al., Projecting human pharmacokinetics of therapeutic antibodies from nonclinical data. mAbs 2011:3(1):61-66). Thus, PK parameters obtained by nonlinear analysis of data on changes in the plasma concentration of CIM331 in a cynomolgus monkey PK study were used as predicted values of PK parameters in humans. For the nonlinear analysis, a nonlinear analytical model adopting the Michaelis-Menten equation as shown in FIG. 8 was used.

Figure 9:
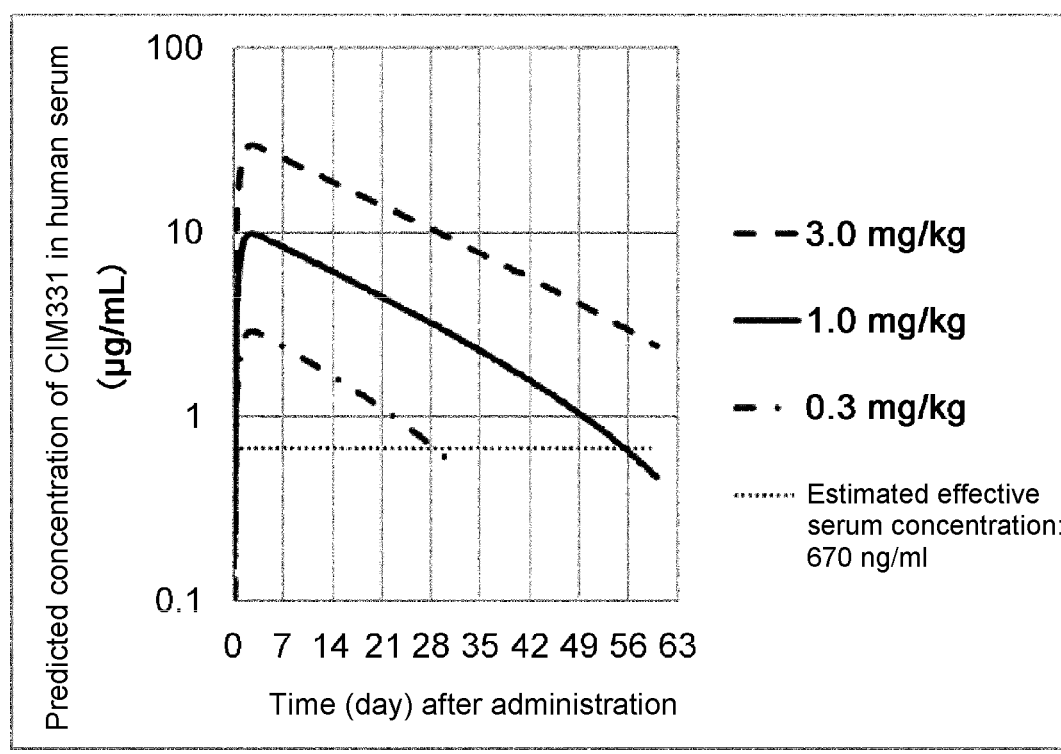
FIG. 9 shows predicted changes in the concentration of CIM331 in human serum.

After intravenous and subcutaneous administration of CIM331 at 0.04 mg/kg, 0.2 mg/kg, and 1.0 mg/kg to cynomolgus monkeys, the mean values of changes in the plasma concentration of CIM331 for the respective groups were applied to the above-described model simultaneously, and optimal parameters were calculated. Using the obtained parameters, changes in the serum concentration that would result from the administration of CIM331 to humans were predicted. It was predicted that when 1 mg/kg of CIM331 was administered to humans, a serum concentration of CIM331 not lower than 670 ng/mL, i.e., the estimated effective serum concentration of CIM331 in humans, would be maintained for 56 days (FIG. 9). A dose of 1 mg/kg, at which it is expected that CIM331 can reliably maintain the effect of inhibiting IL-31 signaling for a period of 1 month or longer, was defined as the expected clinical optimal dose.

Example 3B

Single Subcutaneous Dose Administration to Patients with Atopic Dermatitis

In test drug groups in a phase I single dose study, one of CIM331 dosages of 0.3 mg/kg, 1 mg/kg, and 3 mg/kg per body weight, and placebo was subcutaneously administered in a single dose into the abdomen of each of 36 patients with atopic dermatitis who met the following criteria, each group including 9 patients.

As the patients administered with CIM331, patients with atopic dermatitis were selected who met the following criteria although they underwent treatment with a topical steroid for a duration of 12 weeks or longer:
    An Eczema Area Severity Index score of 10 or more, and rash with intense inflammation affecting 5% or more of the body surface area.
    A total score of 4 or more in the evaluation of the degree of itchiness in the daytime and nighttime based on Shiratori's severity classification.
    A pruritus VAS mean value ≤50 mm For use as an investigational drug, a preparation was obtained by filling a vial with 1 mL of a solution containing 100 mg of the CIM331 antibody per milliliter, or by diluting the solution to an intended concentration for administration. Saline solution was used as the placebo.

(3-1) Endpoint: Pruritus

The intensity of pruritus was evaluated using the Visual Analog Scale (VAS). The VAS consists of a 100-mm straight line, on which patients indicate the intensity of itchiness when awakening and when going to bed by drawing a line between 0 to 100 mm, where 0 mm represents no itchiness, and 100 mm represents the severest itchiness that patients with atopic dermatitis ever experienced. The patients kept records every day during the period of the study.

As a result, the placebo group showed a change in VAS that is approximately a 20% decrease, whereas all the dose groups of the CIM331-treated groups showed a decrease in VAS from week 1 after the administration, and maintained approximately a 50% decrease even from week 4 after the administration and thereafter (FIG. 1).

(3-2) Endpoint: Dermatitis

The Eczema Area Severity Index (EASI) score is a tool for assessing the severity and the range of atopic dermatitis. The extent and the proportion of eczema in representative affected areas were evaluated for each of the four areas, i.e., the head and neck, the upper limb, the trunk, and the lower limb, and the degrees of redness (erythema), thickness (induration, papules, and edema), excoriations (scratch marks), and lichenification were evaluated on a scale of (0) none, (1) mild, (2) moderate, and (3) severe. During the clinical study period, a doctor made assessments at a frequency of once in 1 or 2 weeks. Mean variations in the EASI score at week 4 after the administration from baseline were analyzed according to the percent decrease in the pruritus VAS score at week 4 after the administration (i.e., a group showing a percent decrease of less than 50% and a group showing a percent decrease of 50% or more).

Figure 2:
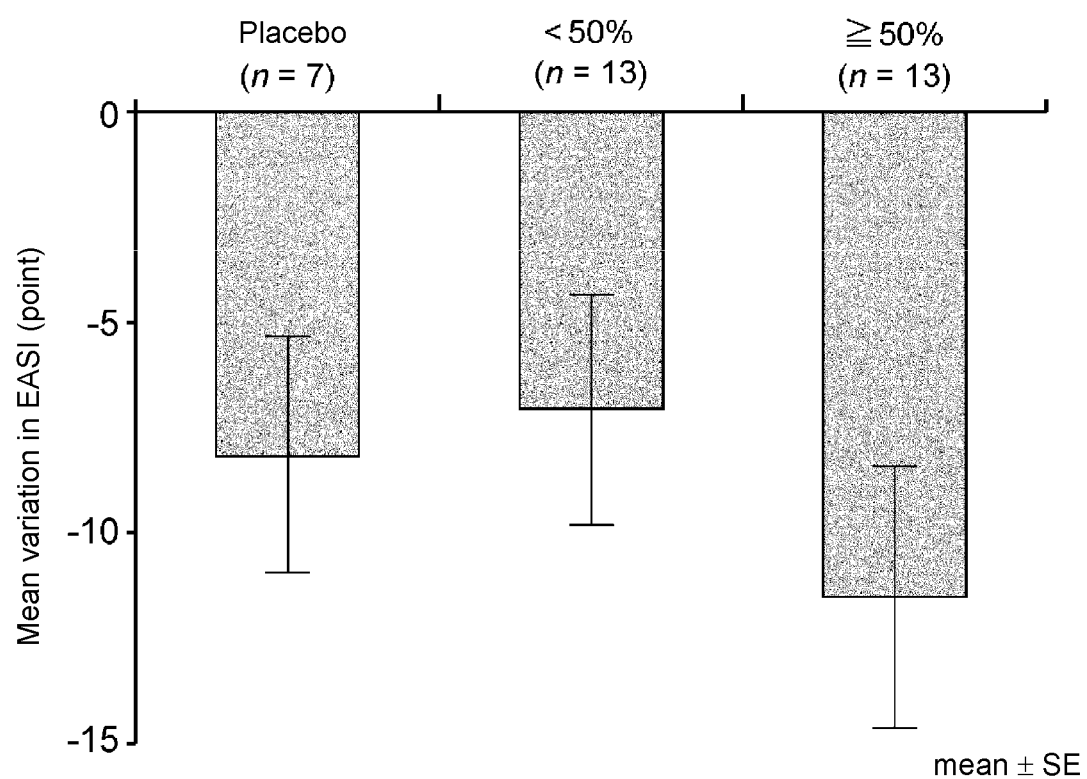
FIG. 2 is a graph showing the effects of improving dermatitis based on the EASI score, after the administration of single subcutaneous doses of CIM331 or placebo to predetermined patients with atopic dermatitis.

As a result, in the group showing a percent decrease of 50% or more in the pruritus VAS score, the mean variation in the EASI score was −11.5 points, and the decrease in the EASI score was greater than that in the placebo group or the group showing a percent decrease of less than 50% in the pruritus VAS score (FIG. 2).

(3-3) Endpoint: Quality of Life (QOL)

(3-3-1) Sleep

Actiwatch (registered trademark) is a noninvasive measurement device designed to be worn around a wrist, and capture, record, and store movements of the wrist that serve as an index of systemic movement while the user can behave freely. The subjects wore this device until week 4 after the administration. Other parameters including the actual sleep time from falling asleep to awakening, sleep onset latency, and sleep efficiency were measured using an objective method. Sleep efficiency was calculated based on the following equation:

$$\text{Sleep Efficiency} = \frac{\text{Actual Sleep Time}}{\text{Time Lying in Bed}} \quad \text{[Expression 1]}$$

Figure 3:
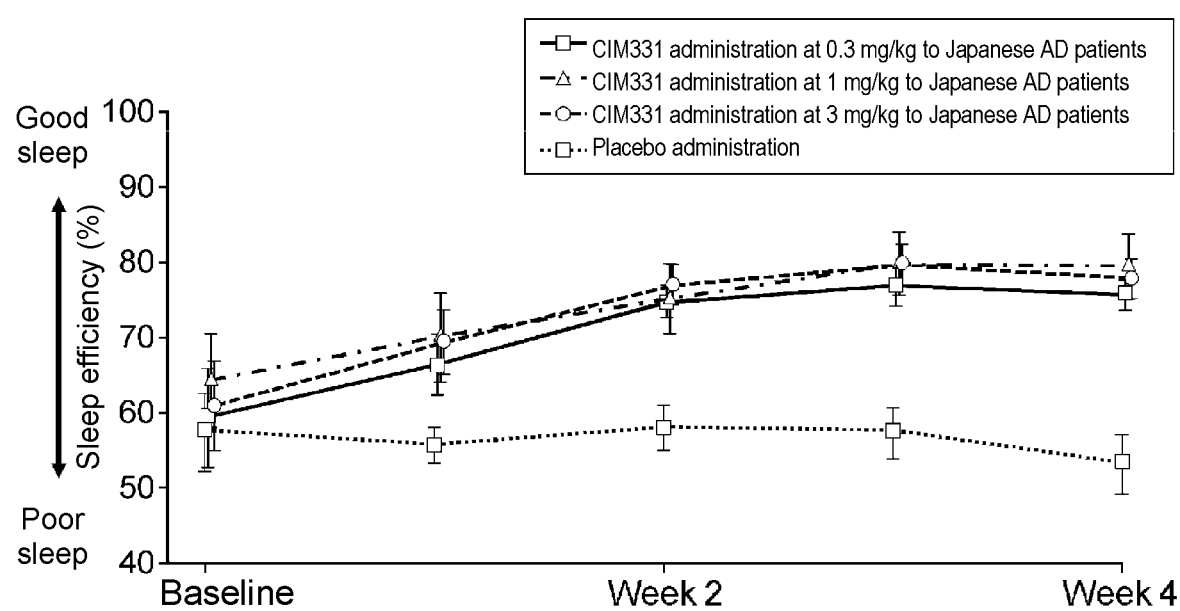
FIG. 3 is a graph showing the presence or absence of improvement in quality of life (QOL), using sleep efficiency as an index, after the administration of single subcutaneous doses of CIM331 or placebo to predetermined patients with atopic dermatitis.

As a result, although the sleep efficiency was approximately 60% in all the groups before the administration, all the dose groups of the CIM331-treated groups showed an improvement in sleep efficiency from week 1 after the administration, and showed an improvement up to approximately 80% at week 4 after the administration (FIG. 3).

(3-3-2) DLQI

The Dermatology Life Quality Index is a dermatologic tool, DLQI for evaluating the QOL (Finlay et al. 1994), and consists of 10 questions. The DLQI questions can be grouped under the following six items: symptoms and feelings, daily activities, leisure, work and school, personal relationships, and treatment. The DLQI is determined by summarizing the scores for all the items of questionnaire. The maximum score is 30, and the minimum score is 0. A higher score indicates lower QOL.

The patients kept records every 2 or 4 weeks. As a result, at week 4 after the administration, the placebo group showed a 0.7-point decrease on average, whereas the CIM331-treated groups showed a 5.4- to 6.3-point decrease on average.

(3-4) Endpoint: Amount of Topical Steroid Used

A topical steroid (Locoid (registered trademark); hydrocortisone butyrate) was used in combination with CIM331 in all the patients. The amount of the topical steroid used could be varied as appropriate, depending on the condition of the patient.

As a result, the amount of Locoid used tended to increase in the placebo-treated group, whereas the amount of Locoid used tended to decrease from week 1 after the administration in all the dose groups of the CIM331-treated groups (FIG. 4).

Figure 5:
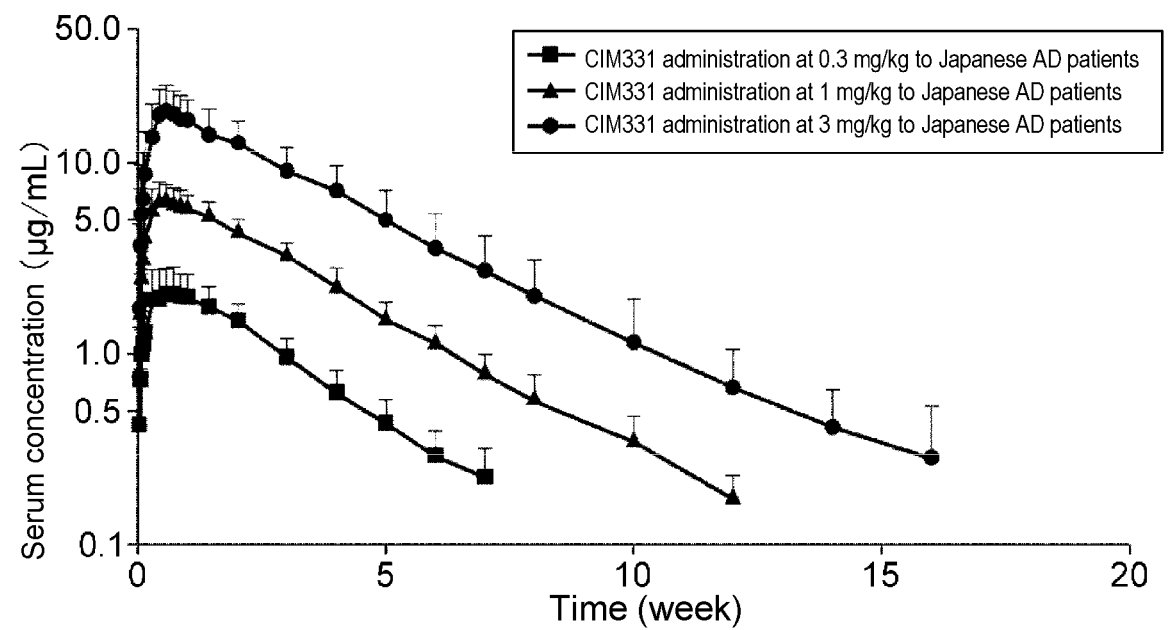
FIG. 5 is a graph showing changes in the serum concentration of CIM331 after the administration of single subcutaneous doses of CIM331 to predetermined patients with atopic dermatitis.

(3-5) Endpoint: Changes in Serum Concentration of CIM331 and Pharmacokinetic Parameters FIG. 5 shows changes in the serum concentration of CIM331 in Japanese patients with atopic dermatitis, and Table 1 shows pharmacokinetic parameters.

TABLE 1

| Step | $AUC_{inf}$ (day * μg/mL) | $AUC_{last}$ (day * μg/mL) | CL/F (mL/day) | $C_{max}$ (μg/mL) | MRT (day) | $t_{1/2}$ (day) | $T_{max}$ (day) |
|---|---|---|---|---|---|---|---|
| C-1 (Japanese, 0.3 mg/kg) | 49.2 | 45.7 | 408 | 2.20 | 19.9 | 12.6 | 5.66 |
| C-2 (Japanese, 1.0 mg/kg) | 161 | 158 | 368 | 6.50 | 22.1 | 13.2 | 4.87 |
| C-3 (Japanese, 3.0 mg/kg) | 489 | 484 | 459 | 19.4 | 23.7 | 14.6 | 4.46 |

As a result, on days 4.46 to 5.66 (mean value; the same applies below) after the administration of CIM331, CIM331 reached its maximum serum concentration, and thereafter showed mild elimination with serum elimination half-lives ($t_{1/2}$) of days 12.6 to 14.6. The $C_{max}$ for the 0.3 mg/kg group, 1 mg/kg group, and 3 mg/kg group were 2.20, 6.50, and 19.4 μg/mL, respectively, and the $AUC_{inf}$ were 49.2, 161, and 489 day*μg/mL, respectively. Moreover, the $AUC_{inf}$, $AUC_{last}$, and $C_{max}$ upon administration of the single subcutaneous doses of CIM331 increased dose-proportionally. The serum concentration of CIM331 dose-dependently showed a tendency to prolong the period during which the concentration was maintained at a certain level or higher. Meanwhile, the relation between the pruritus-suppressing effect of the CIM331 administration and exposure was not clear in this study.

The terms used in the table refer to the following:

$AUC_{inf}$: AUC from time zero extrapolated to infinite time $AUC_{last}$: AUC from time zero until the last measurable plasma concentration CL/F: apparent clearance $C_{max}$: maximum blood concentration MRT: mean residence time $t_{1/2}$: elimination half-life $T_{max}$: time to maximum blood concentration (3-6) Exploratory Endpoint: Efficacy It was found from these results that CIM331 improved the pruritus, dermatitis, and QOL of the patients with atopic dermatitis. This study is the first clinical study outcome report showing that the IL-31 antagonist is effective against pruritus due to atopic dermatitis. CIM331 can thus be expected to provide improvements not only in pruritus due to atopic dermatitis, but also in dermatitis and QOL, based on the novel mechanism of action that blocks the itch-scratch cycle. It is known that scratching caused by pruritus is an exacerbating factor that aggravates rash. Scratching mechanically damages the skin to reduce the barrier function. Foreign antigens that have invaded through the epidermis increase inflammatory responses. This leads to aggravation of dermatitis and an exacerbation of pruritus. This vicious circle of scratching-dermatitis aggravation-pruritus aggravation is known as the itch-scratch cycle (e.g., Wahlgren C F. J Dermatol 1999; 26: 770-9; Homey B, et al. J Allergy Clin Immunol 2006; 118: 178-89).

Example 4

Repeated Subcutaneous Dose Administration to Patients with Atopic Dermatitis (4-1) Phase II Repeated Dose Study In test drug groups in a phase II repeated dose study, about 250 patients with moderate or severe atopic dermatitis for which topical therapy was not sufficiently effective or was intolerable were subcutaneously administered in the abdomen with either CIM331 or placebo, as outlined below. The dosages of CIM331 per body weight and the concentrations of the CIM331 solution for administration were as shown below. The CIM331 solution for administration was slowly administered in a volume of 20 μL/kg per body weight. When the body weight of a subject exceeded 120 kg, an investigational drug was prepared on the assumption that the body weight was 120 kg. The investigational drug was prepared as follows: A preparation obtained by filling each vial with 1.53 mL of a solution containing 100 mg of the CIM331 antibody per mL, and freeze-drying the solution, was dissolved in water for injection to provide a solution for administration. This solution for administration was further diluted with a separate placebo solution to an intended concentration for administration.

TABLE 2

| CIM331 Dose (mg/kg) | Concentration of CIM331 Solution for Administration (mg/mL) |
| --- | --- |
| 0.1 | 5 |
| 0.5 | 25 |
| 2.0 | 100 |

As the patients to be administered with CIM331, patients with atopic dermatitis were selected for which the administration of a topical steroid or a topical calcineurin inhibitor at a fixed dosage for a duration of 4 weeks or longer was not sufficiently effective, or for which standard topical therapy was intolerable, or for which standard topical therapy was prohibited (due to contraindications and the like), and who met the following criteria:

An Eczema Area Severity Index score of 10 or more
A sIGA score of 3 or more
Pruritus VAS score ≤50 mm This clinical study consisted of two parts. Part A was a randomized, double-blind, placebo-controlled, parallel-group comparison study (weeks 0 to 12). Part B was a double-blind extension period, during which the CIM331 administration to the subjects was continued for additional 52 weeks (weeks 12 to 64). About 250 subjects in Part A were randomly allocated to one of four test drug groups (about 50 subjects per group) and a placebo group (about 50 subjects) in a ratio of 1:1:1:1:1.

Part A

CIM331 (0.1 mg/kg) was subcutaneously administered every 4 weeks (administered at day 1, week 4, and week 8).

CIM331 (0.5 mg/kg) was subcutaneously administered every 4 weeks (administered at day 1, week 4, and week 8).

CIM331 (2.0 mg/kg) was subcutaneously administered every 4 weeks (administered at day 1, week 4, and week 8).

CIM331 (2.0 mg/kg) was subcutaneously administered every 8 weeks (CIM331 administered at day 1 and week 8, and placebo administered at week 4).

The placebo was subcutaneously administered every 4 weeks (administered at day 1, week 4, and week 8).

More specifically, there were 264 patients who received the administration of the investigational drug or placebo at least once in Part A, and there were 53, 53, 54, 52, and 52 patients, respectively, in the placebo group, the groups to which CIM331 was subcutaneously administered every 4 weeks at 0.1 mg/kg, 0.5 mg/kg, and 2.0 mg/kg, and the group to which CIM331 was subcutaneously administered every 8 weeks at 2.0 mg/kg.

Part B

The subjects who were allocated to the placebo group in Part A were randomly re-allocated to groups to which CIM331 (0.1 mg/kg, 0.5 mg/kg, and 2.0 mg/kg) was subcutaneously administered every 4 weeks in Part B.

The subjects who were randomly allocated to the test drug groups in Part A were re-allocated to the same dose groups as in Part A, and continued to receive the same treatment from week 12 and thereafter.

CIM331 (0.1 mg/kg) was subcutaneously administered every 4 weeks for a total period of 52 weeks.

CIM331 (0.5 mg/kg) was subcutaneously administered every 4 weeks for a total period of 52 weeks.

CIM331 (2.0 mg/kg) was subcutaneously administered every 4 weeks for a total period of 52 weeks.

CIM331 (2.0 mg/kg) was subcutaneously administered every 8 weeks for a total period of 52 weeks (CIM331 and the placebo were alternately administered every 4 weeks to the subjects in this group).

(4-2) Rescue Therapy

For subjects who did not demonstrate an improvement in pruritus VAS or skin condition, the use of a topical drug was allowed as rescue therapy based on a doctor's judgement from week 4 after the initial administration and thereafter. The definition of "did not demonstrate an improvement" means cases where all of the following conditions are met:

(1) no improvement in the sIGA score from baseline was demonstrated;

(2) the sIGA score was 3 or more; and (3) the percent improvement in pruritus VAS from baseline was less than 10%, and the latest pruritus VAS score was 50 mm or more.

(4-3) Endpoints:

The intensity of pruritus was evaluated using the Visual Analog Scale (VAS) (Furue et al. 2013). The VAS consists of a 100-mm straight line, on which the patients indicate the intensity of itchiness in the past 24 hours by drawing a line between 0 to 100 mm, wherein 0 mm represents no itchiness, and 100 mm represents the worst imaginable itchiness.

The verbal rating scale (VRS) for pruritus is a VRS on which the subjects evaluate the degree of pruritus in the past 24 hours on a scale of (0) no itchiness, (1) mild itchiness, (2) moderate itchiness, (3) severe itchiness, and (4) very severe itchiness (Reich et al. 2012).

The Eczema Area Severity Index (EASI) score is a tool for assessing the severity and the range of atopic dermatitis. The extent and the proportion of eczema in representative affected areas were evaluated for each of the four areas, i.e., the head and neck, the upper limb, the trunk, and the lower limb, and the degrees of redness (erythema), thickness (induration, papules, and edema), excoriations (scratch marks), and lichenification were evaluated on a scale of (0) none, (1) mild, (2) moderate, and (3) severe.

SCORing Atopic dermatitis (SCORAD) is a clinical tool for assessing the range and severity of eczema (European Task Force on Atopic Dermatitis 1993).

static Investigator's Global Assessment (sIGA) comprehensively assesses severity at the time of the evaluation using the clinical characteristics, i.e., erythema, infiltration, papules, exudation, and crusts, on a six scale from clear to very severe disease (0=clear, 1=almost clear, 2=mild disease, 3=moderate disease, 4=severe disease, 5=very severe disease).

The body surface area (BSA) of atopic dermatitis lesions represents the proportion of the lesions in the entire body.

The VAS for sleep disturbance is a VAS on which the subjects evaluate the extent of sleep disturbance in the past 24 hours from a scale of (0) "no sleep problems" to (10) "no sleep at all" (Furue et al. 2013).

The Dermatology Life Quality Index is a dermatologic tool for evaluating the QOL (Finlay et al. 1994), and consists of 10 questions. The DLQI questions can be grouped under the following six items: symptoms and feelings, daily activities, leisure, work and school, personal relationships, and treatments. The DLQI is determined by summarizing the scores for all the items of questionnaire. The maximum score is 30, and the minimum score is 0. A higher score indicates lower QOL.

Actigraphy

Actiwatch is a noninvasive measurement device designed to be worn around a wrist, and capture, record, and store movements of the wrist that serve as an index of systemic movement while the user can behave freely. The subjects wore this device from the start of the pre-observation period until week 4. Other parameters including the actual sleep time from falling asleep to awakening, sleep onset latency, and sleep efficiency were measured using an objective method.

(4-4) Analysis Means, Analysis Method, and the Like:

In the groups to which CIM331 was subcutaneously administered every 4 weeks, the percent improvement in pruritus VAS at week 12 after the start of administration compared to that at the start of administration was used as the primary endpoint to verify the superiority and efficacy of each dose group to which CIM331 was administered once every 4 weeks, compared to the placebo group. Analysis of covariance (ANCOVA) was used as the primary analysis method. Specifically, a model was fitted in which the percent improvement in pruritus VAS at week 12 after the start of administration compared to that at the start of administration was used as a response variable, the treated groups were used as fixed effects, and pruritus VAS score at the start of administration and the regions (Japan, Europe, and the United States) were used as covariates. In the primary analysis, using a one-sided significance level of 0.025 as the significance level of the test, multiplicity due to the repetition of tests was considered by performing comparisons between two groups successively from a high dose, based on the principle of the closed testing procedure. As the primary analysis set, the per-protocol (PP) set was used which excluded, for example, some subjects who demonstrated a serious deviation from the protocol, subjects who withdrew from the clinical study in an early stage, and subjects who were administered with an investigational drug different from those allocated. Data measured after the receipt of rescue therapy were all excluded, and missing values were complemented using LOCF (Last Observation value Carrying Forward after baseline).

Of the patients who received the administration of the investigational drug or placebo in Part A, the primary analysis set included 46, 46, 45, 47, or 45 patients, respectively, in the placebo group, the groups to which CIM331 was subcutaneously administered every 4 weeks at 0.1 mg/kg, 0.5 mg/kg, or 2.0 mg/kg, or the group to which CIM331 was subcutaneously administered every 8 weeks at 2.0 mg/kg.

Between each of the groups to which CIM331 was administered every 4 weeks and the placebo group, the difference (least square mean) in the percent improvement in pruritus VAS at week 12 after the start of administration compared to that at the start of administration, which was used as the primary endpoint, was −21.39% (p=0.0027), −41.16% (p<0.0001), or −40.39% (p<0.0001) in the 0.1 mg/kg, 0.5 mg/kg, or 2.0 mg/kg group, respectively.

Moreover, since this study is an exploratory dose-finding study, secondary analysis besides the primary analysis can be performed to make a comprehensive investigation of dosages. In this case, although the study is exploratory, a one-sided significance level of 0.025 as the significance level of the test is used as a guide. While not intended to be limiting, specifically, besides ANCOVA, the use of a mixed-effects model repeated measures approach (MMRM), the aggregation of summary statistics independent of a model, the use of the Intent-to-Treat (ITT) analysis set using all the available data obtained at a prescribed observation point after the administration of the investigational drug, and the use of data measured after the receipt of rescue therapy may be contemplated. Alternatively, the results of analysis without compensation of missing values may be checked as appropriate, and comprehensively studied. Furthermore, using pruritus VAS at a time point other than week 12 after the start of administration, or using a variation corresponding to a percent improvement in pruritus VAS compared to that at the start of administration or values at various time points, analysis of a model using the proportion of improved cases based on their continuous quantity or a certain threshold as a response variable may be evaluated. Important subpopulations may be considered for this analysis. A secondary efficacy endpoint besides the pruritus VAS may be similarly analyzed.

A similar exploratory comparison can also be performed on the group to which CIM331 was subcutaneously administered every 8 weeks.

Proportion of Improved Subjects: Pruritus VAS, EASI, and SCORAD

For each endpoint, the proportion of subjects who demonstrated an improvement of 25%, 50%, or 75% from baseline until each time point was calculated.

With respect to the results for the groups to which CIM331 was administered every 4 weeks in Part A, data measured after the receipt of rescue therapy in the PP set were all excluded, and missing values were complemented using LOCF. In this case, the proportion of subjects who demonstrated an improvement of 50% in pruritus VAS at week 12 after the start of administration was 41%, 67%, or 59% in the 0.1 mg/kg group, 0.5 mg/kg group, or 2.0 mg/kg group, respectively, compared to 21% in the placebo group. The proportion of subjects who demonstrated an improvement of 75% was 14%, 49%, or 44% in the 0.1 mg/kg group, 0.5 mg/kg group, or 2.0 mg/kg group, respectively, compared to 12% in the placebo group.

Likewise, the proportion of subjects who demonstrated an improvement of 50% in EASI at week 12 after the start of administration was 43%, 51%, or 41% in the 0.1 mg/kg group, 0.5 mg/kg group, or 2.0 mg/kg group, respectively, compared to 33% in the placebo group. The proportion of subjects who demonstrated an improvement of 75% was 23%, 37%, or 22% in the 0.1 mg/kg group, 0.5 mg/kg group, or 2.0 mg/kg group, respectively, compared to 14% in the placebo group.

The proportion of subjects who demonstrated an improvement of 50% in SCORAD at week 12 after the start of administration was 18%, 39%, or 31% in the 0.1 mg/kg group, 0.5 mg/kg group, or 2.0 mg/kg group, respectively, compared to 15% in the placebo group. The proportion of subjects who demonstrated an improvement of 75% was 0%, 15%, or 17% in the 0.1 mg/kg group, 0.5 mg/kg group, or 2.0 mg/kg group, respectively, compared to 3% in the placebo group.

Proportion of Subjects Who Demonstrated an Improvement by 2 or More Points: sIGA and Pruritus VRS For each endpoint, the proportion of subjects who demonstrated an improvement by 2 or more points from baseline until each time point was calculated.

With respect to the results for the groups to which CIM331 was administered every 4 weeks in Part A, the proportion of subjects who demonstrated an improvement by 2 points or more in sIGA at week 12 after the start of administration was 21%, 30%, or 22% in the 0.1 mg/kg group, 0.5 mg/kg group, or 2.0 mg/kg group, respectively, compared to 12% in the placebo group.

The proportion of subjects who demonstrated an improvement by 2 points or more in pruritus VRS at week 12 after the start of administration was 14%, 47%, or 30% in the 0.1 mg/kg group, 0.5 mg/kg group, or 2.0 mg/kg group, respectively, compared to 5% in the placebo group.

Degree of Improvement: Pruritus VAS, EASI, SCORAD, sIGA, BSA of Atopic Dermatitis Lesions, Pruritus VRS, and Sleep Disturbance VAS For each endpoint, degrees of improvements from baseline until each time point were summarized using descriptive statistics.

With respect to the results for the groups to which CIM331 was administered every 4 weeks in Part A, data measured after the receipt of rescue therapy in the PP set were all excluded. In this case, the percent improvement in pruritus VAS at week 4 after the administration was 39%, 55%, or 46% in the 0.1 mg/kg group, 0.5 mg/kg group, or 2.0 mg/kg group, respectively, compared to 12% in the placebo group. The percent improvement at week 12 after the administration was 47%, 68%, or 67% in the 0.1 mg/kg group, 0.5 mg/kg group, or 2.0 mg/kg group, respectively, compared to 24% in the placebo group.

Likewise, the percent improvement in EASI at week 12 after the administration was 34%, 54%, or 48% in the 0.1 mg/kg, 0.5 mg/kg, or 2.0 mg/kg group, respectively, compared to 38% in the placebo group. The percent improvement in SCORAD at week 12 after the administration was 37%, 45%, or 47% in the 0.1 mg/kg, 0.5 mg/kg, or 2.0 mg/kg group, respectively, compared to 22% in the placebo group. The percent improvement in sIGA at week 12 after the administration was 25%, 34%, or 28% in the 0.1 mg/kg, 0.5 mg/kg, or 2.0 mg/kg group, respectively, compared to 13% in the placebo group. The percent improvement in BSA at week 12 after the administration was 25%, 26%, or 33% in the 0.1 mg/kg, 0.5 mg/kg, or 2.0 mg/kg group, respectively, compared to 31% in the placebo group. The percent improvement in pruritus VRS at week 12 after the administration was 42%, 58%, or 58% in the 0.1 mg/kg, 0.5 mg/kg, or 2.0 mg/kg group, respectively, compared to 18% in the placebo group. The percent improvement in sleep disturbance VAS at week 12 after the administration was 57%, 65%, or 67% in the 0.1 mg/kg, 0.5 mg/kg, or 2.0 mg/kg group, respectively, compared to 31% in the placebo group.

Time to Response: Pruritus VAS, EASI, SCORAD, and sIGA

Times from baseline until an improvement of 25%, 50%, or 75% was achieved in pruritus VAS, EASI, and SCORAD and times from baseline until a 2-point improvement was achieved in sIGA were summarized as cumulative incidences over time, using Kaplan-Meier estimates.

With respect to the results for the groups to which CIM331 was administered every 4 weeks in Part A, the time from baseline until 50% of patients achieved an improvement of 25%, 50%, or 75% in pruritus VAS was as follows: 2 weeks, 4 weeks, or not achieved, respectively, in the 0.1 mg/kg group; 2 weeks, 2 weeks, or 5 weeks, respectively, in the 0.5 mg/kg group; and 2 weeks, 4 weeks, or not achieved, respectively, in the 2.0 mg/kg group; compared to 11 weeks, not achieved, or not achieved, respectively, in the placebo group. Moreover, the percent achievement in the improvement of 25%, 50%, or 75% from baseline at week 12 after the start of administration as determined using Kaplan-Meier estimates was as follows: 84%, 66%, or 38%, respectively, in the 0.1 mg/kg group; 95%, 80%, or 68%, respectively, in the 0.5 mg/kg group; and 94%, 71%, or 48%, respectively, in the 2.0 mg/kg group; compared to 52%, 38%, or 22%, respectively, in the placebo group.

Likewise, the time from baseline until 50% of patients achieved an improvement of 25%, 50%, or 75% in EASI was as follows: 2 weeks, 4 weeks, or not achieved, respectively, in the 0.1 mg/kg group; 2 weeks, 4 weeks, or 12 weeks, respectively, in the 0.5 mg/kg group; and 2 weeks, 6 weeks, or not achieved, respectively, in the 2.0 mg/kg group; compared to 6 weeks, 12 weeks, or not achieved, respectively, in the placebo group. Moreover, the percent achievement in the improvement of 25%, 50%, or 75% from baseline at week 12 after the start of administration as determined using Kaplan-Meier estimates was as follows: 71%, 66%, or 37%, respectively, in the 0.1 mg/kg group; 84%, 73%, or 53%, respectively, in the 0.5 mg/kg group; and 93%, 67%, or 28%, respectively, in the 2.0 mg/kg group; compared to 68%, 51%, or 23%, respectively, in the placebo group.

The time from baseline until 50% of patients achieved an improvement of 25%, 50%, or 75% in SCORAD was as follows: 2 weeks, not achieved, or not achieved, respectively, in the 0.1 mg/kg group; 3 weeks, 10 weeks, or not achieved, respectively, in the 0.5 mg/kg group; and 2 weeks, not achieved, or not achieved, respectively, in the 2.0 mg/kg group; compared to 6 weeks, not achieved, or not achieved, respectively, in the placebo group. Moreover, the percent achievement in the improvement of 25%, 50%, or 75% from baseline at week 12 after the start of administration as determined using Kaplan-Meier estimates was as follows: 78%, 46%, or 9%, respectively, in the 0.1 mg/kg group; 78%, 55%, or 30%, respectively, in the 0.5 mg/kg group; and NE (not evaluable), 46%, or 25%, respectively, in the 2.0 mg/kg group; compared to 57%, 40%, or 6%, respectively, in the placebo group.

With respect to the time from baseline until 50% of patients achieved a 2-point improvement in sIGA, such an improvement was not achieved by week 12 in any of the placebo group, 0.1 mg/kg group, 0.5 mg/kg group, and 2.0 mg/kg group. Moreover, the percent achievement in the 2-point improvement from baseline at week 12 after the start of administration as determined using Kaplan-Meier estimates was 36% in the 0.1 mg/kg group, 47% in the 0.5 mg/kg group, or 38% in the 2.0 mg/kg group, compared to 30% in the placebo group.

Period Until the Receipt of Rescue Therapy

Periods until the receipt of rescue therapy were summarized as cumulative incidences over time, using Kaplan-Meier estimates. Subjects who did not receive rescue therapy were censored at the earlier of the hospital visit at week 12 in Part A (or the hospital visit at week 64 in Part B) and the early withdrawal from the clinical study.

With respect to the results for the groups to which CIM331 was administered every 4 weeks in Part A, the time from baseline until 50% of patients received rescue therapy was not achieved by week 12 in any of the placebo group, 0.1 mg/kg group, 0.5 mg/kg group, and 2.0 mg/kg group. Moreover, the time from baseline until 25% of patients received rescue therapy was 5 weeks, 9 weeks, not achieved, or 9 weeks, respectively, in the placebo group, 0.1 mg/kg group, 0.5 mg/kg group, or 2.0 mg/kg group.

Proportion of Subjects Who Received Rescue Therapy

The proportion of subjects who had received rescue therapy at each time point was calculated.

With respect to the results for the groups to which CIM331 was administered every 4 weeks in Part A, the proportion of subjects who received rescue therapy was 26.1% in the 0.1 mg/kg group, 24.4% in the 0.5 mg/kg group, or 29.8% in the 2.0 mg/kg group, compared to 39.1% in the placebo group.

Actigraphy

The results of actigraphy in the groups to which CIM331 was administered every 4 weeks in Part A showed that the actual sleep time from falling asleep to awakening at week 4 after the administration was increased by 49.5 minutes in the 0.1 mg/kg group, increased by 53.1 minutes in the 0.5 mg/kg group, or increased by 48.2 minutes in the 2.0 mg/kg group, compared to an increase by 7.3 minutes in the placebo group. The sleep onset latency (the time from going to bed to falling asleep) at week 4 after the administration was decreased by 17.6 minutes in the 0.1 mg/kg group, decreased by 14.8 minutes in the 0.5 mg/kg group, or decreased by 12.7 minutes in the 2.0 mg/kg group, compared to a decrease by 4.3 minutes in the placebo group.

Furthermore, in the group to which CIM331 was administered once every 8 weeks in Part A, the mean value of percent improvements in pruritus VAS at week 12 after the first administration from which all the data measured after the receipt of rescue therapy were excluded, was 70%.

From the results of pruritus VAS at week 12 after the administration as the primary endpoint, as well as the results of dermatitis scores such as EASI and sIGA in PartA, it was thought that the effects against pruritus and dermatitis reached maximum in the group to which CIM331 was administered at 0.5 mg/kg/4 weeks.

Optimal Dosage Simulations

With respect to dosages, from the viewpoint of further improving the convenience, optimal dosage and administration at a fixed dose were evaluated from dosages per body weight, by performing modeling and simulation.

Initially, exposure was compared between doses per body weight and fixed doses, and optimal dosage and administration were studied from the viewpoint of pharmacokinetics. The serum drug concentration of CIM331 fitted well to a one-compartment model with first order absorption. Moreover, body weight as a covariate was integrated into model parameters, using the allometry equation. The model parameters are shown below.

TABLE 3

| Parameter | Unit | Estimate | Bootstrapped 90% interval |
|---|---|---|---|
| CL/F | L/day | 0.327 | 0.312-0.343 |
| Covariate effect of ALB | | −1.72 | −2.00−−1.38 |
| V/F | L | 7.46 | 7.12-7.83 |
| ka | 1/day | 0.514 | 0.442-0.609 |
| Inter-individual variability | | | |
| Variance for CL/F | | 0.186 | 0.142-0.239 |
| Variance for V/F | | 0.179 | 0.123-0.244 |
| Variance for ka | | 0.276 | 0.182-0.377 |
| Covariance for CL/F and V/F | | 0.134 | 0.0871-0.185 |
| Residucal variability | | | |
| Log normal error (CV) | % | 15.5 | 14.0-17.1 |

Figure 10:
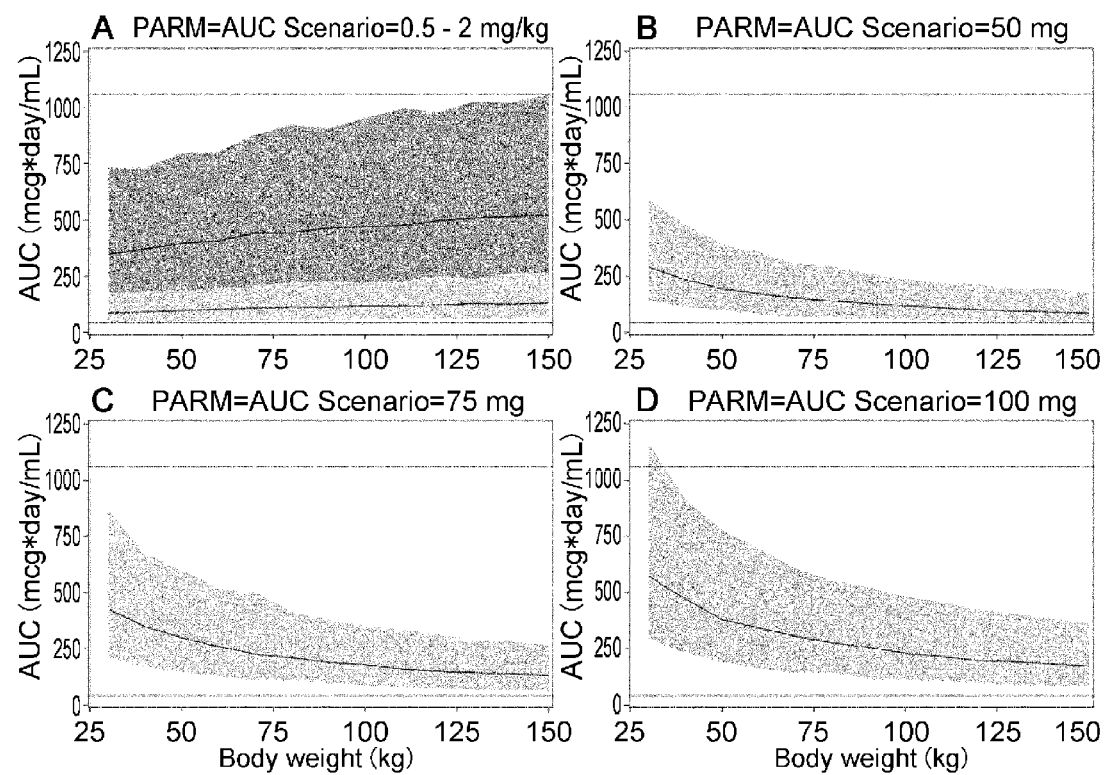
FIG. 10 shows graphs each illustrating the relationship between the body weight and exposure in an optimal dosage simulation of CIM331 using a one-compartment model.

Simulations were performed using the above-described one-compartment model. FIG. 10 shows relationships between the body weight and exposure. In FIG. 10, the graph A shows estimated exposure by administration at 0.5 mg/kg or 2 mg/kg, and the graphs B, C, and D show estimated exposure by administration at 50, 75, and 100 mg/body, respectively. The reference curves in each graph indicate an estimated upper limit of exposure (1060 μg*day/mL) at 2 mg/kg and an estimated lower limit of exposure (44 μg*day/mL) at 0.5 mg/kg.

When the dosage was fixed at 50 mg, the lower limit of exposure at approximately 0.5 mg/kg was estimated to be exceeded at a body weight below 100 kg, and when the dosage was fixed at 100 mg, the upper limit of exposure at 2 mg/kg was estimated to be exceeded at low body weights. Moreover, when the dosage was fixed at 75 mg, the exposure was estimated to fall within the range of exposure obtained at 0.5 mg/kg or 2 mg/kg. From these results, it was thought that the administration of CIM331 once every 4 weeks at a fixed dosage of 50 mg (or 100 mg for a body weight over 100 kg) or 75 mg would result in exposure similar to that obtained in the phase II study.

Subsequently, modeling and simulation was performed on pruritus VAS, using PK/PD analysis. An indirect turnover model was used for the part of pruritus VAS, and scale conversion was performed. Model predicted values were confirmed to imitate actual measurements well. The calculated model parameters are shown below.

TABLE 4

| Parameter | Unit | Estimate | Bootstrapped 90% interval |
|---|---|---|---|
| Kout | 1/day | 0.0710 | 0.0578-0.0839 |
| Placebo effect | — | 0.554 | 0.400-0.769 |
| Imax | — | 0.893 | 0.490-1.50 |
| IC50 | μg/mL | 3.21 | 0.956-9.43 |
| Inter-individual variability | | | |
| Variance for kout | — | 0.581 | 0.396-0.809 |
| Variance for Placebo effect | — | 0.983 | 0.737-1.46 |
| Variance for Imax | — | 1.81 | 0.712-3.01 |
| Residucal variability | | | |
| Additive error | — | 0.0276 | 0.0193-0.0354 |
| Proportional error (CV) | % | 25.9 | 23.3-28.7 |

Figure 11:
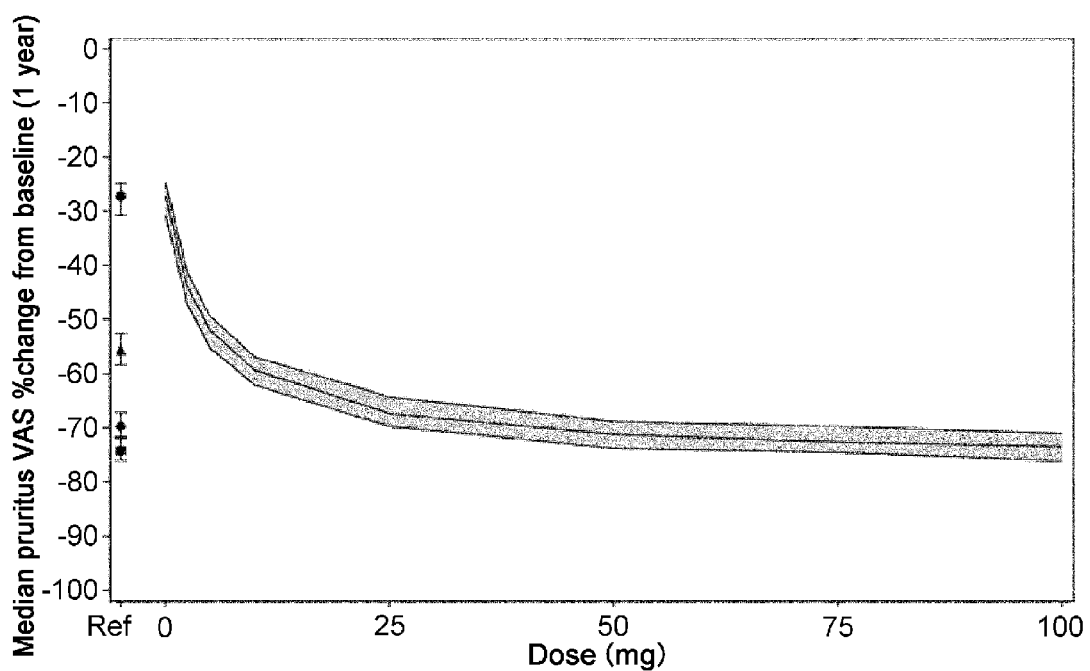
FIG. 11 shows estimated pruritus VAS at a year after the administration of CIM331 using an indirect turnover model.

Simulations were performed using the model. FIG. 11 shows estimated pruritus VAS at 1 year after the administration of CIM331.

When the fixed dosage per 4 weeks was 25 mg/body or more, and preferably 50 mg/body or more, pruritus VAS was estimated to show values similar to those at 0.5 mg/kg or 2 mg/kg.

(4-5) Effect of Combined Administration of CIM331 and a Topical Steroid or the Like Although Part A did not allow the use of a therapeutic drug for atopic dermatitis other than a moisturizer in combination with CIM331, Part B allowed the use of a topical steroid classified as Mild (e.g., hydrocortisone, desonide, or prednisolone), a topical calcineurin inhibitor (e.g., pimecrolimus or tacrolimus), or an antihistamine (e.g., fexofenadine) in combination with CIM331. For ranking and classification of topical steroids, criteria were provided based on NICE Guideline CG57 "Atopic eczema in children: management of atopic eczema in children from birth up to the age of 12 years", with the addition of preparations used solely in Japan and the United States. In patients in which a sufficient dermatitis-improving effect was not demonstrated although a sufficient pruritus-improving effect was demonstrated through the administration of CIM331 in Part A period, a continuous and remarkable dermatitis-improving effect was demonstrated by the administration of topical steroid or the like for a short or required period in combination with CIM331 in Part B.

In the phase II repeated dose study, suppression of pruritus by the administration of CIM331 could break the scratching-induced vicious circle involving reduced barrier function→increase in inflammatory responses due to the invasion of foreign antigens→aggravation of dermatitis→exacerbation of pruritus, leading to the effect of improving dermatitis. Moreover, in patients in which a sufficient dermatitis-improving effect was not demonstrated although a sufficient pruritus-improving effect was demonstrated through the administration of CIM331, a sustained improvement of dermatitis was achieved through the administration of a topical steroid or the like for a short period of time in combination with CIM331. Thus, it was suggested that dermatitis can be more effectively improved by preventing a new exacerbation of atopic dermatitis due to the itch-scratch cycle, by suppressing existing inflammatory responses through the use of a topical steroid in combination, while persistently suppressing pruritus through the use of CIM331.

(4-6) Expected Results and Advantageous Effects

Repeated administration of CIM331 every 4 or 8 weeks achieves a steady-state serum concentration of CIM331, and hence, can demonstrate a sustained effect against the pruritus in patients with atopic dermatitis. Moreover, the maintenance of the pruritus-improving effect, i.e., the blockage of the itch-scratch cycle, can improve dermatitis, and can improve the QOL. A long-term efficacy profile over a total period of 64 weeks can be confirmed.

Furthermore, in view of the fact that the currently existing systemic therapeutic methods for atopic dermatitis require taking a medicine or applying a medicine to an affected area several times a day, or ultraviolet therapy may require a visit to the hospital as many as once or twice a week, a therapeutic embodiment involving repeatedly administering CIM331 every 4 or 8 weeks, for example, can be expected to markedly alleviate the patient's burden of taking the medicine or visiting the hospital, for example, and can further contribute to improving the patient's QOL.

(4-7) Embodiments of CIM331 after Approval

CIM331 may be administered to patients with moderate or severe atopic dermatitis for which topical therapy is not sufficiently effective or is intolerable, but not limited thereto. CIM331 may be subcutaneously administered repeatedly in equal dosages at the same dosing interval, for example, once every 2 to 12 weeks, and specifically, for example, every 2, 3, 4, 5, 6, 7, 8, 9, 10, 11, or 12 weeks, or once every 1, 2, or 3 months.

The dosage of CIM331 per body weight and the concentration of the CIM331 solution for administration may be determined as appropriate, based on the results of the phase II repeated administration study or the results of other studies, for example. For example, when the body weight of a patient with atopic dermatitis exceeds 120 kg, an investigational drug may be prepared on the assumption that the body weight is 120 kg. Furthermore, when it is intended that CIM331 be administered in mg/body to a patient with atopic dermatitis, dosages in mg/kg of CIM331 may be converted to dosages in mg/body, based on the results of the phase II repeated study, for example, and an appropriate dosage (mg/body) may be selected and administered. In this case, although the logic for converting mg/kg to mg/body is not limited, it will be understood that a person skilled in the art can determine a dosage in mg/body, as appropriate, by using the following logic.

Assuming that there are the minimum effective serum concentration and the maximum tolerable (empirical) serum concentration of CIM331, changing of a dosage in mg/kg into a dosage in mg/body is considered based on the results of the phase II study, such that a serum concentration of CIM331 within this range of concentrations is achieved, regardless of body weight. Moreover, because a dosage in mg/body for a child with a low body weight may markedly increase the exposure, a dosage in mg/kg is considered in such a case. Conversion to mg/body can be accomplished by determining the minimum effective serum concentration and the maximum tolerable serum concentration of CIM331 from the results of the phase II study that is currently being performed, and adjusting the exposure as described above.

In a non-limiting embodiment, for an adult or pediatric patient with atopic dermatitis, one dosage may be selected from 0.1 to 1000 mg/body, for example, 0.2 to 360 mg/body, and preferably 10 to 200 mg/body, 10 to 100 mg/body, 25 to 100 mg/body, 50 to 100 mg/body, or 50 to 75 mg/body, and may be subcutaneously administered repeatedly using the above-described dosing interval, in equal amounts at the same dosing interval. For the sake of avoiding any doubt, it is expressly stated that, for example, the recitation "0.1 to 1000 mg/body" is intended to mean that all the dosages included between 0.1 and 1000 mg/body are specifically and individually recited, with a variation of 0.1 mg/body, for example, 0.1 mg/body, 0.2 mg/body, 0.3 mg/body, 0.4 mg/body, . . . 49.9 mg/body, 50 mg/body, 50.1 mg/body, 50.2 mg/body, . . . 99.8 mg/body, 99.9 mg/body, 100 mg/body, 100.1 mg/body, 100.2 mg/body, . . . 199.9 mg/body, 200 mg/body, 200.1 mg/body, . . . 359.8 mg/body, 359.9 mg/body, 360 mg/body, 360.1 mg/body, . . . 999.8 mg/body, 999.9 mg/body, and 1000 mg/body. Thus, a person who has read this recitation will naturally understand directly and unambiguously, from the recitation "0.1 to 1000 mg/body", for example, that values such as 55 mg/body and 56.5 mg/body are specifically and individually recited in the Examples.

Alternatively, in another non-limiting embodiment, for a pediatric patient with atopic dermatitis, one dosage may be selected from 0.01 to 10 mg/kg, for example, 0.1 to 3 mg/kg, and preferably 0.2 to 2 mg/kg, and may be subcutaneously administered repeatedly using the above-described dosing interval, in equal amounts at the same dosing interval. For the sake of avoiding any doubt, it is expressly stated that, for example, the recitation "0.01 to 10 mg/kg" is intended to mean that all the dosages included between 0.01 and 10 mg/kg are specifically and individually recited, with a variation of 0.005 mg/body, for example, 0.01 mg/kg, 0.015 mg/kg, 0.02 mg/kg, 0.025 mg/kg, 0.03 mg/kg, 0.035 mg/kg, 0.04 mg/kg, . . . 0.125 mg/kg, . . . 0.49 mg/kg, 0.495 mg/kg, 0.5 mg/kg, 0.505 mg/kg, 0.51 mg/kg, . . . 0.98 mg/kg, 0.985 mg/kg, 0.99 mg/kg, 0.995 mg/kg, 1 mg/kg, 1.005 mg/kg, 1.01 mg/kg, . . . 1.49 mg/kg, 1.495 mg/kg, 1.5 mg/kg, 1.505 mg/kg, 1.51 mg/kg, . . . 1.98 mg/kg, 1.985 mg/kg, 1.99 mg/kg, 1.995 mg/kg, 2 mg/kg, 2.005 mg/kg, 2.01 mg/kg, . . . 2.99 mg/kg, 2.995 mg/kg, 3 mg/kg, 3.005 mg/kg, 3.01 mg/kg, . . . 9.98 mg/kg, 9.985 mg/kg, 9.99 mg/kg, 9.995 mg/kg, and 10 mg/kg. Thus, a person who has read this recitation will naturally understand directly and unambiguously, from the recitation "0.01 to 10 mg/kg", for example, that values such as 0.75 mg/kg and 1.245 mg/kg are specifically and individually recited in the Examples.

Reference Example 1

Expression and Purification of IgG Antibodies

The expression of antibodies was performed using the following method. Human fetal renal cancer cell-derived HEK293H cell line (Invitrogen) was suspended in DMEM medium (Invitrogen) supplemented with 10% Fetal Bovine Serum (Invitrogen). The cells were plated at 10 mL per dish for adherent cells (10 cm in diameter; CORNING) at a cell density of 5 to $6 \times 10^5$ cells/mL, and cultured in a $CO_2$ incubator (37° C., 5% $CO_2$) for one whole day and night. The medium was then removed by aspiration, and 6.9 mL of CHO-S-SFM-II (Invitrogen) medium was added. The prepared plasmid was introduced into the cells by the lipofection method. The resulting culture supernatants were collected and centrifuged (about 2000 g, 5 min, room temperature) to remove the cells, and sterilized by filtering through 0.22-μm filter MILLEX (R)-GV (Millipore) to obtain culture supernatants. Antibodies were purified from the obtained culture supernatants by a method known to those skilled in the art using rProtein A Sepharose™ Fast Flow (Amersham Biosciences). To determine concentrations of the purified antibodies, absorbance was measured at 280 nm using a spectrophotometer. The antibody concentrations were calculated from the determined value, using an absorbance coefficient calculated by the method described in Protein Science 1995; 4: 2411-2423.

The invention claimed is:

1. A method of treating, or reducing the incidence of, a symptom of atopic dermatitis in a human patient, the method comprising subcutaneously administering to the patient a series of doses of an anti-human IL-31RA antibody, wherein the anti-human IL-31 RA antibody comprises an H chain variable region comprising CDR1 as set forth in SEQ ID NO: 1, CDR2 as set forth in SEQ ID NO: 2, and CDR3 as set forth in SEQ ID NO: 3, and an L chain variable region comprising CDR1 as set forth in SEQ ID NO: 4, CDR2 as set forth in SEQ ID NO: 5, and CDR3 as set forth in SEQ ID NO: 6;
wherein the amount of the anti-human IL-31RA antibody in each individual dose in the series is 0.5 mg/kg; and
wherein the interval between each administration and the next is 4 weeks.

2. The method of claim 1, wherein the symptom is pruritus.

3. The method of claim 1, wherein, prior to the first administration of the anti-human IL-31RA antibody, the patient had experienced sleep disturbance caused by pruritus associated with atopic dermatitis, and wherein the method results in the patient's experiencing a reduction in sleep disturbance caused by pruritus, wherein the reduction in sleep disturbance is attributable at least in part to an increase in the time span from falling asleep to awakening, or a decrease in sleep onset latency, or both.

4. The method of claim 1, wherein the anti-human IL-31 RA antibody comprises a human IgG2 Fc region comprising an amino acid sequence with glutamic acid at position 419 (EU numbering).

5. The method of claim 1, further comprising administering a topical composition to the patient, wherein the topical composition comprises a topical steroid or a topical calcineurin inhibitor and is administered before, simultaneously with, or after at least one administration of the anti-human IL-31RA antibody.

6. The method of claim 5, wherein the method produces a reduction in symptoms of atopic dermatitis in the patient that is greater than the reduction in symptoms induced by treatment with the anti-human IL-31RA antibody alone.

7. The method of claim 5, wherein the method permits a lower dosage of the topical composition to be administered than would be needed when the topical composition is administered as a single agent to the patient in the absence of treatment with the anti-human IL-31RA antibody, in order to produce a comparable decrease in symptoms of atopic dermatitis.

8. The method of claim 1, wherein the anti-human IL-31RA antibody binds to and neutralizes human IL-31RA and comprises an H chain variable region as set forth in SEQ ID NO: 7 and an L chain variable region as set forth in SEQ ID NO: 8.

9. The method of claim 1, wherein the anti-human IL-31RA antibody binds to and neutralizes human IL-31RA and comprises an H chain as set forth in SEQ ID NO: 9 and an L chain as set forth in SEQ ID NO: 10.

10. A method of treating, or reducing the incidence of, a symptom of atopic dermatitis in a human patient, the method comprising administering to the patient an initial dose of an anti-human IL-31RA antibody, followed by subcutaneously administering two or more continuous doses of the anti-human IL-31RA antibody,
wherein the amount of the anti-human IL-31RA antibody in each of the continuous doses is 0.5 mg/kg,
wherein the interval between each two sequential administrations of the continuous doses is 4 weeks, and
wherein the anti-human IL-31 RA antibody comprises an H chain variable region comprising CDR1 as set forth in SEQ ID NO: 1, CDR2 as set forth in SEQ ID NO: 2, and CDR3 as set forth in SEQ ID NO: 3, and an L chain variable region comprising CDR1 as set forth in SEQ ID NO: 4, CDR2 as set forth in SEQ ID NO: 5, and CDR3 as set forth in SEQ ID NO: 6.

11. A method of treating, or reducing the incidence of, a symptom of atopic dermatitis in a human patient, the method comprising administering to the patient an initial dose of an anti-human IL-31RA antibody, followed by subcutaneously administering two or more continuous doses of the anti-human IL-31RA antibody,
wherein the amount of the anti-human IL-31RA antibody in each of the continuous doses is 30 mg/body,
wherein the interval between each two sequential administrations of the continuous doses is 4 weeks, and
wherein the anti-human IL-31 RA antibody comprises an H chain variable region comprising CDR1 as set forth in SEQ ID NO: 1, CDR2 as set forth in SEQ ID NO: 2, and CDR3 as set forth in SEQ ID NO: 3, and an L chain variable region comprising CDR1 as set forth in SEQ ID NO: 4, CDR2 as set forth in SEQ ID NO: 5, and CDR3 as set forth in SEQ ID NO: 6.

12. A method of treating, or reducing the incidence of, a symptom of atopic dermatitis in a human patient, the method comprising subcutaneously administering to the patient a series of doses of an anti-human IL-31RA antibody comprising an H chain variable region comprising CDR1 as set forth in SEQ ID NO: 1, CDR2 as set forth in SEQ ID NO: 2, and CDR3 as set forth in SEQ ID NO: 3, and an L chain variable region comprising CDR1 as set forth in SEQ ID NO: 4, CDR2 as set forth in SEQ ID NO: 5, and CDR3 as set forth in SEQ ID NO: 6,
wherein the amount of the anti-human IL-31RA antibody in each individual dose in the series is 30 mg/body, and
wherein the interval between each administration and the next is 4 weeks.

* * * * *